(12) United States Patent
Ueda et al.

(10) Patent No.: US 10,322,260 B2
(45) Date of Patent: Jun. 18, 2019

(54) TREATMENT METHOD FOR TREATING LOWER LIMBS USING MULTI-MEMBER CATHETER ASSEMBLY

(71) Applicant: TERUMO KABUSHIKI KAISHA, Shibuya-ku (JP)

(72) Inventors: Mariko Ueda, Shizuoka (JP); Tetsuya Fukuoka, Shizuoka (JP)

(73) Assignee: TERUMO KABUSHIKI KAISHA, Shibuya-Ku, Tokyo (JP)

( * ) Notice: Subject to any disclaimer, the term of this patent is extended or adjusted under 35 U.S.C. 154(b) by 1047 days.

(21) Appl. No.: 14/290,338

(22) Filed: May 29, 2014

(65) Prior Publication Data

US 2014/0358123 A1 Dec. 4, 2014

(30) Foreign Application Priority Data

May 30, 2013 (JP) ................................. 2013-114106
Mar. 28, 2014 (JP) ................................. 2014-067600

(51) Int. Cl.
*A61M 25/00* (2006.01)
*A61M 25/06* (2006.01)
(Continued)

(52) U.S. Cl.
CPC ......... *A61M 25/0097* (2013.01); *A61F 2/958* (2013.01); *A61M 25/0053* (2013.01);
(Continued)

(58) Field of Classification Search
CPC ...... A61M 25/0169; A61M 2025/0175; A61M 2025/0183; A61M 2025/0681; A61M 2210/086; A61M 2210/12
See application file for complete search history.

(56) References Cited

U.S. PATENT DOCUMENTS 4,696,304 A * 9/1987 Chin ...................... A61B 5/028
600/486
5,120,323 A * 6/1992 Shockey ............... A61M 25/01
600/434
(Continued)

FOREIGN PATENT DOCUMENTS

JP 2005-110721 A 4/2005
JP 2008-142351 A 6/2008
(Continued)

OTHER PUBLICATIONS

Sanghvi K, Kurian D, Coppola J. Transradial Intervention of Iliac and Superficial Femoral Artery Disease is Feasible. J Interv Cardiol 2008;21:385-387.*
(Continued)

*Primary Examiner* — Kami A Bosworth
(74) *Attorney, Agent, or Firm* — Buchanan Ingersoll & Rooney PC

(57) ABSTRACT

In the treatment method, a surgeon introduces a catheter assembly into a blood vessel in an arm, and delivers a distal portion of the catheter assembly to a predetermined position of a lower limb through the blood vessel in the body. Moreover, in the treatment method, the surgeon pulls an inner catheter out of an outer catheter, causes a treatment device to advance to the treatment target through the inside of the outer catheter, and treats the treatment target by the treatment device.

19 Claims, 29 Drawing Sheets

(51) Int. Cl.
 *A61F 2/958* (2013.01)
 *A61M 25/01* (2006.01)
(52) U.S. Cl.
 CPC ..... *A61M 25/0662* (2013.01); *A61M 25/0169* (2013.01); *A61M 2025/0059* (2013.01); *A61M 2025/0175* (2013.01); *A61M 2025/0183* (2013.01); *A61M 2025/0681* (2013.01); *A61M 2210/086* (2013.01); *A61M 2210/12* (2013.01); *A61M 2210/127* (2013.01)

(56) References Cited

U.S. PATENT DOCUMENTS

| | | | | |
|---|---|---|---|---|
| 5,558,635 | A | * | 9/1996 | Cannon ............. A61M 25/0169 604/264 |
| 2009/0264865 | A1 | * | 10/2009 | Kawai ............... A61M 25/0105 604/528 |
| 2010/0030165 | A1 | | 2/2010 | Takagi et al. |
| 2012/0130235 | A1 | * | 5/2012 | Conn ............... A61B 17/06109 600/431 |

FOREIGN PATENT DOCUMENTS

| | | |
|---|---|---|
| JP | 2009-273640 A | 11/2009 |
| JP | 2009-273641 A | 11/2009 |
| JP | 2010-029559 A | 2/2010 |
| WO | 2012/035633 A1 | 3/2012 |

OTHER PUBLICATIONS

International Search Report (Form PCT/ISA/210) dated Apr. 28, 2015, by the Japanese Patent Office in corresponding International Patent Application No. PCT/JP2015/054969. (1 page).

R. Caputo et al., "Transradial Arterial Access for Coronary and Peripheral Procedures: Executive Summary by the Transradial Committee of the SCAI", Catheterization and Cardiovascular Interventions, Nov. 2011, pp. 823-839, vol. 78, Issue 6.

* cited by examiner

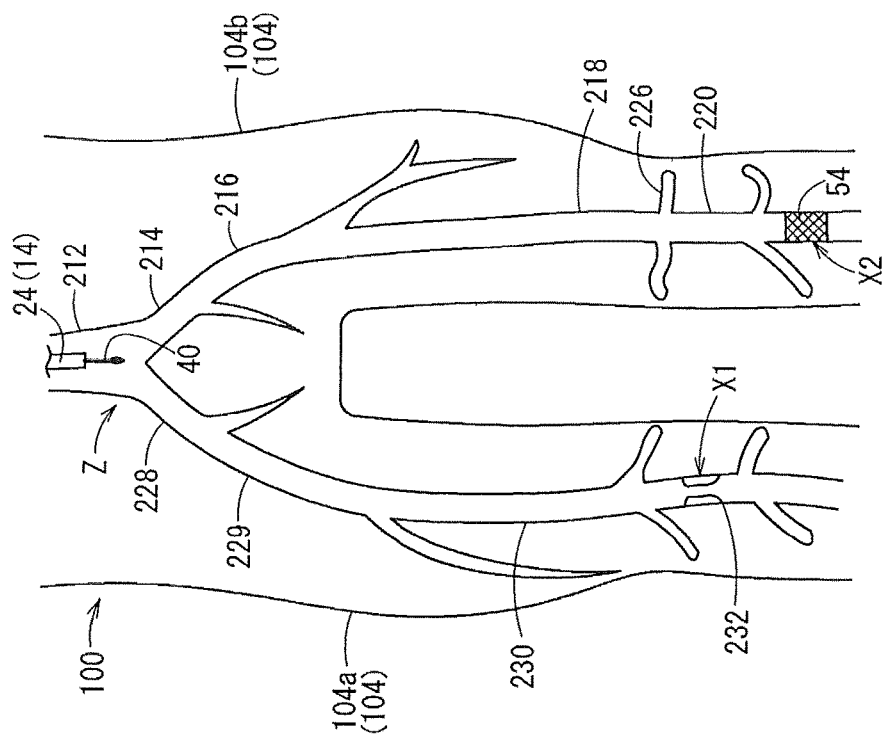
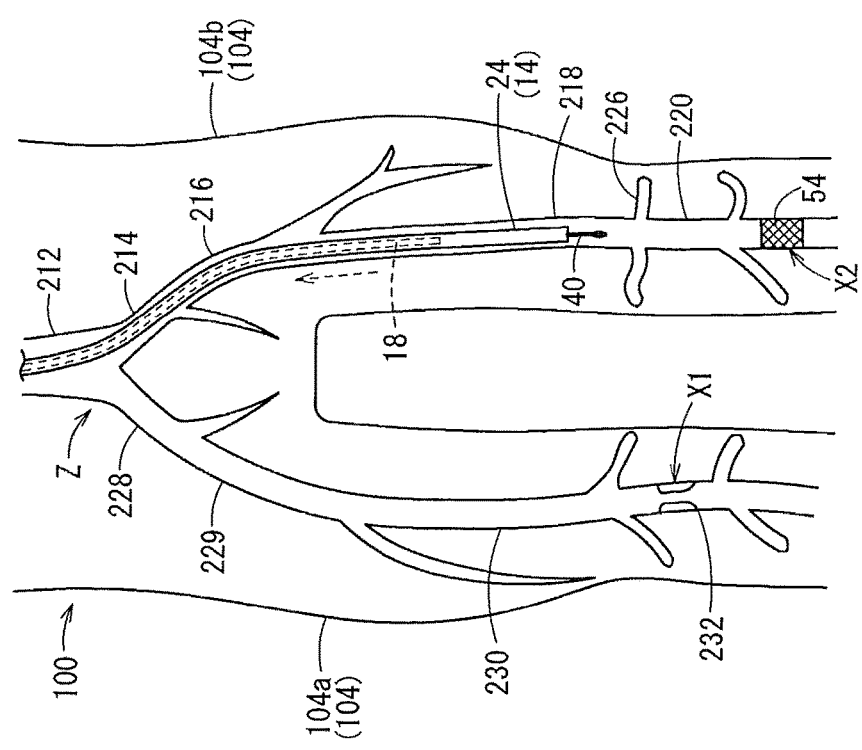

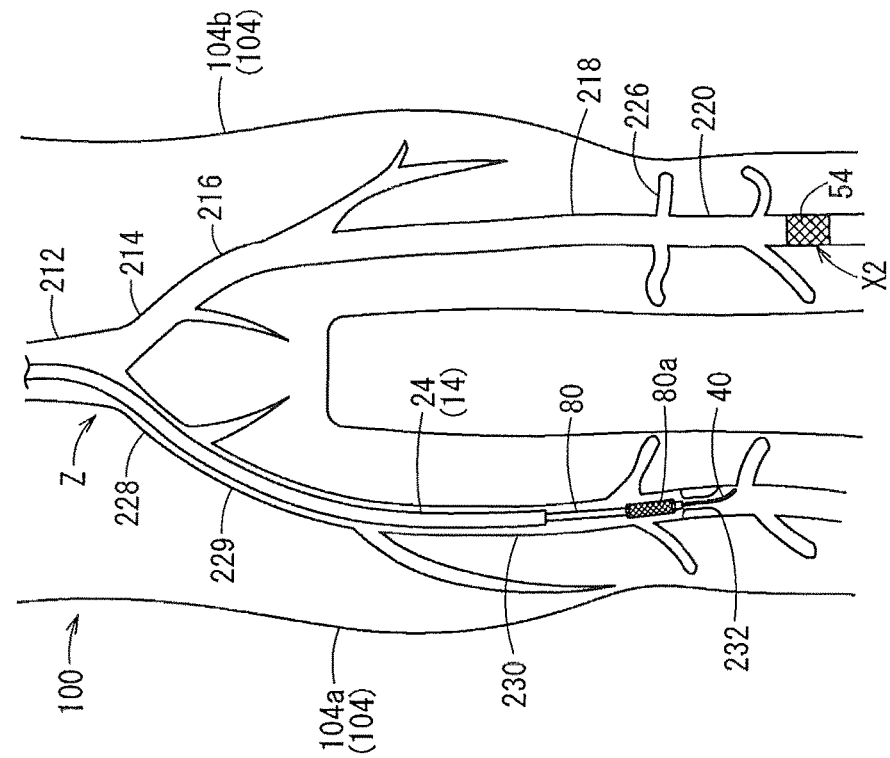
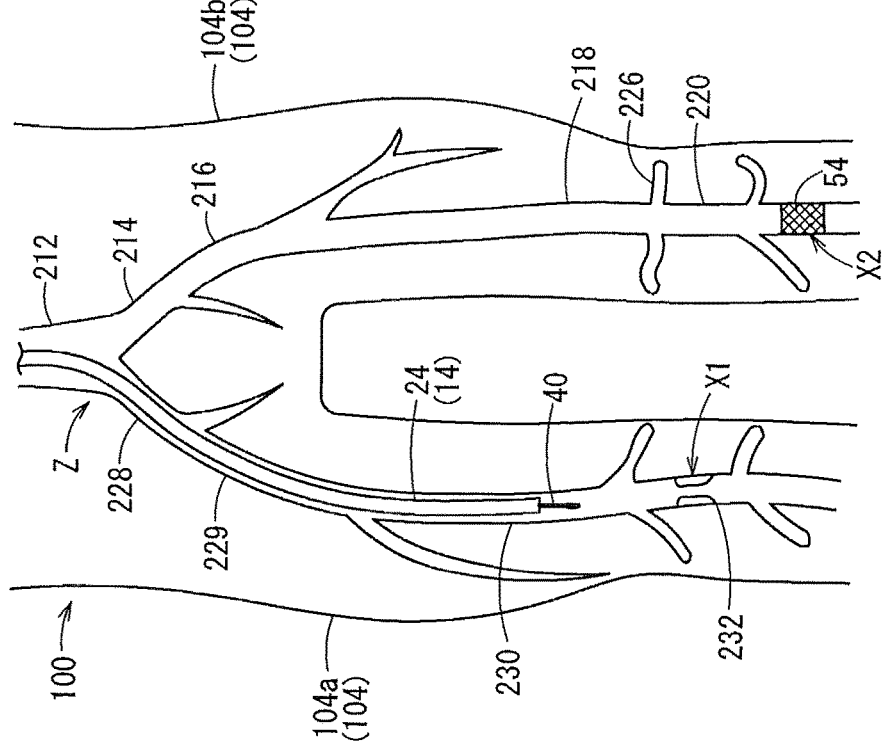

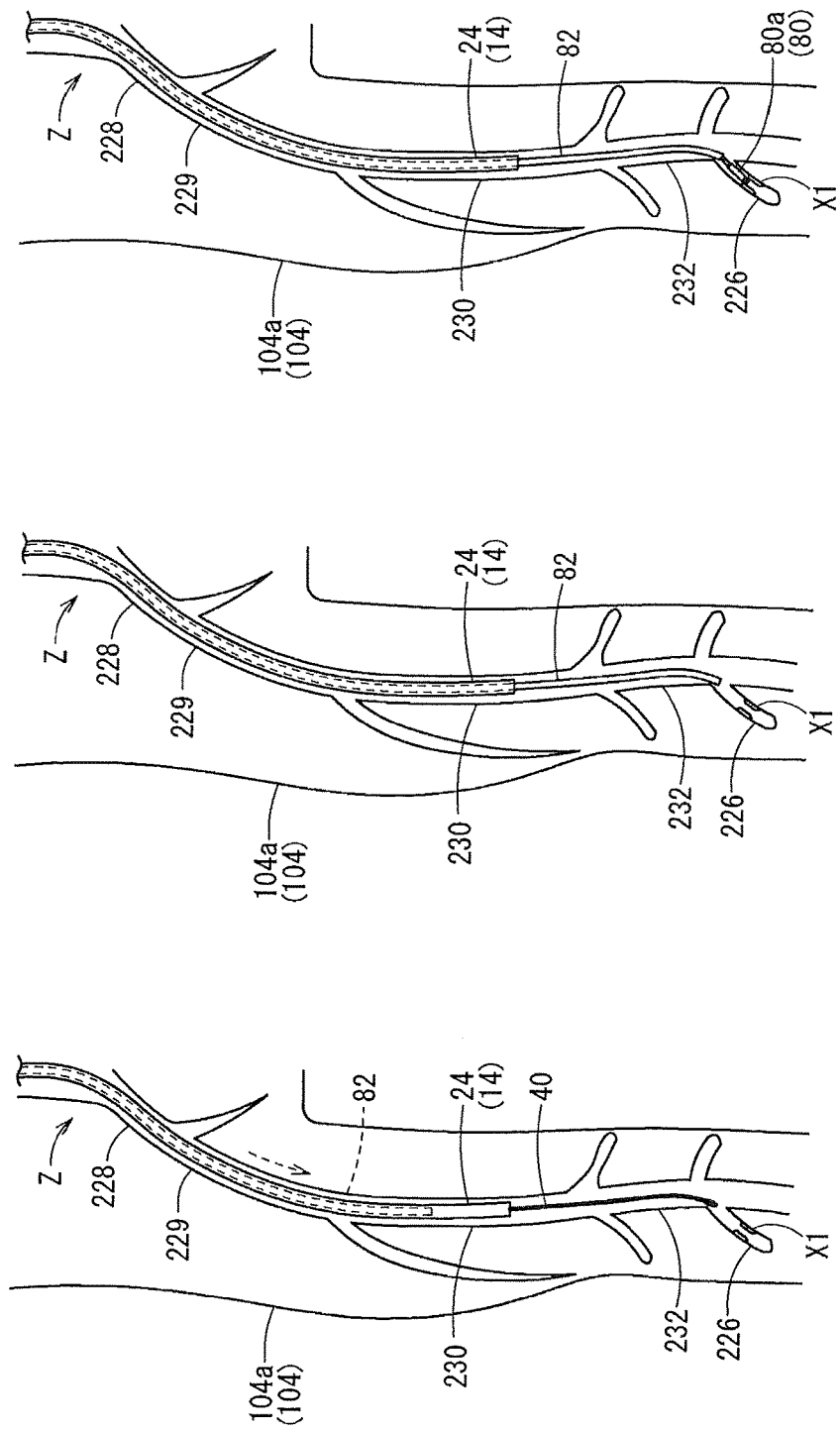

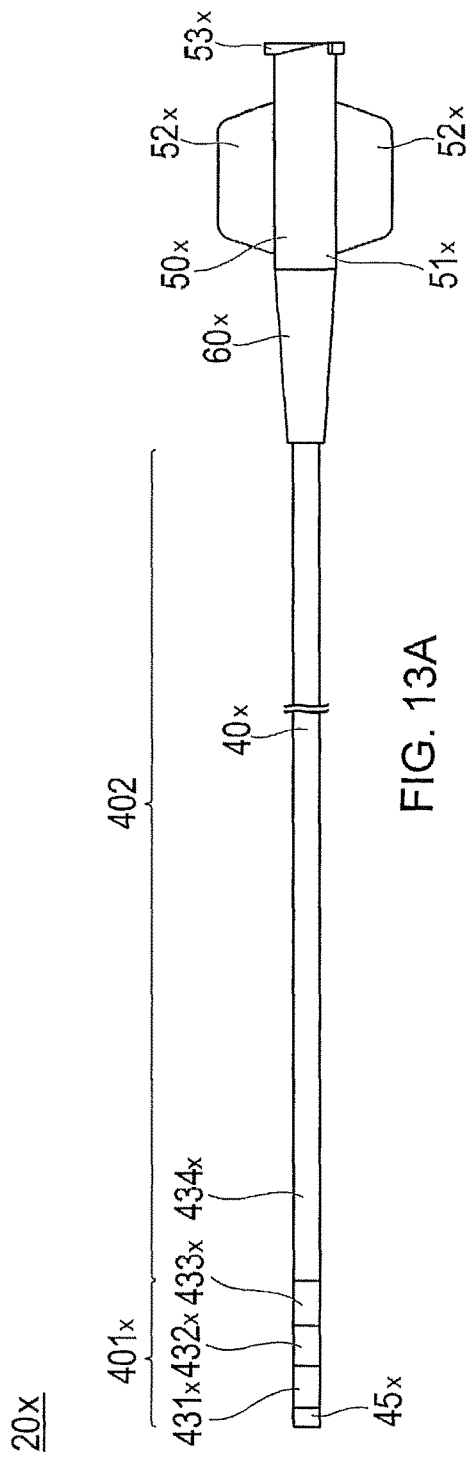
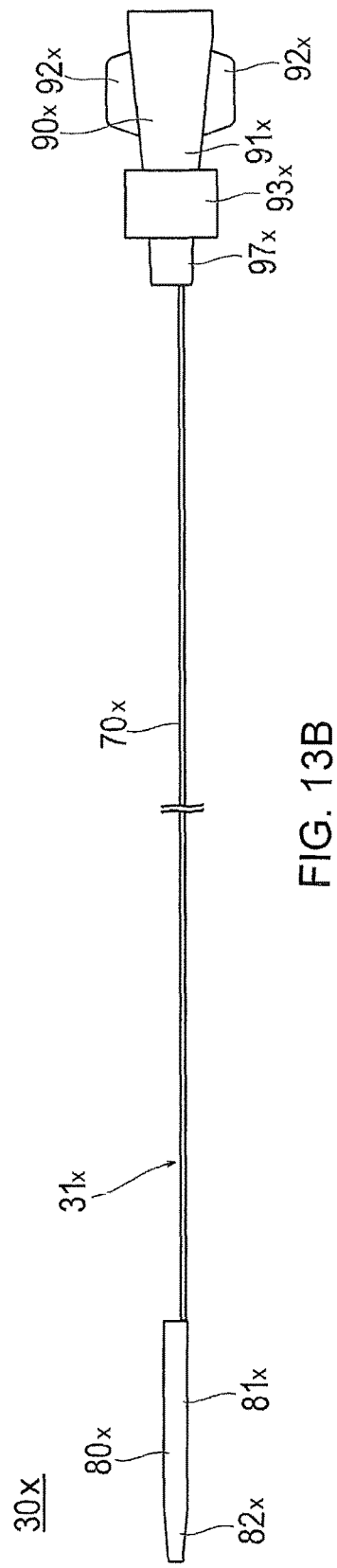
FIG. 13A
FIG. 13B

TREATMENT METHOD FOR TREATING LOWER LIMBS USING MULTI-MEMBER CATHETER ASSEMBLY

CROSS REFERENCES TO RELATED APPLICATIONS

This application claims priority to Japanese Application No. 2013-114106 filed on May 30, 2013 and Japanese Application No. 2014-067600 filed on Mar. 28, 2014, the entire content of both of which is incorporated herein by reference.

TECHNICAL FIELD

The present invention generally relates to a treatment method for treating lower limbs using an intervention procedure. The present invention also generally relates to a catheter assembly including a first catheter (outer catheter) and a second catheter (inner catheter) that is introduced into the lumen of the first catheter (outer catheter).

BACKGROUND DISCUSSION

Conventionally, during an intervention procedure, in many cases, a catheter is introduced into the femoral artery from the femoral region of a patient, and the distal portion of the catheter is delivered to a treatment target in the lumen to treat the target. In recent years, a procedure of providing treatment by introducing the catheter from the artery of arm, particularly, from the radial artery (or the brachial artery) (TRI: Trans Radial Intervention) has been conducted more frequently, for the reasons that a patient suffers from only a slight physical strain by the procedure and can leave the hospital soon.

For example, "Catheterization and Cardiovascular Interventions, Volume 78, Issue 6, pp 823-839, 15 Nov. 2011 "Transradial arterial access for coronary and peripheral procedures: Executive summary by the transradial committee of the SCAI" discloses a treatment method in which Percutaneous Coronary Intervention (PCI) is conducted by introducing a catheter from an arm. The above document also discloses, as an application example of catheterization, a method of treating a lesion formed inside the blood vessel of a lower limb, for example, Peripheral Arterial Disease (PAD) by delivering a catheter to the lesion.

SUMMARY

When an intervention procedure, in which a catheter is introduced from the artery of an arm (radial artery or brachial artery), is conducted to treat the lower limb, a catheter which has a sufficient length needs to be used. However, if a catheter which has been simply lengthened in terms of the full length is used, properties of the catheter (kink resistance, torque-transmitting properties, operability, and the like) deteriorate when the catheter is delivered, and accordingly, a high degree of skill is required for treating the lower limb.

The disclosure here relates to an intervention procedure in which a catheter is introduced from the arm to treat the lower limb. A treatment method is disclosed which provides excellent treatment by making it rather easy to deliver a catheter to a treatment target inside the lumen of the lower limb. Also disclosed is a catheter assembly including a first catheter and a second catheter that are suitable for an intervention procedure in which a catheter is introduced from the arm to treat the lower limb. The catheter assembly makes it possible to relatively easily withdraw a second catheter (inner catheter) from a blood vessel, while leaving a first catheter (outer catheter) and a guide wire inside the blood vessel, when a guide wire is inserted into the catheter assembly.

One aspect of the disclosure here involves a treatment method for treating a treatment target of at least one of the lower limbs. The treatment method includes introducing a catheter assembly, composed of a first catheter and a second catheter disposed in the lumen of the first catheter, into a blood vessel of an arm, delivering a portion of the catheter assembly by operating a portion exposed to the outside, and delivering the distal end of the catheter assembly to a predetermined position of the lower limb through the aorta, advancing a treatment device for treating the treatment target toward the treatment target through the inside of the first catheter after the delivery step, and treating the treatment target by the treatment device.

According to the above method, by using the catheter assembly composed of two catheters including the first and second catheters, a surgeon can rather smoothly deliver the catheter assembly to a predetermined position of the lower limb in the delivery step. That is, since the catheter assembly has a double catheter structure composed of the first and second catheters, the properties (kink resistance, torque-transmitting properties, operability, and the like) required at the time of delivery are improved. As a result, even if the catheter assembly is long enough to reach the lower limb from the arm, the surgeon can rather easily deliver the distal portion of the catheter assembly. Consequently, with this treatment method, the first catheter can be efficiently disposed in a predetermined position, and the treatment device can be rapidly and accurately delivered to the treatment target through the inside of the first catheter, hence excellent treatment can be provided.

In this case, the treatment method may further include, before advancing the device, a catheter advance step in which the distal end of the second catheter or the distal end of a third catheter, which is introduced after the second catheter is withdrawn, is caused to advance near the treatment target through the inside of the first catheter. In the device advance step, the treatment device may be caused to advance through the lumen of the second catheter or the third catheter.

As described above, in the treatment method, since the second catheter or the third catheter is caused to advance from the first catheter, the treatment device can be delivered to various blood vessels present in the lower limb. That is, since the second catheter or the third catheter having a diameter smaller than that of the first catheter is delivered to the blood vessels, even when the treatment target is present in a smaller blood vessel, the second catheter or the third catheter can be caused to advance near the treatment target, and then the treatment device can be introduced.

When the treatment target is present in both the first and second lower limbs constituting the left and right lower limbs of a patient, the treatment target of the first lower limb is treated in the treatment step. In this case, it is preferable for the treatment method to have, after the treatment step, a retreat step in which the distal end of the first catheter is caused to return to a connection position of a blood vessel of the first lower limb and a blood vessel of the second lower limb, a step of delivery to an individual site in which the first catheter is delivered to a predetermined position of the second lower limb from the connection position after the retreat step, a step of causing a device to advance to an individual site in which an individual site treatment device, which is for treating the treatment target of the second lower limb, is caused to advance to the treatment target of the second lower limb through the inside of the first catheter after the step of delivery to an individual site, and an individual site treatment step in which the treatment target of the second lower limb is treated by the individual site treatment device.

According to the above method, a surgeon can consecutively conduct an intervention procedure for the treatment target of each of the two lower limbs (the first and second lower limbs). That is, after treating the treatment target of the first lower limb, the surgeon moves the first catheter to retreat to the connection position, and then provides treatment by moving the first catheter to advance to the treatment target of the second lower limb. As a result, plural treatment targets present in different sites can be efficiently treated by a single treatment.

In this case, the treatment method may further include, before the individual site treatment, causing a catheter to advance to an individual site in which the distal end of the second catheter or the distal end of the third catheter, which is introduced after the second catheter is withdrawn, is caused to advance near the treatment target of the second lower limb through the inside of the first catheter. In the step of causing a device to advance to an individual site, the individual site treatment device may be caused to advance through the lumen of the second catheter or the third catheter.

As described above, even when the treatment target is present in two lower limbs, it is possible to guide the treatment device near the treatment target by using a third catheter.

Moreover, in the introduction step, a sheath having an outer diameter of equal to or smaller than 2.8 mm may be introduced into a blood vessel of the arm first, and then the catheter assembly may be introduced through the lumen of the sheath.

If the sheath having an outer diameter of 2.8 mm is used as above, a catheter that is quite thick (for example, having an outer diameter of around 2.4 mm) can be used as the first catheter. In the case, for example, a surgeon can use the first catheter having a larger outer diameter. If such a catheter is used, the catheter assembly becomes thick, hence the properties required at the time of delivery can be further improved.

When the treatment target is present in a blood vessel closer to the peripheral side than to the popliteal artery in the lower limb, in the delivery, the distal end of the catheter assembly may be positioned in the femoral artery or the iliac artery, and in the advancement, the treatment device may be sent to the femoral artery from the catheter assembly, and the treatment device may be caused to advance to the popliteal artery. When the elongated catheter assembly is inserted into the blood vessel, a puncture portion of the blood vessel can be prevented from being damaged by abrasion.

As described above, in the treatment method, the distal portion of the catheter assembly is positioned in the femoral artery or the iliac artery during the delivery, and accordingly, the first catheter can assist advance of the treatment device in the device advance step. Moreover, since the outer diameter of the treatment device is smaller than the inner diameter of the first catheter, the treatment device can smoothly advance to the popliteal artery that is relatively meandering much.

Alternatively, when the treatment target is present in a blood vessel closer to the peripheral side than to the popliteal artery in the lower limb, in the delivery step, the distal end of the catheter assembly may be positioned in the popliteal artery or in the blood vessel at the peripheral side.

As described above, the distal end of the catheter assembly is positioned in the popliteal artery or in the blood vessel at the peripheral side, and accordingly, the target treatment which is formed in a portion near the knee, the knee, or the ankle can be excellently treated by the treatment device which will be delivered thereto later.

In this case, it is preferable for the treatment target to be present in a portion near the knee, the calf, or a portion near the ankle.

Even when the treatment target is present in a portion near the knee, the calf, or a portion near the ankle as above, the properties required at the time of delivering the catheter assembly having a double structure can be maintained. Accordingly, the treatment device can be smoothly delivered to the treatment target.

Moreover, the treatment device may be a delivery device by which an intraluminal prosthesis is delivered to and remains in the treatment target, a balloon catheter that dilates the treatment target, or a drug applying device that applies a drug to the treatment target. Examples of the intraluminal prosthesis include a stent. Examples of the drug applying device include a drug eluting balloon catheter and a drug eluting stent.

If the delivery device, balloon catheter, or the drug applying device is used as above, a stenosed portion or an occluded portion formed in a blood vessel of the lower limb can be excellently treated.

When the catheter assembly is in an assembled state, it is preferable for the first catheter and the second catheter to be fixed to each other by a lock mechanism which is disposed in the proximal portion of each of the catheters.

If the first catheter and the second catheter are fixed by the lock mechanism as above, the first catheter and the second catheter can be integrally operated when the catheter assembly is operated. Accordingly, the properties required at the time of delivering the catheter assembly inserted into the blood vessel can be further improved.

Disclosed here is a treatment method for treating a treatment target of at least one lower limb. The treatment method includes a supply step that supplies a catheter assembly in which an inner catheter is disposed in the lumen of an outer catheter, and the distal end of the inner catheter protrudes from the distal end of the outer catheter; a guide wire inserting step in which a guide wire is inserted into the catheter assembly; an introduction step in which the catheter assembly is introduced into a blood vessel of an arm; a delivery step in which a portion of the catheter assembly that is exposed to the outside of the body is operated, and the distal end of the catheter assembly is delivered to a predetermined position of the lower limb through the aorta; an inner catheter withdrawal step in which the inner catheter is withdrawn from the lumen of the outer catheter, in a state where the outer catheter and the guide wire are left inside the blood vessel after the delivery step; a device advance step in which a treatment device for treating the treatment target is introduced into the blood vessel along the guide wire after the inner catheter withdrawal step, and caused to advance to the treatment target through the inside of the outer catheter; and a treatment step in which the treatment target is treated by the treatment device.

According to the above method, by using the catheter assembly composed of two catheters including the inner and outer catheters, a surgeon can smoothly deliver the catheter assembly to a predetermined position of the lower limb along the guide wire in the delivery step. That is, the catheter assembly has a double structure composed of an inner catheter and an outer catheter, and accordingly, properties (kink resistance, torque transmitting properties, operability, and the like) required at the time of delivery are improved. Consequently, even if the catheter assembly is long enough to reach the lower limb from the arm, the surgeon can easily deliver the distal portion of the catheter assembly. Moreover, when the guide wire is introduced into the catheter assembly, a gap between the inner surface of the outer catheter and the outer surface of the guide wire is reduced by the inner catheter. That is, the distal end of the outer catheter inhibits a great step difference from being formed between the inner surface of the outer catheter and the outer surface of the guide wire. Therefore, a concern that the distal end of the catheter assembly may damage the blood vessel in the delivery step can be allayed. As a result, in the treatment method, the outer catheter can be efficiently placed in a predetermined position, and the treatment device can be rapidly and accurately delivered to the treatment target through the inside of the outer catheter, hence excellent treatment can be provided.

In this case, the outer catheter has a tubular outer catheter body, and an outer catheter hub that is disposed in the proximal end of the outer catheter body. The inner catheter has an inner catheter body that can be inserted into the outer catheter body, and an inner catheter hub that is disposed in the proximal end of the inner catheter body and can be connected to the outer catheter hub. In the supply step, the catheter assembly may be constituted by disposing the inner catheter body in an outer catheter lumen of the outer catheter body and connecting the inner catheter hub to the outer catheter hub.

As described above, if the inner catheter hub is connected to the outer catheter hub so as to fix the inner catheter to the outer catheter, the inner catheter and the outer catheter can be integrally operated when the catheter assembly is operated. Accordingly, the properties required at the time of delivering the catheter assembly inserted in to a blood vessel can be further improved.

The inner catheter body has a shaft that extends to the distal end from the inner catheter hub and a tubular body that is disposed in the distal end of the shaft and includes an inner catheter lumen. In the supply step, the catheter assembly may be constituted such that the distal end of the tubular body is disposed closer to the distal side than to the distal end of the outer catheter body, and the proximal end of the tubular body is positioned in the outer catheter lumen of the outer catheter body.

In the catheter assembly constituted as above, the tubular body of the inner catheter is disposed in a predetermined area from a portion, which is closer to the distal side than to the distal end of the outer catheter body, to the proximal end of the outer catheter body. Accordingly, in the guide wire insertion step, in an area from the proximal end of the tubular body to the distal end of the inner catheter hub, the guide wire is disposed to the outside of the lumen of the inner catheter. In other words, in a space between the proximal end of the tubular body and the distal end of the inner catheter hub, the guide wire is disposed in a space between the outer circumferential surface of the shaft and the inner circumferential surface of the outer catheter. That is, the inner catheter is a rapid exchange catheter. Accordingly, in the inner catheter withdrawal step, the guide wire makes a short distance move when passing through the lumen of the inner catheter. As a result, it is possible to easily withdraw the inner catheter from the blood vessel while leaving the guide wire and the outer catheter in the blood vessel.

The tubular body has a second inner catheter lumen that opens in the distal portion and the proximal portion. In the delivery step, a fluid may be injected through the inner catheter hub of the catheter assembly, such that the fluid can be injected into the blood vessel through the second inner catheter lumen.

According to the above embodiment, when a surgeon wants to inject a fluid such as contrast agent, physiological saline, or the like into the blood vessel in the delivery step, even if the guide wire is inserted into the inner catheter lumen of the tubular body, the surgeon can inject the fluid into the blood vessel through the second inner catheter lumen of the tubular body. Accordingly, the surgeon can easily ascertain the shape and the like of the blood vessel by administering, for example, a contrast agent, and as a result, the catheter assembly can be more rapidly delivered to the treatment target.

In the introduction step, a sheath having an outer diameter equal to or smaller than 2.8 mm may be introduced into the blood vessel of the arm first, and then the catheter assembly may be introduced through the lumen of the sheath.

If the sheath having an outer diameter of 2.8 mm is used as above, a catheter that is quite thick (for example, having an outer diameter of around 2.4 mm) can be used as the outer catheter. In the case, for example, a surgeon can use the first catheter having a larger outer diameter. If such a catheter is used, the catheter assembly becomes thick, hence the properties required at the time of delivery can be further improved.

When the treatment target is present in a blood vessel closer to the peripheral side than to the popliteal artery in the lower limb, in the delivery step, the distal end of the catheter assembly may be positioned in femoral artery or iliac artery, and in the device advance step, the treatment device may be sent to the femoral artery from the catheter assembly, and the treatment device may be caused to advance to the popliteal artery. When the long catheter assembly is inserted into the blood vessel, a puncture portion of the blood vessel can be prevented from being damaged by abrasion.

As described above, in the treatment method, the distal portion of the catheter assembly is positioned in the femoral artery or the iliac artery in the delivery step, and accordingly, the outer catheter can assist advance of the treatment device in the device advance step. Moreover, since the outer diameter of the treatment device is smaller than the inner diameter of the outer catheter, the treatment device can smoothly advance to the popliteal artery that is relatively meandering much.

Alternatively, when the treatment target is present in a blood vessel closer to the peripheral side than to the popliteal artery in the lower limb, in the delivery step, the distal end of the catheter assembly may be positioned in the popliteal artery or in the blood vessel at the peripheral side.

As described above, the distal end of the catheter assembly is positioned in the popliteal artery or in the blood vessel at the peripheral side, and accordingly, the treatment target which is formed in a portion near the knee, the knee, or the ankle can be excellently treated by the treatment device which will be delivered thereto later.

In this case, it is preferable for the treatment target to present in a portion near the knee, the calf, or a portion near the ankle.

Even when the treatment target is present in a portion near the knee, the calf, or a portion near the ankle as above, the properties required at the time of delivering the catheter assembly having a double structure can be maintained. Accordingly, the treatment device can be smoothly delivered to the treatment target.

Moreover, the treatment device may be a delivery device by which an intraluminal prosthesis is delivered to and remains in the treatment target, a balloon catheter that dilates the treatment target, or a drug applying device that applies a drug to the treatment target. Examples of the intraluminal prosthesis include a stent. Examples of the drug applying device include a drug eluting balloon catheter and a drug eluting stent.

If the delivery device, balloon catheter, or the drug applying device is used as above, a stenosed portion or an occluded portion formed in a blood vessel of the lower limb can be excellently treated.

The catheter assembly has an outer catheter that has a tubular outer catheter body and an outer catheter hub which is disposed in the proximal end of the outer catheter body; and an inner catheter that has an inner catheter body which can be inserted into the outer catheter body and an inner catheter hub which is disposed in the proximal end of the inner catheter body and has an inner catheter hub lumen formed inside the inner catheter and can be connected to the outer catheter hub. The inner catheter body has a shaft that extends to the distal end from the inner catheter hub, and a tubular body that is disposed in the distal end of the shaft and has an inner catheter lumen which is formed in the inside thereof and opened to the outside in the distal portion and the proximal portion such that a guide wire can be inserted into the tubular body. When the outer catheter hub is connected to the inner catheter hub, the distal end of the tubular body of the inner catheter body is disposed in a position closer to the distal side than to the distal end of the outer catheter body; the proximal end of the tubular body is disposed in a position closer to the proximal end than to the distal end of the outer catheter body; and the proximal end of the tubular body is positioned in the outer catheter lumen of the outer catheter body.

In the catheter assembly constituted as above, when the outer catheter hub is connected to the inner catheter hub, the tubular body of the inner catheter is disposed in a predetermined area from a portion, which is closer to the distal side than to the distal end of the outer catheter, to a portion, which is closer to the proximal side than to the distal end of the outer catheter. Accordingly, when the outer catheter hub is connected to the inner catheter hub, and the guide wire is caused to protrude to the distal end of the inner catheter through the inner catheter hub lumen and the inner catheter lumen in this state, at the distal end of the outer catheter, a step difference formed between the outer surface of the guide wire and the inner surface of the outer catheter becomes small due to the tubular body. Therefore, when being inserted into the body lumen, the catheter assembly of the disclosed here can reduce the strain that is imposed on the body by the distal end of the outer catheter.

Moreover, the catheter assembly is constituted such that the proximal end of the tubular body is positioned in the outer catheter lumen of the outer catheter body. The catheter assembly is also constituted such that the guide wire having been inserted into the inner catheter hub lumen is inserted into the proximal portion of the inner catheter lumen of the tubular body. That is, the guide wire is disposed between the outer circumferential surface of the shaft and the inner circumferential surface of the outer catheter body, and accordingly, in an area from the proximal side of the tubular body to the distal side of the inner catheter hub, the guide wire is positioned outside the lumen of the inner catheter. Therefore, when the guide wire is in the state of being inserted in the catheter assembly, and the inner catheter is withdrawn in this state while leaving the guide wire and the outer catheter behind, the guide wire having been inserted into the inner catheter makes a short distance move when passing through the lumen of the inner catheter. Consequently, it is not necessary to use a long guide wire or lengthen the guide wire, and the guide wire can be easily withdrawn from the body lumen.

When the outer catheter hub is connected to the inner catheter hub, in a cross section of the distal end of the outer catheter body that is orthogonal to the axis of the outer catheter body, it is preferable for the thickness of the tubular body in the radial direction thereof to be greater than the thickness of the outer catheter body in the radial direction thereof. If the above constitution is adopted, the surgeon can reduce the step difference formed between the outer surface of the outer catheter body and the outer surface of the tubular body, while bringing the distal end of the outer catheter into contact with the outer surface of the tubular body. Therefore, damage of body tissue can be suppressed as much as possible. Moreover, when the catheter assembly is inserted into the body lumen, the impact exerted on the distal end of the outer catheter is mitigated due to the thickness of the inner catheter. As a result, a surgeon can insert the outer catheter having a large inner diameter and a small outer diameter (outer catheter that is thin in the radial direction thereof) to a lesion, without kinking the distal end of the outer catheter.

When the outer catheter hub is connected to the inner catheter hub, if a length between the distal end of the tubular body and the distal end of the outer catheter body in the axis direction is made smaller than a length between the distal end of the outer catheter body and the proximal end of the tubular body in the axis direction, the length of the tubular body accommodated inside the outer catheter becomes sufficient, whereby the distal end area of the outer catheter can be prevented from being kinked. Accordingly, when inserting the catheter assembly into the body lumen, a surgeon can more safely inserting it into the body lumen while sufficiently securing pushability or sufficiently transmitting torque to the distal side.

The outer catheter body has a rigidity transition portion in which rigidity is reduced toward the distal end, and a rigidity uniform portion which is disposed in the proximal side of the rigidity transition portion and in which the rigidity is uniform in the axis direction. When the outer catheter hub is connected to the inner catheter hub, if the proximal end of the tubular body is positioned in a portion closer to the proximal side than to the distal end of the rigidity uniform portion, the proximal end of the tubular body is not positioned in the middle of the rigidity transition portion, and transition of rigidity of the outer catheter body can be excellently maintained. Accordingly, when inserting the catheter assembly into the body lumen, a surgeon can more safely insert the catheter assembly into the body lumen while sufficiently securing pushability or sufficiently transmitting torque to the distal side.

If the second inner catheter lumen, which is opened to the outside, is formed in the distal portion and the proximal portion of the tubular body, a liquid such as a contrast agent or physiological saline can be discharged from the distal end of the inner catheter, through the lumen of the outer catheter and the second inner catheter lumen. At this time, the liquid such as a contrast agent or physiological saline injected from the inner catheter hub is supplied through the lumen of the outer catheter having a relatively large inner diameter, until the liquid reaches the second inner catheter lumen. Accordingly, pressure loss is reduced, and for example, even a contrast agent having a high viscosity can be easily pushed out by a weak force. Moreover, while the guide wire is being inserted into the catheter assembly, in the tubular body, a sufficient clearance cannot be formed between the inner circumferential surface of the inner catheter lumen and the outer circumferential surface of the guide wire. Therefore, if the second inner catheter lumen is disposed in the tubular body in the catheter assembly, the liquid such as a contrast agent injected from the inner catheter hub can be excellently discharged from the distal end of the tubular body.

If a shaft lumen which penetrates the shaft in the axis direction is formed in the shaft; if the second inner catheter lumen, which is in communication with the shaft lumen and is opened to the outside in the distal portion, is formed in the tubular body; and if a second inner catheter hub lumen, which is in communication with the shaft lumen and is opened to the outside, is formed in the inner catheter hub, a liquid such as a contrast agent or physiological saline can be discharged from the distal end of the inner catheter through the shaft lumen and the second catheter lumen. At this time, the liquid can be effectively delivered without coming into contact with the guide wire and being interrupted by the guide wire.

If the shaft is connected to the inner catheter hub in a position different from the position of the inner catheter hub lumen, a liquid can be easily supplied into the lumen of the outer catheter through the inner catheter hub lumen, in a state where the outer catheter hub is being connected to the inner catheter hub.

If the inner catheter can be inserted into the tubular outer catheter body of the outer catheter and has an inner catheter hub in which an inner catheter hub lumen opened to the outside in the distal portion and the proximal portion is formed; a shaft which is connected to the inner catheter hub and extends to the distal end from the inner catheter hub; and a tubular body which is disposed in the distal end of the shaft and in which an inner catheter lumen opened to the outside in the distal portion and the proximal portion so as to enable a guide wire to be inserted into the lumen is formed, a liquid can be supplied into the lumen of the outer catheter through the inner catheter hub lumen, in a state where the inner catheter is being inserted into the outer catheter body.

If the inner catheter hub can be connected to the outer catheter hub disposed in the proximal end of the outer catheter body, a state where the inner catheter is being inserted into the outer catheter body can be excellently maintained. Accordingly, operability is improved, and a liquid can be supplied into the lumen of the outer catheter through the inner catheter hub lumen.

When a lower limb is treated by an intervention procedure in which a catheter is introduced from an arm, the catheter can be easily delivered to a treatment target, and excellent treatment can be provided.

BRIEF DESCRIPTION OF THE DRAWINGS

FIG. 9A is a first illustrative view showing a treatment method according to a second embodiment representing another example of the treatment method disclosed here, and FIG. 9B is a second illustrative view of the treatment method following FIG. 9A.

FIG. 10A is a third illustrative view of the treatment method following FIG. 9B, and FIG. 10B is a fourth illustrative view of the treatment method following FIG. 10A.

FIG. 11A is a first illustrative view showing a treatment method according to a sixth modified example; FIG. 11B is a second illustrative view of the treatment method following FIG. 11A; and FIG. 11C is a third illustrative view of the treatment method following FIG. 11B.

FIG. 13A is a plan view showing an outer catheter of the catheter assembly shown in FIG. 12, and FIG. 13B is a plan view showing an inner catheter of the catheter assembly shown in FIG. 12.

DETAILED DESCRIPTION

Figure 1:
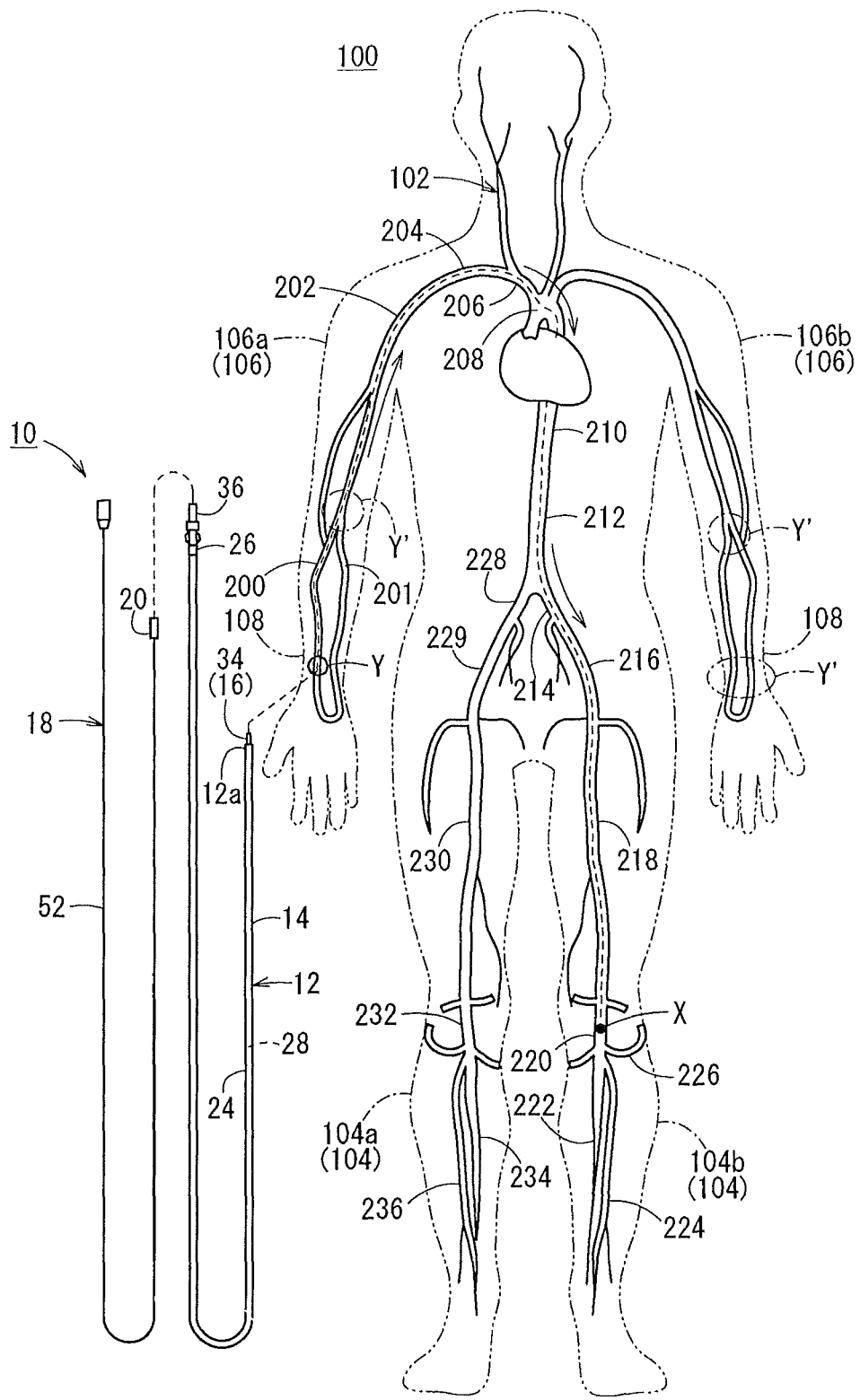
FIG. 1 is a schematic illustration of one embodiment of a treatment method representing one example of the treatment method disclosed here.

Set forth below with reference to the drawing figures is a detailed description of embodiments of a treatment method representing examples of the treatment method disclosed here.

A treatment method according to a first embodiment is an intervention procedure that provides treatment inside a blood vessel 102 of a patient 100 as shown in FIG. 1. This procedure provides treatment of a lesion formed in the blood vessel 102 of a lower limb 104. Examples of the treatment target include a stenosed portion X that is formed when thrombi and the like are accumulated in the popliteal artery. In the following description, between a pair of lower limbs 104 (a left leg 104b: a first lower limb, a right leg 104a: a second lower limb) of the patient 100, the stenosed portion X formed in the left leg 104b will be treated.

In the treatment method, an intervention device 10 is introduced from the blood vessel 102 of an arm 106 (upper limb), and the distal portion of the intervention device 10 is delivered to the stenosed portion X to provide treatment. Therefore, the full length of the intervention device 10 is sufficiently longer than that of a device used for, for example, percutaneous transluminal coronary angioplasty.

The intervention device 10 used for the treatment method includes a catheter assembly 12 that includes double catheters (an outer catheter 14 and an inner catheter 16) and a treatment device 18 that treats the stenosed portion X. The catheter assembly 12 (hereinafter, simply referred to as "assembly 12") is a so-called guiding catheter. The catheter assembly 12 is introduced into the blood vessel 102 of the patient 100 first and then guides the treatment device 18 introduced after the catheter assembly 12. The treatment device 18 has a treatment portion 20 for providing treatment in the distal portion of the treatment device 18. The treatment portion 20 advances to the stenosed portion X through the assembly 12.

In order to facilitate understanding of the treatment method according to the first embodiment, the process of the procedure will first be schematically described. In the treatment method, an introduction step is first performed in which the assembly 12 is introduced into the blood vessel 102 of the arm 106 of the patient 100. In the introduction step, for example, a sheath introducer 22 (see FIGS. 2 and 3) is inserted into a right radial artery 200 present in a wrist 108 of a right arm 106a, and the assembly 12 is introduced through the sheath introducer 22.

Next, a delivery step is performed in which the proximal side of the assembly 12 (portion of the assembly 12 exposed outside the body) is operated to deliver a distal portion 12a of the assembly 12 to a predetermined position of the lower limb 104 through the blood vessel 102 in the body. When the distal portion 12a of the assembly 12 is introduced into the right radial artery 200 of the right arm 106a, in the delivery step, the distal portion 12a is advanced along the right radial artery 200, a right brachial artery 202, a right subclavian artery 204, and a brachiocephalic artery 206. Thereafter, the distal portion 12a is delivered in order of an aortic arch 208, a thoracic aorta 210, an abdominal aorta 212, a left common iliac artery 214, a left external iliac artery 216, and a left femoral artery 218.

After the delivery step, a pull-out step is performed in which the inner catheter 16 is pulled out of the outer catheter 14. That is, the inner catheter 16 is pulled out by being moved backward (proximal direction) while the outer catheter 14 is fixed or remains in position, and the outer catheter 14 is left inside the body of the patient 100.

After the inner catheter 16 is pulled out, a device advance step is performed in which the treatment portion 20 of the treatment device 18 is advanced through the inside of the outer catheter 14. A surgeon inserts the distal end of the treatment device 18 into the proximal end of the lumen in the outer catheter 14 and then advances the treatment device 18 in the forward direction to deliver the treatment portion 20 of the treatment device 18 from a distal opening 28a of the outer catheter 14, toward the stenosed portion X of a left popliteal artery 220 from the left femoral artery 218.

Thereafter, a treatment step in which the stenosed portion X is treated by the treatment portion 20 of the treatment device 18 is performed. After the treatment step, the outer catheter 14 and the treatment device 18 are pulled out of the body of the patient 100 to end the intervention procedure.

Figure 2:
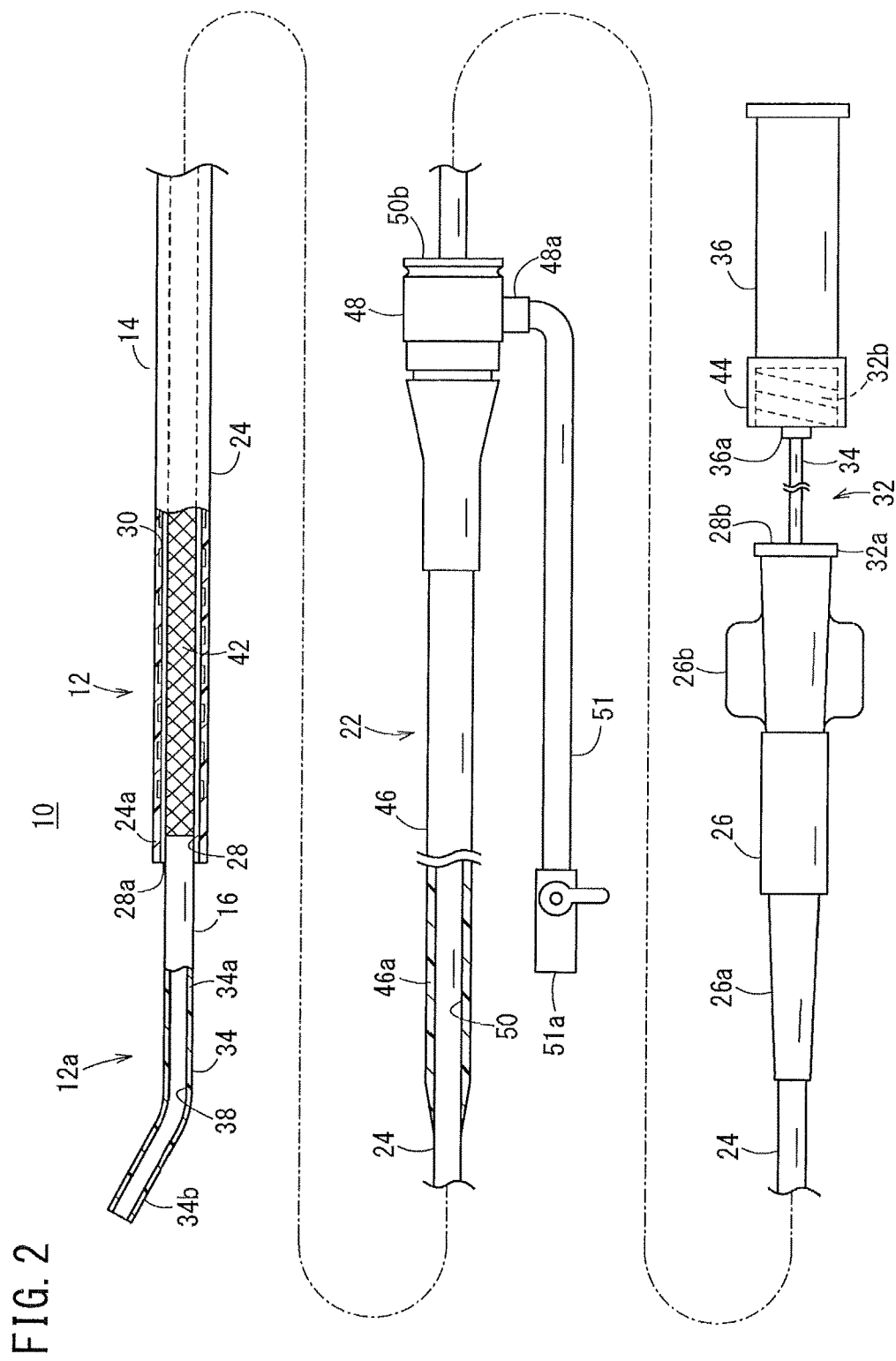
FIG. 2 is a partial lateral cross-sectional exploded view of a catheter assembly and a sheath introducer used in the treatment method according to the first embodiment.

Next, the assembly 12 used for the treatment method and the sheath introducer 22 used in the introduction step will be described in detail with reference to FIG. 2.

As described above, the assembly 12 is configured such that the outer catheter 14 (first catheter) and the inner catheter 16 (second catheter) are layered on each other or axially overlap one another. The outer catheter 14 includes an outer shaft 24 that is in the form of a long (elongated) flexible tube and an outer catheter hub 26 that is disposed at the proximal side or end of the outer shaft 24. The outer catheter hub 26 is connected to the outer shaft 24.

The inside of the outer shaft 24 and the outer catheter hub 26 are penetrated by an insertion lumen 28 (lumen) that is formed in the axis direction. That is, the insertion lumen 28 extends axially through the outer catheter hub 26 and the outer shaft 24. The insertion lumen 28 is connected to or opens to the distal opening 28a in the distal end of the outer shaft 24 and to a proximal opening 28b in the proximal end of the outer catheter hub 26. The inner catheter 16 is inserted into and positioned in the insertion lumen 28.

The outer shaft 24 is configured such that the insertion lumen 28 has a relatively large inner diameter. The outer diameter of the outer shaft 24 is about the same as the outer diameter of the conventional guiding catheter introduced from the right radial artery 200. For example, the outer diameter of the outer shaft 24 is about 2.33 mm to 2.4 mm (7 Fr:1 Fr is equal to ⅓ mm). The inner diameter of the insertion lumen 28 is, for example, equal to or smaller than 2.2 mm, though the inner diameter depends on the outer diameter of the inner catheter 16 or the treatment device 18. That is, the outer shaft 24 has a thin wall portion 24a that surrounds the insertion lumen 28.

Moreover, a reinforcing wire 30 is embedded inside the wall portion 24a to improve kink resistance, torque-transmitting properties, and operability of the outer shaft 24. The reinforcing wire 30 is configured as a braid or a coil. The reinforcing wire 30 is in the form of a thin plate-like band and wound in a coil (or a mesh) along the circumferential direction of the wall portion 24a. The reinforcing wire 30 extends from a position, which is separated or spaced from the distal end of the outer shaft 24 at a predetermined interval or distance, to a connection site of the outer catheter hub 26, and reinforces the entire outer shaft 24. Examples of the material constituting the reinforcing wire 30 include metals such as Ni—Ti-based alloys and stainless steel (all kinds of SUS), hard polymers such as polyolefin, liquid crystal polymers, and the like.

It is preferable for the full length of the outer shaft 24 to be, for example, equal to or greater than 150 cm, such that the distal end of the outer shaft 24 reaches the left femoral artery 218, although the full length varies with the body size of the patient 100. The outer catheter hub 26 is firmly connected to the proximal portion of the outer shaft 24 such that a surgeon can reliably operate the outer shaft 24 using the outer catheter hub 26.

The outer catheter hub 26 has a diameter larger than that of the outer shaft 24 such that the surgeon can relatively easily grip the hub. A strain relief 26a, which is configured to reduce a load applied to the portion in which the outer catheter hub 26 is connected to the outer shaft 24, is disposed in the distal portion of the outer catheter hub 26. Moreover, a pair of wings 26b for improving operability for the surgeon is disposed on the outer circumferential surface of the outer catheter hub 26.

A bump or enlargement 32a forming one side of a lock mechanism 32 of the assembly 12 is located at the proximal portion of the outer catheter hub 26. The bump 32a protrudes in the circumferential direction of the outer circumferential surface of the outer catheter hub 26, and is pushed into (mates with) a screw-like groove 32b of an inner catheter hub 36 which will be described later. The enlargement 32a and the screw-like groove 32b together form a luer lock.

Similar to the outer catheter 14, the inner catheter 16 includes an inner shaft 34 that is in the form of a long (elongated) flexible tube and an inner catheter hub 36 that is disposed at the proximal side of the inner shaft 34. The inner catheter hub 36 is connected to the inner shaft 34. The inside of the inner shaft 34 and the inner catheter hub 36 is penetrated by a guide wire lumen 38 that is formed along the axis direction. That is, the guide wire lumen 38 extends axially through the inner shaft 34 and the inner catheter hub 36. A guide wire 40 (see for example FIG. 3) is inserted into the guide wire lumen 38. In a state where the assembly 12 has been established, the guide wire lumen 38 constitutes the lumen of the assembly 12. Accordingly, it is preferable to configure the guide wire lumen 38 to have such a size that the guide wire 40 can slide inside the guide wire lumen 38 and the guide wire lumen 38 is not perfused with the blood (body fluid) flowing in a blood vessel.

The full length of the inner shaft 34 is larger than the full length of the outer shaft 24. Accordingly, in a state where the inner shaft 34 is connected to the assembly 12, and the proximal portion of the inner shaft 34 is exposed from the proximal opening 28b of the outer catheter hub 26, the inner shaft 34 can be exposed from the distal opening 28a of the outer shaft 24 (i.e., the distal end portion of the inner shaft 34 extends distally beyond the distal end of the outer shaft 24 as shown in FIG. 2).

An angled or turned distal end portion 34b, which is angled or turns to make it easier to guide the direction and the like of the assembly 12 during the delivery step, is provided at the distal end of the inner shaft 34. That is, the distal end portion of the inner shaft 34 is angled relative to the immediately adjoining portion of the inner shaft 34 as shown in FIG. 2 so that the central axis of the angled portion 34b is disposed at an angle other than 0° and 180° with respect to the axis of the portion of the inner shaft 34 immediately adjoining the angled portion 34b. It is preferable for the outer circumferential surface of the angled or turned distal end portion 34b to be coated with a hydrophilic polymer such that the inner shaft 34 can excellently slide inside the blood vessel 102 (see FIG. 3). Moreover, it is preferable for a reinforcing wire (braid) 42 for reinforcing the inner shaft 34 to be embedded in a wall portion 34a of the inner shaft 34 that is separated (spaced) from the angled or turned distal end portion 34b of the inner shaft 34 at a predetermined interval or predetermined distance.

When the inner diameter of the insertion lumen 28 is about 2.2 mm, the outer diameter of the inner shaft 34 is preferably, for example, about 2.1 mm (6 Fr), even though the outer diameter also depends on the inner diameter of the insertion lumen 28 of the outer shaft 24. Moreover, when the inner diameter of the insertion lumen 28 is about, for example, 1.7 mm, the outer diameter of the inner shaft 34 is preferably about 1.5 mm to 1.6 mm (5 Fr).

It is preferable for the outer shaft 24 or the inner shaft 34 to have rigidity and flexibility such that the shaft can rather excellently move forward and backward inside the meandering blood vessel 102 during the delivery step. Examples of materials constituting the outer shaft 24 or the inner shaft 34 include resins and metals. Examples of the resins include polymer materials such as polyolefin (for example, polyethylene, polypropylene, polybutene, an ethylene-propylene copolymer, an ethylene-vinyl acetate copolymer, an ionomer, a mixture composed of two or more kinds of these, and the like), polyvinyl chloride, polyamide, a polyamide elastomer, polyester, a polyester elastomer, polyurethane, a polyurethane elastomer, polyimide, and a fluororesin, a mixture of these, and a combination of two or more kinds of the above polymer materials. Examples of the metals include pseudoplastic alloys (including super elastic alloys) such as Ni—Ti-based alloys, shape-memory alloys, stainless steel (for example, all kinds of SUS such as SUS304, SUS303, SUS316, SUS316L, SUS316J1, SUS316J1L, SUS405, SUS430, SUS434, SUS444, SUS429, SUS430F, and SUS302), cobalt-based alloys, noble metals such as gold, platinum, tungsten-based alloys, carbon-based materials (including a piano wire), and the like. It is also possible to use a complex or combination of the resins or metals (for example, a multilayer tube obtained by lamination, and the like). Moreover, a radiopaque maker that can be confirmed by radiography may be placed in a portion near the distal end of the outer shaft 24 or the inner shaft 34.

The inner catheter hub 36 connected to the inner shaft 34 is in the form of a cylinder having an outer diameter which is almost the same as that of the outer catheter hub 26. A connector cylinder portion 44, which surrounds the periphery of a connection projection 36a connected to the inner shaft 34, is disposed in the distal portion of the inner catheter hub 36. The connector cylinder portion 44 forms the other side of the lock mechanism 32. On the inner circumferential surface of the connector cylinder portion 44, the screw-like or helical groove 32b into which the bump 32a of the outer catheter hub 26 is screwed is formed.

That is, in the assembly 12, the proximal portion of the outer catheter hub 26 is connected and fixed to (locked with) the distal portion of the inner catheter hub 36 by the lock mechanism 32, whereby a single operation portion that can operate two catheters can be performed. A surgeon grips the outer catheter hub 26 or the inner catheter hub 36 and optionally performs an advance and retreat operation or a rotation operation. In this way, the surgeon can integrally perform the advance and retreat operation or the rotation operation of the outer shaft 24 or the inner shaft 34. By rotating the inner catheter hub 36 relative to the outer catheter hub 26, the lock mechanism 32 can be comparatively easily separated (released).

Before the introduction step is performed, the assembly 12 is established in a state where the inner catheter 16 is inserted into (positioned inside) the insertion lumen 28 of the outer catheter 14, and movement of both the catheters in the axial direction is restricted by the lock mechanism 32. In the introduction step, the assembly 12 is inserted into the wrist 108 of the patient 100 through the sheath introducer 22.

The sheath introducer 22 includes a flexible tubular sheath 46 and an introducer hub 48 which is connected to the proximal portion of the sheath 46. The inside of both the sheath 46 and the introducer hub 48 is penetrated by a guiding lumen 50 that extends along the axial direction. That is, the guiding lumen 50 passes through both the sheath 46 and the introducer hub 48. The guiding lumen 50 is connected to (opens to) a distal opening 50a (see FIG. 3) at the distal end of the sheath 46 and to a proximal opening 50b at the proximal end of the introducer hub 48. A dilator is first introduced into the guiding lumen 50 to make a puncture in the wrist 108 of the patient 100. After the dilator is withdrawn, the assembly 12 is inserted into the guiding lumen 50 of the sheath introducer 22.

The sheath 46 is inserted into the right radial artery 200 in the introduction step so as to promote introduction of the assembly 12. The full length of the sheath 46 is shorter than that of the outer shaft 24 or the inner shaft 34, and is about, for example, 10 cm to 30 cm. Moreover, the outer diameter of the sheath 46 is about, for example, 2.7 mm (8 Fr), that is, equal to or smaller than 2.8 mm, such that it can be inserted into the right radial artery 200 having a vessel diameter of about 2.9 mm±0.6 mm.

The material constituting the sheath 46 is not particularly limited, and for example, it is possible to use a polymer composition containing a crystalline polymer, such as polyether ether ketone (PEEK), polyether ketone (PEK), polyether ketone ketone (PEKK), polyether ether keton ketone (PEEKK), polyphenylene sulfide (PPS), polyether sulfone (PES), polysulfone (PSF), polyimide (PI), polyether imide (PEI), and amorphous polyarylate (PAR). Other resin materials may also be used, and for example, an ethylene tetrafluoroethylene (ETFE) copolymer is suitable for making a thin sheath 46, since it has excellent strength and is easily processed.

Therefore, a wall portion 46a of the sheath 46 constituting the guiding lumen 50 is thin wall portion having a thickness of about 0.1 mm to 0.15 mm for instance. Consequently, the inner diameter of the guiding lumen 50 can be increased, and as the outer catheter 14 (assembly 12), a sufficiently thick catheter (7 Fr) can be used according to the size of the guiding lumen 50. The distal end of the sheath 46 is tapered to the tip, and accordingly, a step difference formed between the sheath 46 and the assembly 12 or the dilator sent from the distal opening 50a can be reduced.

The introducer hub 48 has a diameter that is larger than that of the sheath 46, so as to make it easy for a surgeon to grip the hub and to facilitate introduction of the assembly 12. A port 48a that is in communication with the guiding lumen 50 is located on the lateral circumferential surface of the introducer hub 48. The port 48a is connected to a tube 51 having a connector 51a (three-way cock) that is widely used. The sheath introducer 22 can guide a liquid such as physiological saline to the guiding lumen 50 through the connector 51a. It is preferable for the guiding lumen 50 of the introducer hub 48 to be provided with a valve for preventing leakage of the blood to the outside.

The assembly 12 and the sheath introducer 22 of the intervention device 10 are configured, by way of example, in the manner described above. In the treatment device 18 of the intervention device 10 shown in FIG. 1, the full length of a treatment device side shaft 52 that is inserted into the outer shaft 24 is long. Except for this point, a known device can be used as the treatment device 18. For example, the treatment portion 20 disposed in the distal portion of the treatment device side shaft 52 of the treatment device 18 has a stent 54 that will remain in the stenosed portion X and a balloon 56 that can be dilated or expanded inside the stent 54 (see FIG. 5C). That is, this example of the treatment device 18 is configured as a stent delivery device that can cause the stent 54 to dilate and remain in the stenosed portion X. The stent is an example of an intraluminal prosthesis.

Referring to the intervention device 10 configured by way of example in the manner described above, a treatment method according to a first embodiment will be described in detail.

In the following description, a treatment method for treating the aforementioned stenosed portion X of the left popliteal artery 220 of the left leg 104b will be explained in detail. But the treatment target of the treatment method is not particularly limited. For example, arteries such as the left femoral artery 218, a left anterior tibial artery 222, and a left posterior tibial artery 224 or a peripheral blood vessel 226 connected to an artery may be the treatment site. Alternatively, in addition to arteries, veins may also be treated. Furthermore, blood vessels of the right leg 104a (a right femoral artery 230, a right popliteal artery 232, a right anterior tibial artery 234, a right posterior tibial artery 236, and the like) may also be treated. To summarize, the treatment site can include various lumens in the lower limb 104. Moreover, in addition to the stenosed portion X, various diseases that can be treated by the treatment device 18 in an intervention procedure, such as occluded portions and damage or aneurysm of blood vessels, can be the lesion as a treatment target.

Before implementing the treatment method, a surgeon determines in advance an introduction portion Y of the blood vessel 102 of the arm 106, and prepares the intervention device 10 (the assembly 12, the treatment device 18, and the guide wire 40) having a length appropriate for the introduction portion Y.

Herein, a case where the wrist 108 (right radial artery 200) of the right arm 106a is selected as the introduction portion Y will be described. However, the introduction portion Y is not limited to this site. For example, instead of the right radial artery 200, a right ulnar artery 201 in the wrist 108 of the right arm 106a may be selected. When the wrist 108 (the right radial artery 200 or the right ulnar artery 201) is selected as the introduction portion Y, it is possible to obtain advantages of being able to bend an elbow after the treatment, to rather easily arrest hemorrhage, to shorten a resting period, and the like.

As shown in FIG. 1, a portion near the elbow of the right arm 106a may be selected as an introduction portion Y', and the assembly 12 is directly introduced into the right brachial artery 202. The right brachial artery 202 is connected to the right radial artery 200 and the right ulnar artery 201. For this reason, the vessel diameter of the right brachial artery 202 is larger than that of the right radial artery 200 and the like, hence the assembly 12 or the sheath introducer 22 having a larger diameter can be inserted into the right brachial artery 202. Moreover, in consideration of the better arm and the like of the patient 100, the introduction portion Y' may be set in the wrist 108 (left radial artery or left ulnar artery) or a portion near the elbow (left brachial artery) of the left arm 106b. To summarize, the introduction portions Y and Y' of the intervention device 10 may be optionally set in an appropriate site in both arms, in consideration of delivery of the assembly 12 to the stenosed portion X, postoperative care for the patient 100, and the like.

After selecting an assembly 12 that is appropriate for the determined introduction portion Y, a surgeon inserts the inner catheter 16 into the insertion lumen 28 of the outer catheter 14, and assembles the assembly 12 such that the angled or turned distal end portion 34b of the inner catheter 16 protrudes from (beyond) the distal opening 28a of the outer catheter 14. That is, the assembly 12 is configured with two catheters in which the axial center of the insertion lumen 28 and the axial center of the guide wire lumen 38 are in an approximately coaxial position (supply step). At this time, the screw-like groove 32b of the inner catheter hub 36 and the bump 32a of the outer catheter hub 26 are screwed together (locked with each other), whereby the assembled state of the assembly 12 is maintained. The assembly 12 may be assembled in advance when it is supplied as a product.

Figure 3:
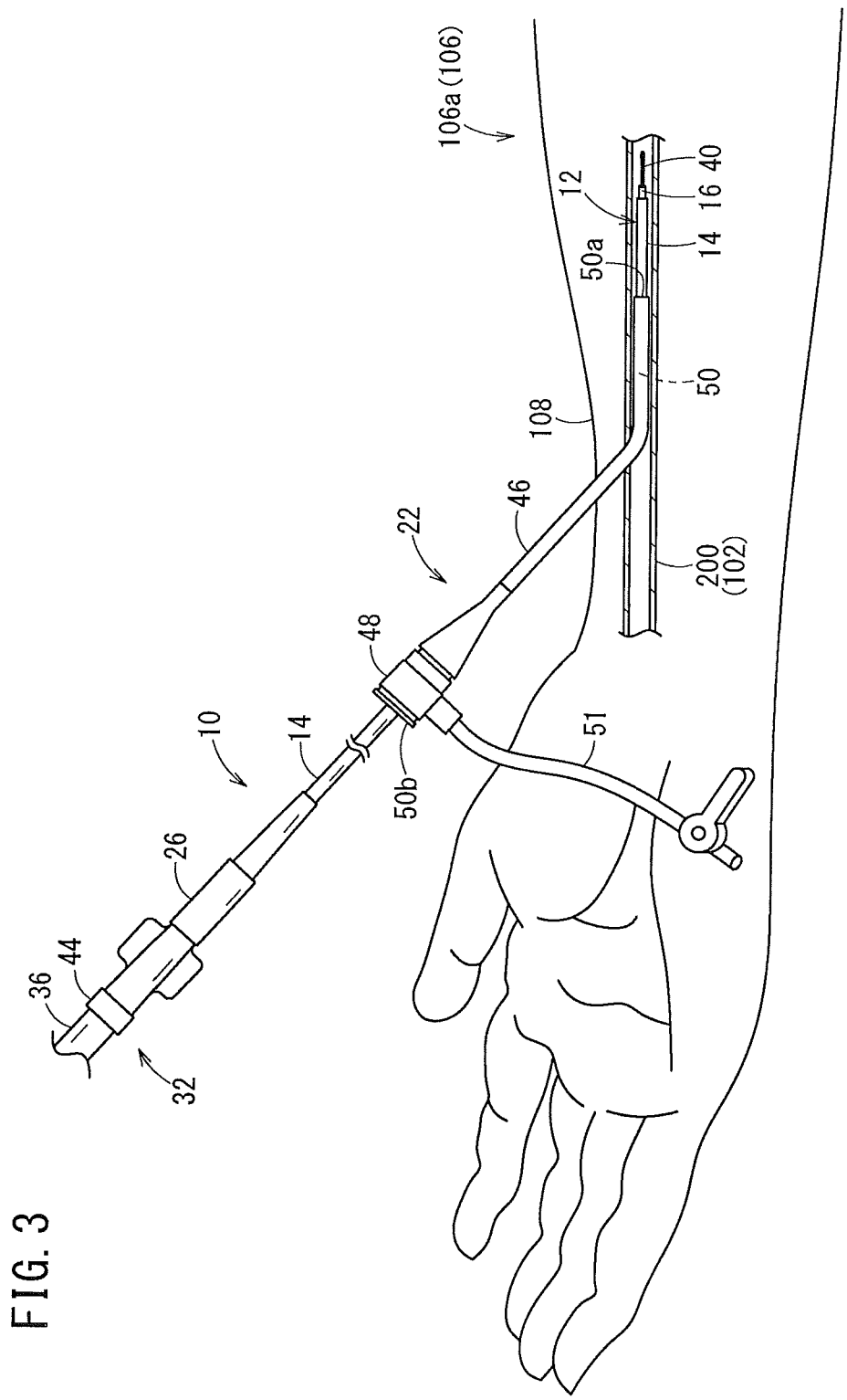
FIG. 3 is a first illustrative view showing the state of the catheter assembly introduced by the treatment method according to the first embodiment.

In the introduction step, the surgeon locates the right radial artery 200 on the wrist 108 of the right arm 106a, and inserts the guide wire 40 into the artery by making a puncture or an incision in the right radial artery 200 by a known technique such as Seldinger technique. That is, as shown in FIG. 3, in a state where a hand is held palm up, the guide wire 40 is inserted into the right radial artery 200, and a dilator of the sheath introducer 22 is inserted into the artery along the guide wire 40. The outer circumferential surface of the dilator is covered by the sheath 46 of the sheath introducer 22. When the dilator is inserted, the sheath 46 is also inserted into the right radial artery 200 together with the dilator. As described above, the diameter of the sheath 46 is smaller than the vessel diameter of the right radial artery 200. Accordingly, the sheath 46 can relatively easily advance into the right radial artery 200.

After causing the distal portion of the sheath 46 to advance by a predetermined distance to the central side (anatomically-based) terms of the right radial artery 200, the surgeon pulls out the dilator, and inserts the assembly 12 into the artery from the proximal opening 50b of the introducer hub 48. At this time, the surgeon inserts the guide wire 40, which has already been inserted into the guide wire lumen 38 of the inner catheter 16, into the artery so as to cause the assembly 12 to advance along the guide wire 40. Since the wall portion 46a of the sheath 46 is thin, the guiding lumen 50 has an inner diameter that can rather easily assist the advance (sliding) of the assembly 12 (outer catheter 14). That is, the assembly 12 is smoothly sent from (advanced beyond) the distal opening 50a of the sheath 46 and advances inside the right radial artery 200.

As shown in FIG. 1, the surgeon causes the assembly 12 to advance along the guide wire 40 ahead, in the delivery step. At this time, while checking the state of the distal portion 12a of the assembly 12 shown in a radiographic image obtained by radiography, the surgeon grips and operates the proximal side (proximal end portion) of the assembly 12 exposed from the introducer hub 48. As a result, a distal portion 12a of the assembly 12 moves into the right brachial artery 202 from the right radial artery 200, makes an advance along the right subclavian artery 204 as if making a curve or turn, and advances into the aorta (aortic arc 208) through the brachiocephalic artery 206.

Figure 4A:
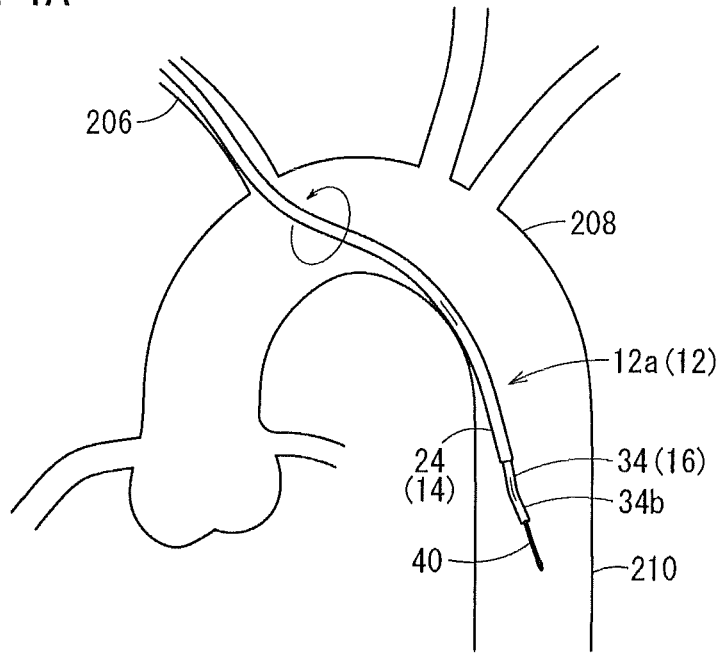
FIG. 4A is a second illustrative view showing the way the distal portion of the catheter assembly operates by the treatment method according to the first embodiment.

After the distal portion 12a of the assembly 12 advances into the aortic arc 208, the surgeon rotates the proximal side of the assembly 12 under radiography, and moves the distal portion 12a of the assembly 12 to the thoracic aorta 210. Since the angled or turned distal end portion 34b of the inner catheter 16 forms a slope or angle with respect to the axial direction of the assembly 12, the distal portion 12a of the assembly 12 having advanced from the brachiocephalic artery 206 can be relatively easily brought close to the thoracic aorta 210 as shown in FIG. 4A.

Figure 4B:
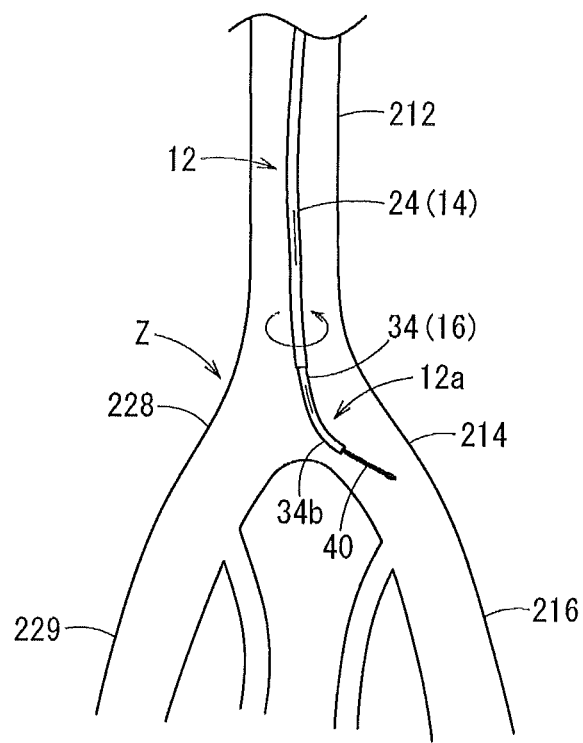
FIG. 4B is a third illustrative view showing the way the distal portion of the catheter assembly operates by the treatment method following FIG. 4A.

While the distal portion 12a of the assembly 12 is moving toward the thoracic aorta 210, the surgeon further pushes the proximal side (end) of the assembly 12. As a result, the distal portion 12a of the assembly 12 moves from the central side to the peripheral side along the aorta (the thoracic aorta 210 and the abdominal aorta 212), and reaches a connection position Z between a right common iliac artery 228 and the left common iliac artery 214 at the peripheral side of the abdominal aorta 212. As shown in FIG. 4B, even in this connection position Z, if the proximal side of the assembly 12 is rotated, the angled or turned distal end portion 34b can be moved in a desired direction (left common iliac artery 214). Thereafter, by pushing (forwardly moving) the proximal side of the assembly 12, the surgeon causes the distal portion 12a of the assembly 12 to advance to the left external iliac artery 216 and the left femoral artery 218 from the left common iliac artery 214.

When a full length catheter which is simply lengthened is inserted from the arm 106 and caused to advance to the blood vessel 102 of the lower limb 104, most of the catheter is inserted into the body, and so the operability of the catheter deteriorates. That is, even if the proximal side of the catheter that is exposed outside the body is operated, the outer circumferential surface of the catheter comes into contact with, for example, the blood vessel 102. Accordingly, the operating force is not easily transmitted to the distal portion, and this can cause great difficulty in delivering the catheter to the lower limb 104.

In contrast, using the assembly 12 constituted with double catheters (two catheters) as described in the treatment method according to the first embodiment, the distal portion 12a of the assembly 12 can be more easily delivered to the blood vessel 102 of the lower limb 104. That is, in the assembly 12, the inner catheter 16 accommodated in the insertion lumen 28 of the outer catheter 14 reinforces the entire assembly 12. Accordingly, for example, even when the outer catheter 14 is pressed by the blood vessel 102, the inner catheter 16 can excellently support the outer catheter 14.

Particularly, with the assembly 12 disclosed here, even when a relatively strong frictional force is applied to the outer catheter 14 from the blood vessel 102, the outer circumferential surface of the inner catheter 16 comes into contact with the wall portion 34a of the outer catheter 14 with a strong frictional force when the catheter is rotated. Therefore, in addition to the torque of the outer catheter 14, the torque of the inner catheter 16 is also transmitted, whereby rotation of the entire assembly 12 is promoted. As a result, in the assembly 12, torque is transmitted to the distal portion 12a to a higher degree.

Alternatively, when it is desired to change the course of the assembly 12, the surgeon may rotate only the inner catheter 16 without also rotating the outer catheter 14. In this manner, the angled or turned distal end portion 34b of the inner catheter 16 rotated relative to the fixed outer catheter 14 moves in a desired direction. As a result, the properties required at the time of delivering the assembly 12 are further improved.

Figure 5A:
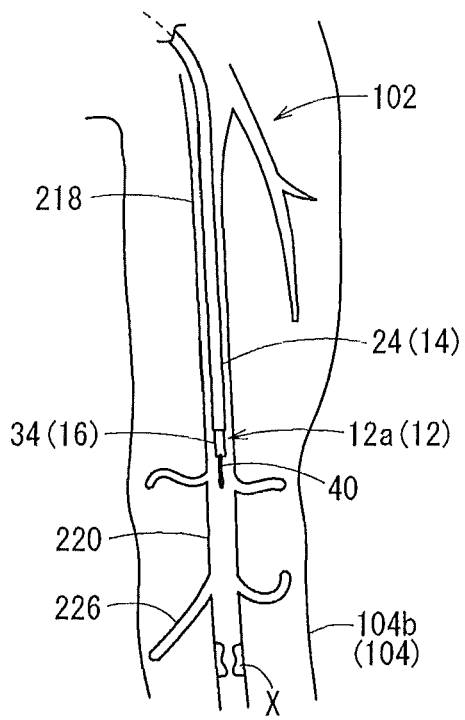
FIG. 5A is a fourth illustrative view of the treatment method following FIG. 4B.

As shown in FIG. 5A, in the delivery step, the distal portion 12a of the assembly 12 is delivered to a predetermined position (position near the portion above the left popliteal artery 220) of the left femoral artery 218, and delivery of the assembly 12 is then stopped. The left popliteal artery 220 has a vessel diameter smaller than that of the left femoral artery 218 and meanders quite a lot. Accordingly, if the assembly 12 is stopped in the left femoral artery 218, it is possible to prevent the blood vessel 102 from applying a heavy load to the outer catheter 14.

The point in time when the delivery step is stopped (the position where the distal portion 12a of the assembly 12 is stopped) is not particularly limited, and may be optionally changed by the surgeon in the middle of the procedure, according to the treatment condition or treatment target. For example, in the delivery step, the distal portion 12a of the assembly 12 may be delivered to a portion near the knee of the patient 100 (for example, the popliteal artery), portion below the patient's knee (for example, the anterior tibial artery or the posterior tibial artery), or the patient's ankle (the fibular artery or the dorsalis pedis artery). If the distal portion 12a is delivered to the above position, the treatment target formed in the portion near the patient's knee, the portion below the patient's knee or ankle can be excellently treated by the treatment device 18 which will be delivered thereto later. Moreover, depending on the treatment target, for example, the distal portion 12a of the assembly 12 may be stopped at the iliac artery (the left common iliac artery 214 or the left external iliac artery 216). That is, in the present specification, the "blood vessel of lower limb" also includes the blood vessels (the iliac artery and the like) closer to the peripheral side than to the abdominal aorta 212.

Figure 5B:
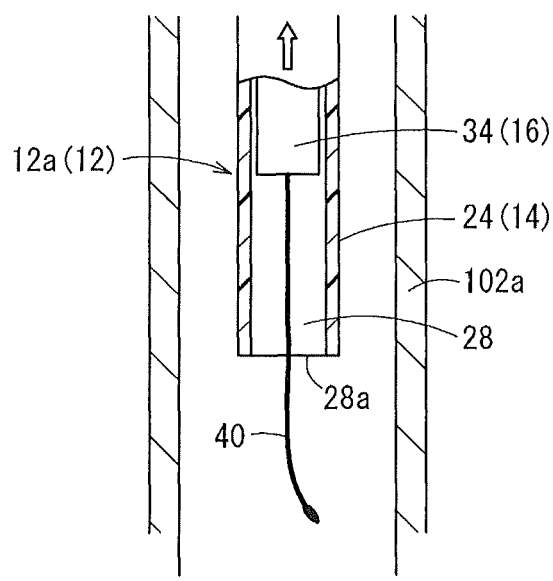
FIG. 5B is a fifth illustrative view of the treatment method following FIG. 5A.

In the pull-out step performed after the delivery step, the inner catheter hub 36, having been connected to the outer catheter hub 26 by the lock mechanism 32, is unlocked. That is, the two catheters constituting the assembly 12 are disassembled. Thereafter, as shown in FIG. 5B, the position of the outer catheter 14 and the guide wire 40 in the axial direction with respect to the left femoral artery 218 is fixed, and only the inner catheter 16 is caused to retreat or move rearwardly so that the inner catheter is removed from the outer catheter and the patient. As a result, only the outer catheter 14 is left in the body of the patient 100. As described above, in the outer catheter 14, the reinforcing wire 30 is embedded in the wall portion 24a of the outer shaft 24 so as to reinforce the shaft. Therefore, even after the pull-out step, the outer catheter 14 can maintain the insertion lumen 28 in an excellent state.

Figure 5C:
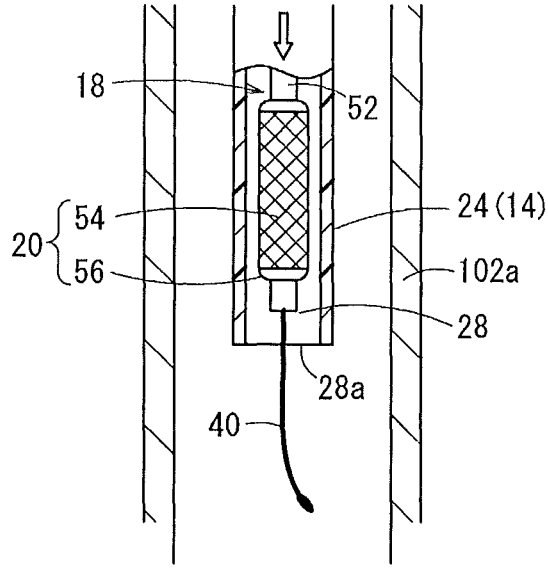
FIG. 5C is a sixth illustrative view of the treatment method following FIG. 5B.

In the device advance step performed after the pull-out step, the surgeon inserts the distal end of the treatment device 18 (stent delivery device) into the proximal opening 28b of the outer catheter 14. At this time, the surgeon inserts the guide wire 40 into the treatment device 18, and causes the treatment device 18 to advance along the insertion lumen 28 of the outer catheter 14 and the guide wire 40. As a result, the treatment portion 20 of the treatment device 18 is delivered to the distal side (end) of the outer catheter 14 as shown in FIG. 5C.

Figure 5D:
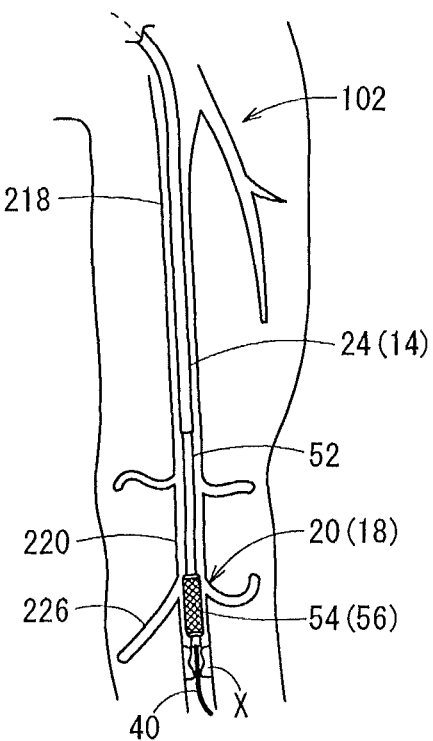
FIG. 5D is a seventh illustrative view of the treatment method following FIG. 5C.

As shown in FIG. 5D, after the treatment portion 20 is sent (moved) to the left femoral artery 218 after moving beyond the distal opening 28a of the outer catheter 14, the surgeon continues to advance the treatment portion 20. The shaft 52 at the treatment device side moves under the guidance of the outer shaft 24, and as a result, the treatment device 18 relatively easily enters the left popliteal artery 220. Thereafter, by way of radiography, the surgeon checks the state where the treatment portion 20 has been delivered to the position matching the stenosed portion X, and ends the device delivery step when the treatment portion 20 is at the stenosed portion.

Figure 6A:
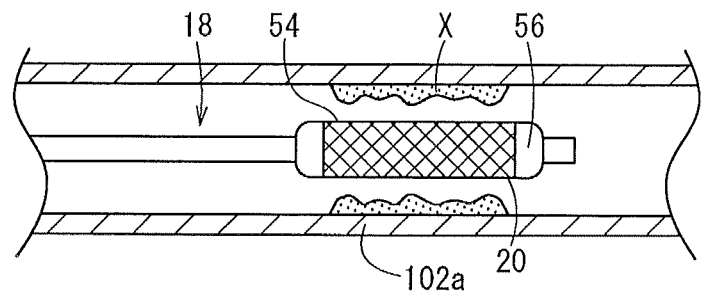
FIG. 6A is an eighth illustrative view of the treatment method following FIG. 5D.
Figure 6B:
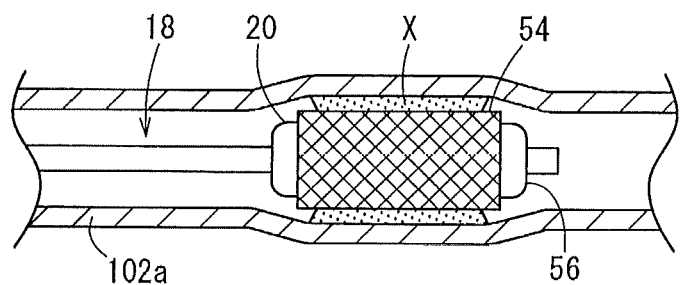
FIG. 6B is a ninth illustrative view of the treatment method following FIG. 6A.
Figure 6C:
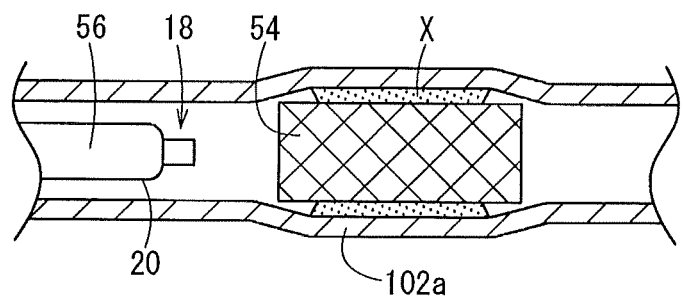
FIG. 6C is a tenth illustrative view of the treatment method following FIG. 6B.

Subsequently, in the treatment step, the surgeon provides treatment by which the stenosed portion X of the left popliteal artery 220 expands. Specifically, as shown in FIG. 6A, the surgeon positions the treatment portion 20 such that the treatment portion 20 is located at the position of the stenosed portion X in the axial direction so that the treatment portion 20 is positioned inside the stenosed portion 20. Next, as shown in FIG. 6B, the surgeon dilates the balloon 56, such that the stent 54 around the balloon 56 dilates in the radial outward direction of the left popliteal artery 220. As a result, the stent 54 dilates and expands a blood vessel wall 102a of the left popliteal artery 220, and maintains the dilated state. After the stent 54 dilates, the balloon 56 contracts again as shown in FIG. 6C, and the treatment device 18 retreats (is moved rearwardly).

That is, since the dilated stent 54 remains in the left popliteal artery 220 (stenosed portion X), dilation of the artery in the radial direction is supported, and the blood flows smoothly inside the stent 54. The stent 54 may be an indwelling drug eluting stent. For example, by functioning as a drug eluting stent that suppresses restenosis, the stent 54 can keep the blood vessel 102 dilated continuously.

In the treatment method according to the first embodiment, the treatment device 18 for treating the treatment target is not limited to the stent delivery device, and various modified examples and application examples can be adopted. Hereinafter, several examples of the treatment device 18 in other forms will be described.

Figure 7B:
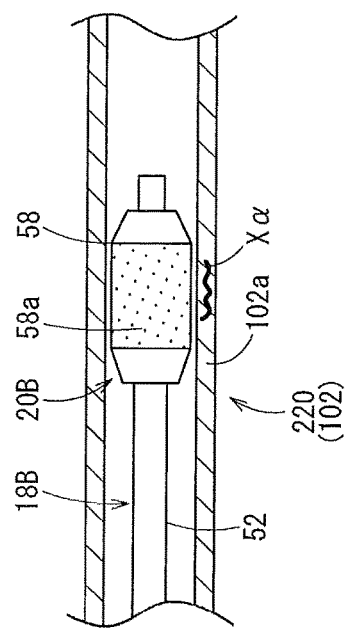
FIG. 7B is a schematic view showing a treatment device of a treatment method according to a second modified example.
Figure 7D:
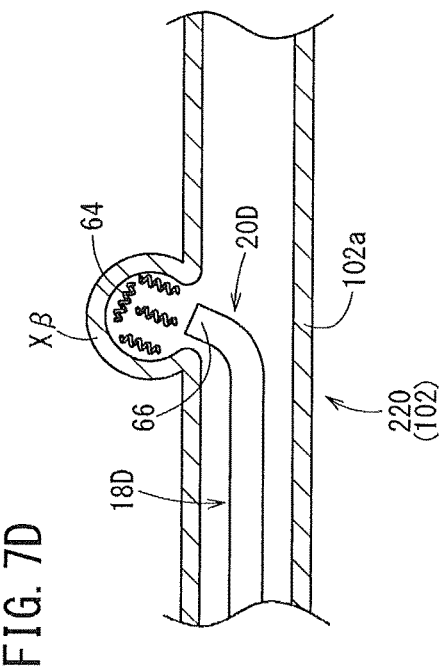
FIG. 7D is a schematic view showing a treatment device of a treatment method according to a fourth modified example.
Figure 7A:
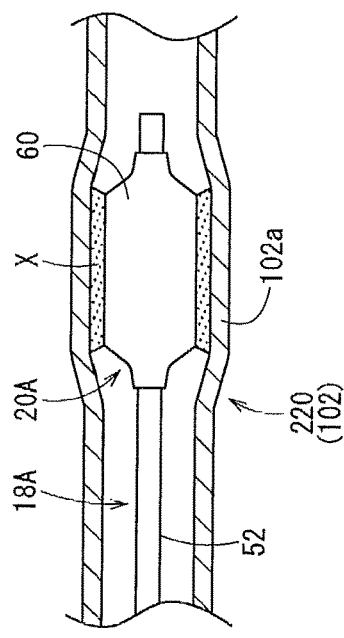
FIG. 7A is a schematic view showing a treatment device of a treatment method according to a first modified example.

In a treatment method according to a first modified example shown in FIG. 7A, a treatment portion 20A of a treatment device 18A includes a balloon 60. After being delivered to the treatment target (for example, the stenosed portion X) by the treatment device advance step, the balloon 60 is dilated in the radial outward direction by a dilation operation performed by the surgeon. As a result, the blood vessel 102 of the stenosed portion X expands, whereby blood flow becomes smooth.

In a treatment method according to a second modified example shown in FIG. 7B, a treatment device 18B is configured with a drug applying device 18B (Drug Eluting Balloon catheter: DEB). The drug applying device 18B is sometimes used, for example, in the case where damage Xα such as cracks is formed in the blood vessel wall 102a of the blood vessel 102 as a treatment target by percutaneous transluminal angioplasty (PTA) or the like. The treatment portion 20B of the drug applying device 18B is configured to include a balloon 58 which dilates to a size approximately the same as or slightly smaller than the inner diameter of the blood vessel 102 with the damage Xα. The lateral circumferential surface of the balloon 58 is coated with a drug 58a for treating the damage Xα. The drug applying device 18B can apply the drug 58a to the damage Xα by using the dilated balloon 58.

Figure 7C:
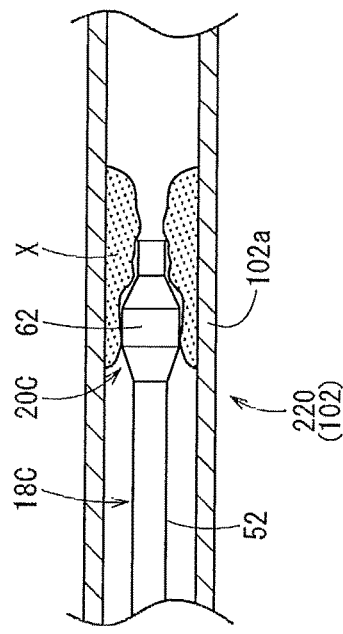
FIG. 7C is a schematic view showing a treatment device of a treatment method according to a third modified example.

In a treatment method according to a third modified example shown in FIG. 7C, a treatment portion 20C of a treatment device 18C includes a cutter portion 62 (atherectomy device) that scrapes off an atheroma (plaque). For example, after being delivered to the treatment target by the treatment device advance step, the cutter portion 62 rotates on the axis of the treatment device side shaft 52 based on the operation performed by the surgeon, and treats the target by removing the atheroma around the cutter portion 62.

In a treatment method according to a fourth modified example shown in FIG. 7D, a treatment device 18D is for treating an aneurysm Xβ (treatment target) formed in the blood vessel 102. The treatment device 18D has, as a treatment portion 20D, an indwelling device/substance sending portion 66 for filling the aneurysm Xβ with an indwelling device/substance 64 (for example, a coil). After being delivered into the aneurysm Xβ (or to an opening portion of the aneurysm Xβ) by the treatment device advance step, the indwelling device/substance sending portion 66 fills the aneurysm Xβ with the indwelling device/substance 64 based on the operation performed by the surgeon, thereby treating the target by blocking the aneurysm Xβ.

As another treatment device 18 applicable to the treatment target, for example, an aspiration mechanism that aspirates thrombi and the like constituting the stenosed portion X can be used.

Figure 8A:
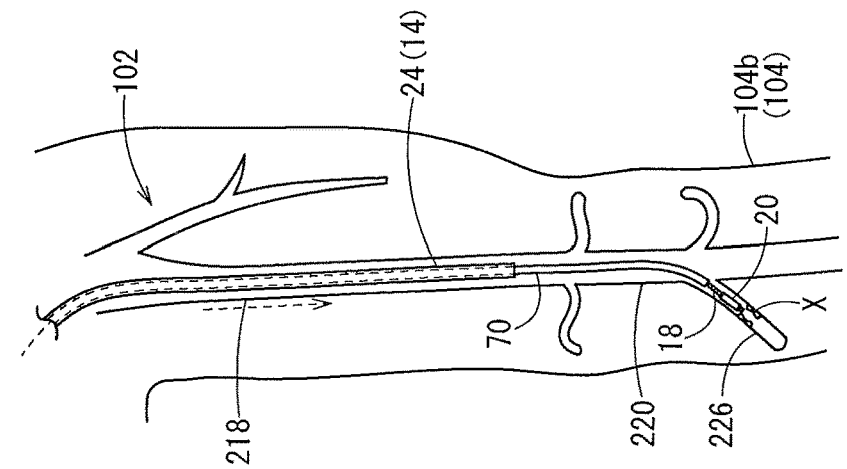
FIG. 8A is a first illustrative view showing a treatment method according to a fifth modified example.
Figure 8B:
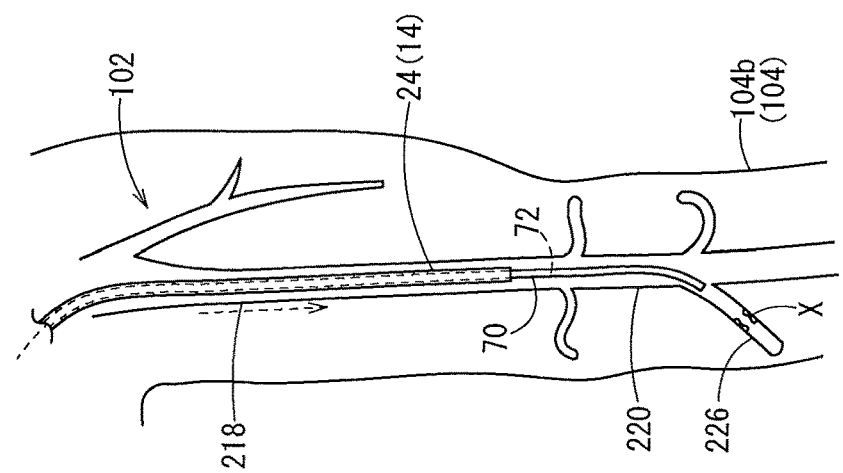
FIG. 8B is a second illustrative view of the treatment method following FIG. 8A.
Figure 8C:
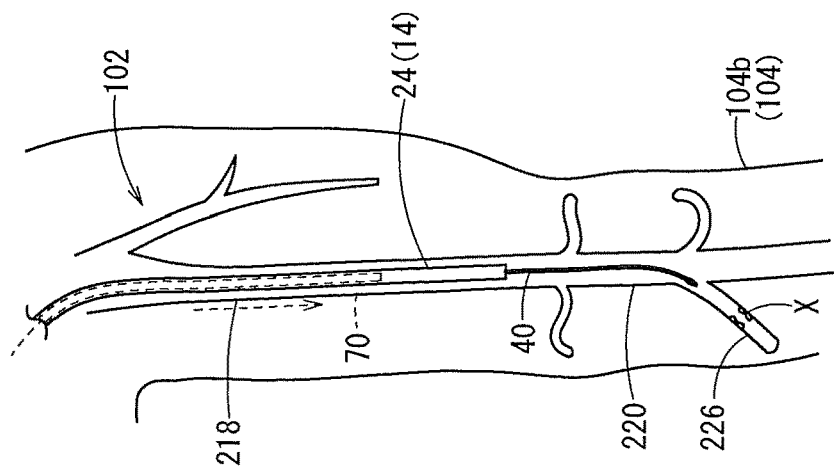
FIG. 8C is a third illustrative view of the treatment method following FIG. 8B.

In a treatment method according to a fifth modified example shown in FIGS. 8A to 8C, a guiding catheter 70 (third catheter) is sent out of the outer catheter 14. The guiding catheter 70 accommodates the treatment device 18 in an accommodating space 72 (lumen) inside the guiding catheter 70. At a stage in which the guiding catheter 70 has made an advance inside the blood vessel 102 to a certain extent, the catheter can send out the treatment device 18. The treatment device 18 can adopt various configurations described above, such as a stent delivery device.

The aforementioned treatment method is particularly effective when a treatment target X is in a peripheral blood vessel 226 smaller than the artery. Hereinafter, a specific example of the treatment method will be described. In this case, to the pull-out step in which the inner catheter 16 is pulled out of the outer catheter 14 of the assembly 12 delivered to the left femoral artery 218, the same method as described above can be adopted. After the pull-out step, as shown in FIG. 8A, the surgeon performs the catheter advance step in which the guiding catheter 70 is caused to advance along the insertion lumen 28 of the outer catheter 14.

In the catheter advance step, the guiding catheter 70 is sent out of (advanced beyond) the distal opening 28a of the outer catheter 14. Moreover, as shown in FIG. 8B, the guiding catheter 70 is caused to advance, and the distal portion of the guiding catheter 70 is delivered to a portion near the opening portion of the peripheral blood vessel 226. Subsequently, in the same manner as in the aforementioned treatment device advance step, the treatment device 18, which has been accommodated in advance in the accommodation space 72 of the guiding catheter 70, is sent out of (advanced beyond) the distal end of the guiding catheter 70 and delivered to the treatment target X of the peripheral blood vessel 226. Thereafter, the treatment step in which the treatment target X is treated by the treatment portion 20 of the treatment device 18 is performed.

As described above, by sending the guiding catheter 70 out of the outer catheter 14, the treatment device 18 can be delivered to various blood vessels 102 present in the lower limb 104. Particularly, although the blood vessel 102 closer to the peripheral side than to the left popliteal artery 220 meanders quite a lot, the guiding catheter 70 having a diameter smaller than that of the outer catheter 14 excellently advances to a portion near the treatment target of the peripheral blood vessel 226. As a result, the treatment device 18 can be rather easily delivered to the treatment target.

The third catheter that is delivered to the treatment target X through the inside of the outer catheter 14 is not limited to the guiding catheter 70 and can be configured or constituted in various ways. For example, as the third catheter, an angiographic catheter for performing angiography inside a blood vessel, a microcatheter for treating smaller blood vessels, and the like can be used. Moreover, depending on the treatment method, the inner catheter 16 as a second catheter may be caused to advance without being pulled out (without performing the pull-out step), and the treatment device 18 may be guided through the inside of the inner catheter 16. Even in this case, it is possible to make the treatment device 18 pass through the lumen (inside) of the outer catheter 14.

As described above, in the treatment method according to the first embodiment, by using the assembly 12 constituted with double catheters (two catheters), the distal portion 12a of the assembly 12 can be more easily delivered to the blood vessel 102 of the lower limb 104. That is, the assembly 12 has a double structure composed of the outer catheter 14 and the inner catheter 16, and accordingly, the properties (kink resistance, torque-transmitting properties, operability, and the like) required at the time of delivery are improved. As a result, even when the assembly 12 is long enough to reach the lower limb 104 from the arm 106, it is relatively easy for the surgeon to operate the distal portion 12a of the assembly 12 and to cause the distal portion 12a to advance inside a blood vessel. Consequently, the surgeon can provide treatment by efficiently disposing the outer catheter 14 in a predetermined position and smoothly and accurately delivering the treatment device 18 to the treatment target through the outer catheter 14.

Moreover, since the sheath 46 having an outer diameter of 2.8 mm is used, a quite thick catheter (for example, a catheter having an outer diameter of around 2.4 mm) can be used as the outer catheter 14, and accordingly, the properties required at the time of delivery can be further improved.

In the delivery step, the distal portion 12a of the assembly 12 is positioned in the left femoral artery 218. Accordingly, in the device advance step, the outer catheter 14 can assist (guide) the advance of the treatment device 18. The diameter of the treatment device 18 is smaller than that of the outer catheter 14, and as a result, the treatment device 18 can excellently advance inside the left popliteal artery 220 that relatively meanders much. Furthermore, even when the treatment target is present in a portion near the knee, the calf, or a portion near the ankle, the properties required at the time of delivering the catheter assembly 12 having a double structure can be maintained. Therefore, the treatment device 18 can be smoothly delivered.

In addition, by the lock mechanism 32, the outer catheter 14 and the inner catheter 16 are fixed to (locked with) each other. Accordingly, when operating the assembly 12, the surgeon can integrally operate the outer catheter 14 and the inner catheter 16. As a result, the properties required at the time of delivering the assembly 12 inserted into the blood vessel 102 can be further improved.

Next, a treatment method according to a second embodiment will be described with reference to FIGS. 9A to 10B. The treatment method according to the second embodiment is a procedure for treating treatment targets (hereinafter, described as "right stenosed portion X1" and "left stenosed portion X2") in both the lower limbs (a right leg 104a and a left leg 104b) of the patient 100. The intervention device 10 used in this treatment method is basically the same as the intervention device 10 of the first embodiment.

In the following description, a sequence will be described in which the left stenosed portion X2 is first treated similar to the first embodiment, and then the right stenosed portion X1 is treated. In this case, for treating the left stenosed portion X2, the procedure from the introduction step to the treatment step can be performed. Moreover, the order of treating the right leg 104a and the left leg 104b can be optionally determined by the surgeon.

In the treatment method according to the second embodiment, after the treatment step for left stenosed portion X2 ends, as shown in FIG. 9A, a device retreat step is performed in which the treatment device 18 having been used for treating the left stenosed portion X2 is caused to retreat from the outer catheter 14. As a result, the treatment device 18 is pulled out of the outer catheter 14, and the outer catheter 14 and the guide wire 40 remain in the body of the patient 100.

Thereafter, as shown in FIG. 9B, the surgeon performs a retreat step in which the distal portion of the outer catheter 14 is caused to retreat to the connection position Z between the right common iliac artery 228 and the left common iliac artery 214. As a result, the distal portion of the outer catheter 14 positioned in the left femoral artery 218 retreats to the peripheral side (connection position Z) of the abdominal aorta 212 through the left external iliac artery 216 and the left common iliac artery 214. At this time, the guide wire 40 is also caused to retreat.

After the retreat step, as shown in FIG. 10A, the surgeon performs a step of delivery to an individual site in which the outer catheter 14 is delivered from the peripheral side of the abdominal aorta 212 to a predetermined position of the right femoral artery 230 of the right leg 104a. At this time, led by the guide wire 40, the outer catheter 14 is caused to advance and be delivered inside the right common iliac artery 228, a right external iliac artery 229, and a right femoral artery 230. In the step of delivery to an individual site, depending on the state of the blood vessel 102 of the patient 100 (for example, a state where the blood vessel meanders much, a state where the blood vessel is small, and the like), the inner catheter 16 may be reinserted into the outer catheter 14, and the assembly 12 may be reestablished. As a result, the distal portion 12a of the assembly 12 can be delivered to the right femoral artery 230, similarly to the case where it is delivered to the left femoral artery 218.

After the step of delivery to an individual site, as shown in FIG. 10B, the surgeon performs a step of causing a treatment device to advance to an individual site in which a treatment device 80 (device for treating an individual site) for treating the right stenosed portion X1 of the right leg 104a is caused to advance. As the treatment device 80, a device in which the stent 54 that will remain in the right stenosed portion X1 is disposed in a treatment portion 80a is used. The treatment device 80 is caused to advance through the insertion lumen 28 of the outer catheter 14 and sent out of (advanced beyond) the distal opening 28a of the outer catheter 14 to the right femoral artery 230. After the treatment device 80 is sent to the right femoral artery 230, the treatment portion 80a is delivered to a site (right popliteal artery 232) where the right stenosed portion X1 is present.

Thereafter, an individual site treatment step in which the right stenosed portion X1 is treated by the treatment device 80 is performed in the right stenosed portion X1. In the individual site treatment step, due to dilation of the balloon 56 of the treatment portion 80a of the treatment device 80, the stent 54 dilates, whereby the right stenosed portion X1 expands. As a result, the stent 54 remains in the right stenosed portion X1 to maintain the dilated state, and treatment of the right stenosed portion X1 ends.

As described above, according to the treatment method of the second embodiment, when a treatment target is present in both the lower limbs 104, the intervention procedure can be consecutively performed. That is, after the treatment target in one of the lower limbs 104 is treated, the outer catheter 14 is caused to retreat to the peripheral side of the abdominal aorta 212 and then caused to advance to the treatment target of the other lower limb 104. In this manner, plural treatment targets present in different sites can be treated by a single treatment.

As a modified example (sixth modified example) of the treatment method according to the second embodiment, before the individual site treatment step, a step of causing a catheter to advance to an individual site may be performed in which the distal end of a guiding catheter 82 (third catheter) is caused to advance. For example, as shown in FIGS. 11A to 11C, when the right stenosed portion X1 is present in the peripheral blood vessel 226 connected to the right popliteal artery 232 of the right leg 104a, the distal portion of the guiding catheter 82 is delivered to a portion near the right stenosed portion X1 through the insertion lumen 28 of the outer catheter 14. Thereafter, the treatment device 18 is sent out of (advanced beyond) the distal portion of the guiding catheter 82, whereby a treatment portion 80a of the treatment device 80 can be excellently delivered to the right stenosed portion X1.

Next, a treatment method according to a third embodiment will be described with reference to FIGS. 12 to 29. The treatment method according to the third embodiment is basically a procedure that treats the same treatment target as being treated in the first embodiment. In this treatment method, an intervention device (for example, a catheter assembly 10x of FIG. 12) different from the intervention device 10 used in the first and second embodiments can be used.

In the following description, the intervention device used in the treatment method of the third embodiment will first be described. For the sake of description and clearer understanding, the dimensional ratio of the drawings may be magnified and may thus differ from the actual ratio in some cases. In the following description, the side of the catheter assembly close to the surgeon is called "proximal side" (proximal end), and the side inserted into the body is called "distal side" (distal end).

Figure 12:
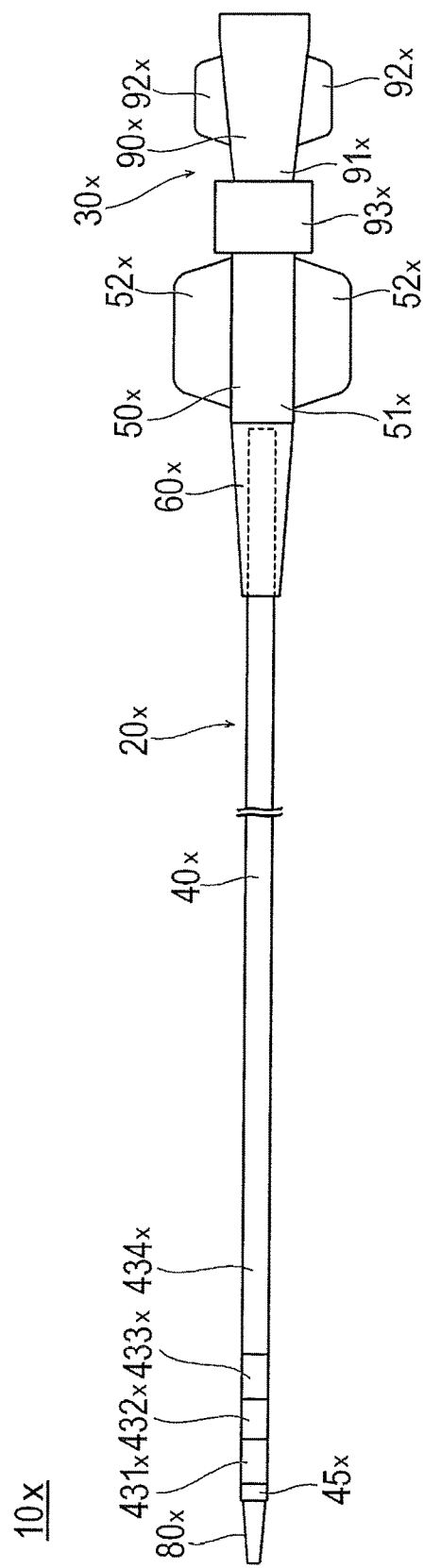
FIG. 12 is a plan view showing a catheter assembly used in a treatment method according to a third embodiment representing a further example of the treatment method disclosed here.

As shown in FIGS. 12, 13A and 13B, the catheter assembly 10x according to the third embodiment disclosed here has a double structure composed of an outer catheter 20x and an inner catheter 30x. The catheter assembly 10x is percutaneously inserted into the radial artery, the brachial artery, the femoral artery, and the like. The distal end of the catheter assembly 10x is caused to reach a target site through a blood vessel, such that a catheter for treatment such as a balloon catheter or various liquids such as a contrast agent, a drug solution, and physiological saline are introduced into a target site. Moreover, in the intervention procedure in which a catheter is introduced from the artery of an arm to treat a lower limb, the catheter assembly 10x is inserted into the artery (the radial artery or the brachial artery) of an arm.

The outer catheter 20x has a tubular outer catheter body 40x, an outer catheter hub 50x fixed to the proximal end of the outer catheter body 40x, and an anti-kink protector 60x.

The inner catheter 30x has an inner catheter body 31x that is configured to be inserted into the outer catheter body 40x, and an inner catheter hub 90x that is disposed at the proximal end of the inner catheter body 31x. The inner catheter hub 90x is connected to the proximal end of the inner catheter body 31x. The inner catheter body 31x includes a linear shaft 70x that is configured to be inserted into the outer catheter body 40x, and a tubular body 80x that is disposed in the distal end of the shaft 70x. The tubular body 80x is connected to the distal end of the shaft 70x.

When the distal side of the tubular body 80x is inserted into the proximal side of the outer catheter hub 50x, and the outer catheter hub 50x and the inner catheter hub 90x come into contact with and are connected to each other and fixed by a lock mechanism which will be described later, the outer catheter 20x is assembled with the inner catheter 30x (assembled state) as shown in FIG. 12. If the outer catheter hub 50x and the inner catheter hub 90x can be connected to each other, the lock mechanism does not have to be provided. Moreover, a slit, through which a guide wire can pass into and out of the catheter assembly, may extend from the distal end to the proximal end of the inner catheter hub 90x. According to the above construction or configuration, in the state where the guide wire is inserted in the catheter assembly 10x, a surgeon can rather easily withdraw the inner catheter while remaining the guide wire and the outer catheter 20x in the body lumen.

Figure 14:
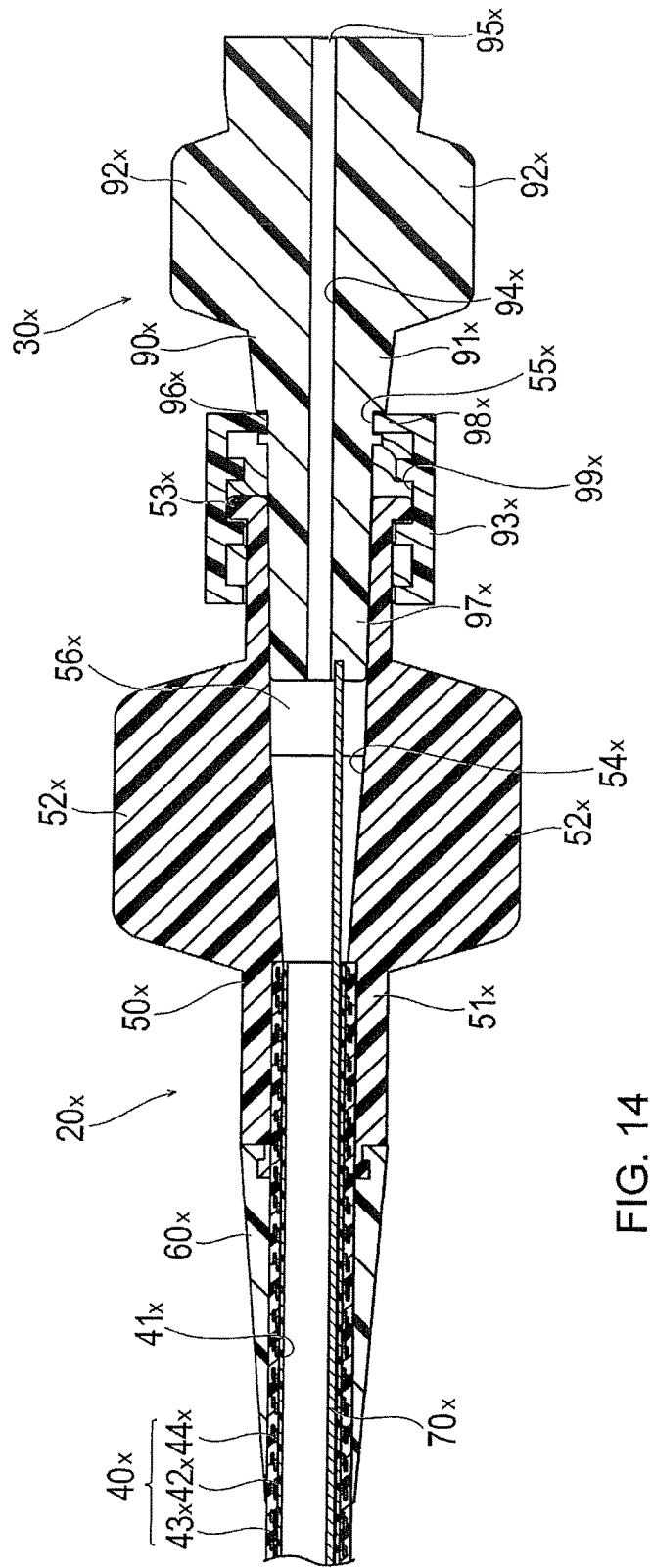
FIG. 14 is a vertical cross-sectional view of the proximal portion of the catheter assembly shown in FIG. 12.

First, the outer catheter 20x will be described. As shown in FIGS. 13 and 14, the outer catheter body 40x is in the form of a flexible tube, and in the portion which approximately corresponds to the center of the outer catheter body 40x, an outer catheter lumen 41x which is as long as the full length of the outer catheter body 40x is formed. The outer catheter lumen 41x thus extends along the entire length of the outer catheter body 40x.

Figure 15:
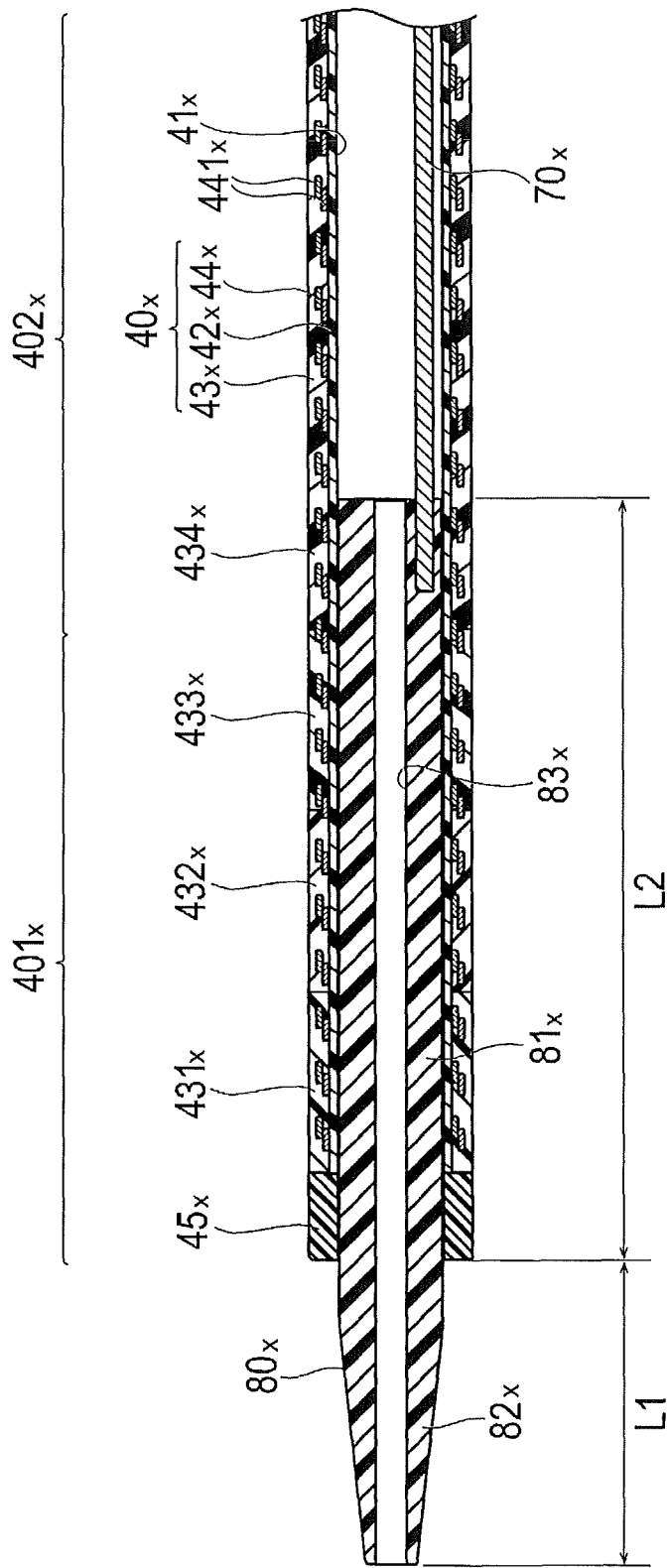
FIG. 15 is a vertical cross-sectional view of the distal portion of the catheter assembly shown in FIG. 12.

The outer catheter body 40x has an inner layer 42x that forms an inner surface of the outer catheter lumen 41x, an outer layer 43x that forms the outer surface, a reinforcing layer 44x between the inner layer 42x and the outer layer 43x, and a highly flexible soft tip 45x disposed at the distal side of the inner layer 42x, the reinforcing layer 44x, and the outer layer 43x as shown in FIG. 15.

The outer layer 43x has a first area 431x positioned on the proximal side of the soft tip 45x, a second area 432x positioned on the proximal side of the first area 431x, a third area 433x positioned on the proximal side of the second area 432x, and a fourth area 434x positioned on the proximal side of the third area 433x. More specifically, the first area 431x is positioned immediately axially adjacent the soft tip 45x on the proximal side of the soft tip 45x, the second area 432x is positioned immediately axially adjacent the first area 431x on the proximal side of the first area 431x, the third area 433x is positioned immediately axially adjacent the second area 432x on the proximal side of the second area 432x, and the fourth area 434x is positioned immediately axially adjacent the third area 433x on the proximal side of the third area 433x. The proximal end of the fourth area 434x is fixed to the outer catheter hub 50x. The third area 433x is more flexible than the fourth area 434x, the second area 432x is more flexible than the third area 433x, and the first area 431x is more flexible than the second area 432x.

In the outer catheter body 40x, an area from the distal portion of the fourth area 434x to the soft tip 45x forms a rigidity transition portion 401x in which the rigidity is reduced toward the distal end. Moreover, an area including the fourth area 434x forms a rigidity uniform portion 402x in which the rigidity is uniform in the axial direction. If the above constitution is adopted, when inserting the catheter assembly 10x into a blood vessel, the surgeon can more safely insert it into the blood vessel while securing sufficient pushability and sufficiently transmitting torque to the distal side.

Examples of constituent materials of the first area 431x, the second area 432x, the third area 433x, and the fourth area 434x include various thermoplastic elastomers based on styrene, polyolefin, polyurethane, polyester, polyamide, polybutadiene, transpolyisoprene, fluororubber, chlorinated polyethylene, and the like. For example, one kind of these may be used singly, or a combination of two or more kinds thereof (a polymer alloy, a polymer blend, a laminate, and the like) may be used.

It is preferable for the inner layer 42x to be made of a material or provided with properties which, when at least a portion of the outer catheter lumen 41x comes into contact with a medical instrument, the contact is a relatively small frictional force, when the medical instrument such as a catheter for treatment or a guide wire is inserted into the outer catheter lumen 41x. If such a material is used, the medical instrument inserted into the outer catheter body 40x can be moved in the axial direction with a lower sliding resistance, whereby the operability is improved. The entire inner layer 42x may be made of a low-friction material. Examples of the low-friction material include fluororesin materials such as polytetrafluoroethylene (PTFE).

The surgeon inserts the catheter assembly 10x into the body while checking its position under radiography. Accordingly, it is preferable for the constituent material of the outer catheter body 40x to contain a radiopaque material (X-ray contrast agent). Examples of the radiopaque material which can be used include barium sulfate, bismuth oxide and tungsten. The radiopaque material may be present throughout the full length of the outer catheter body 40x or may be present in a portion of the outer catheter body 40x.

The reinforcing layer 44x is for reinforcing the outer catheter body 40x, and contains a reinforcing material consisting of or including plural reinforcing wires 441x. The gaps between the plural reinforcing wires 441x in the reinforcing layer 44x are filled with the material of the outer layer 43x or the inner layer 42x. Examples of the reinforcing material include the reinforcing wire 441x that is in the form of a helix or a net. The reinforcing wire 441x is made of metals such as stainless steel and NiTi. Specific examples of the wire-like material include a flat plate-shaped material that is obtained by squashing a stainless steel wire to form a flat-shaped like wire such that the thickness of the outer catheter 20x in the radial direction thereof becomes small. Examples of the reinforcing material also include a helix formed of plural strands (about 8 to 32 strands) of the wire, a material (braid) obtained by braiding the wires, and the like. The number of strands of the reinforcing wire 441x is preferably a multiple of 8, since the catheter is reinforced well with excellent balance in the form of a tube in this manner. The reinforcing wire 441x is not limited to the aforementioned flat plate-shaped material, and may be, for example, a round wire or an oval wire. Moreover, a strand of the reinforcing wire 441x may be a bundle of two or more strands of wires.

Since the catheter has the reinforcing layer 44x, the catheter exhibits sufficient rigidity and strength, without increasing the thickness of the wall of the outer catheter body 40x. The outer catheter body 40x can thus maintain a relatively large inner diameter. As a result, a medical instrument that has a relatively large outer diameter can be inserted into the catheter, and the outer catheter 20x that has excellent pushability and torque-transmitting properties and is not easily kinked or crushed is obtained.

The soft tip 45x is more flexible than the tubular body 80x having three-layer structure consisting of the inner layer 42x, the reinforcing layer 44x, and the outer layer 43x. Accordingly, when the catheter assembly 10x that is in an assembled state is inserted into the body, it is possible to minimize the damage of a blood vessel caused by the distal end of the outer catheter body 40x.

Examples of the constituent material of the soft tip 45x include various rubber materials such as natural rubber, isoprene rubber, butadiene rubber, chloroprene rubber, silicone rubber, fluororubber, and styrene-butadiene rubber, and various thermoplastic elastomers based on styrene, polyolefin, polyurethane, polyester, polyamide, polybutadiene, transpolyisoprene, fluororubber, chlorinated polyethylene, and the like.

The outer diameter of the outer catheter body 40x is preferably from 1.35 mm to 3 mm. If the outer diameter is too large, operability at the time when the outer catheter body 40x is inserted into and moved inside an artery may deteriorate, and the strain that the patient suffers from may increase.

The inner diameter of the outer catheter body 40x is preferably from 1.2 mm to 2.85 mm. If the inner diameter is too small, it is not preferable since the outer diameter of a catheter for treatment that can be inserted into the outer catheter body 40x also needs to be reduced accordingly, and a choice of medical instruments to be inserted and used is restricted.

The length of the outer catheter body 40x can be appropriately set according to the use of the outer catheter 20x, and is, for example, 500 mm to 2,500 mm.

The outer catheter hub 50x is fixed to the proximal end of the outer catheter body 40x. As shown in FIGS. 13 and 14, the outer catheter hub 50x is configured to include a hollow external catheter body portion 51x, plural (two in the present embodiment) outer catheter blade portions 52x that protrude radially outwardly from the outer lateral surface of the external catheter body portion 51x, and a helical bump or enlargement 53x that is formed on the outer lateral surface of the proximal portion of the external catheter body portion 51x. In the external catheter body portion 51x, an outer catheter hub lumen 54x that comes into contact with the outer catheter lumen 41x and an outer catheter hub opening portion 55x that is open at the proximal end of the outer catheter hub lumen 54x are formed. The helical bump 53x can be screwed with a helical groove 99x that is formed in a screwing portion 93x which is disposed in the inner catheter hub 90x and will be described later. A cylindrical portion 97x which is formed at the distal end of the inner catheter hub 90x can be inserted into the outer catheter hub opening portion 55x. The helical bump 53x and the screwing portion 93x constitute a lock mechanism for maintaining the state where the outer catheter hub 50x is connected to the inner catheter hub 90x.

The outer catheter hub lumen 54x includes a tapered portion 56x whose inner diameter is reduced toward the distal end from the outer catheter hub opening portion 55x. The tapered portion 56x is a female luer taper configured to be fitted to or with a male luer taper formed on the outer surface of the cylindrical portion 97x of the inner catheter hub 90x. When a medical instrument such as a balloon catheter is inserted from the outer catheter hub opening portion 55x, the tapered portion 56x guides the medical instrument into the outer catheter lumen 41x by using the inner surface of which the inner diameter is reduced toward the distal end.

Examples of the constituent material of the outer catheter hub 50x include various thermoplastic elastomers based on styrene, polyolefin, polyurethane, polyester, polyamide, polybutadiene, transpolyisoprene, fluororubber, chlorinated polyethylene, and the like. For example, one kind of these may be used alone, or a combination of two or more kinds thereof (a polymer alloy, a polymer blend, a laminate, and the like) may be used.

In the assembled state, the inner catheter 30x is inserted into the outer catheter hub 50x from the proximal side. However, after the inner catheter 30x is pulled out, for example, an elongated device/substance (linear device/substance) such as a guide wire, catheters (for example, a balloon catheter for PTCA), an endoscope, an ultrasonic probe, or a temperature sensor can be inserted into the outer catheter hub 50x or pulled out of the outer catheter hub 50x. Alternatively, various liquids such as a contrast agent (X-ray contrast agent), a drug solution, and physiological saline can be injected into the outer catheter hub 50x.

The anti-kink protector 60x is mounted on the catheter such that it covers a portion where the outer catheter body 40x is connected to the outer catheter hub 50x. The anti-kink protector 60x inhibits the outer catheter 20x from kinking at the position at which the anti-kink protector 60x is located.

Next, the inner catheter 30x will be described. As shown in FIGS. 13 and 14, the tubular body 80x disposed in the inner catheter 30x has a tubular body proximal portion 81x possessing an outer diameter that is constant in the axial direction, and a tubular body distal portion 82x possessing an outer diameter that reduced such that the portion 82x is tapered toward the distal end in the axial direction. The axial central portion of the tubular body 80x includes an inner catheter lumen 83x that penetrates the tubular body 80x from the distal end to the proximal end. The outer diameter of the tubular body proximal portion 81x is approximately the same as the inner diameter of the outer catheter body 40x. As long as the tubular body 80x can be inserted into and pulled out of the outer catheter body 40x, the outer diameter of the tubular body proximal portion 81x need not be the same as the inner diameter of the outer catheter body 40x. When the tubular body proximal portion 81x is disposed inside the outer catheter body 40x, the outer surface of the tubular body proximal portion 81x comes into contact with the inner surface of the outer catheter body 40x without a clearance, or is positioned adjacent the inner surface with a small clearance.

The inner diameter of the tubular body 80x may be set to be approximately the same as the outer diameter of the guide wire to be used. As long as the guide wire can be inserted into or pulled out of the tubular body 80x, the inner diameter of the tubular body 80x need not be the same as the outer diameter of the guide wire. For example, when inserting the guide wire into the catheter assembly prior to the insertion of the guide wire into the body lumen, the surgeon inserts the guide wire toward the distal end of the tubular body 80x from an inner catheter hub opening portion 95x in some cases. In this case, regarding the inner diameter of the tubular body 80x, it is preferable for the inner diameter of the proximal opening of the tubular body 80x to be larger than the inner diameter of the distal opening of the tubular body 80x. Moreover, in the distal portion of the tubular body 80x, when the guide wire is disposed inside the inner catheter lumen 83x, the outer surface of the guide wire comes into contact with the inner surface of the tubular body 80x without a clearance or is positioned adjacent the inner surface with a small clearance.

The length of the tubular body 80x is not particularly limited, and is, for example, 200 mm to 600 mm.

In the assembled state, the length L1 between the distal end of the tubular body 80x and the distal end of the outer catheter body 40x in the axial direction is smaller than the length L2 between the distal end of the outer catheter body 40x and the proximal end of the tubular body 80x in the axial direction as shown in FIG. 15. Moreover, the length L2 is sufficient for the tubular body 80x to be accommodated inside the outer catheter 20x. The length L1 is not particularly limited and is, for example, 30 mm to 50 mm.

In addition, in the assembled state, the proximal end of the tubular body 80x is positioned in a portion closer to the proximal side than to the distal end of the rigidity uniform portion 402x of the outer catheter body 40x. That is, the proximal end (proximal-most end) of the tubular body 80x is located on the proximal side of the distal end (distal-most end) of the rigidity uniform portion 402x. Furthermore, in the assembled state, the tubular body distal portion 82x is positioned in a portion closer to the distal side than to the distal end of the outer catheter body 40x. That is, the tapered portion 82x is located (entirely in the illustrated embodiment) on the distal side of the distal end (distal-most end) of the outer catheter body 40x.

Examples of the constituent material of the tubular body 80x include various thermoplastic elastomers based on styrene, polyolefin, polyurethane, polyester, polyamide, polybutadiene, transpolyisoprene, fluororubber, chlorinated polyethylene, and the like. For example, one kind of these may be used singly, or a combination of two or more kinds thereof (a polymer alloy, a polymer blend, a laminate, and the like) may be used.

As shown in FIGS. 13 and 14, the inner catheter hub 90x has a hollow inner catheter body portion 91x, plural (two in the present embodiment) inner catheter blade portions 92x that protrude outwardly from the outer lateral surface of the inner catheter body portion 91x, and the screwing portion 93x that is rotatably disposed on the outer lateral surface of the inner catheter body portion 91x.

The inner catheter body portion 91x includes an inner catheter hub lumen 94x that penetrates the inner catheter body portion 91x from the proximal end to the distal end. The inner catheter hub lumen 94x opens to the inner catheter hub opening portion 95x at the proximal end of the inner catheter body portion 91x. It is preferable for the inner diameter of the inner catheter hub lumen 94x to be larger than the outer diameter of a guide wire to be used. If the above configuration is adopted, a contact area between the outer surface of the guide wire and the inner circumferential surface of the inner catheter hub lumen is reduced, and accordingly, the surgeon can rather easily operate the guide wire at his or her side. Moreover, when inserting the catheter assembly into the body lumen, the surgeon can rather easily insert the guide wire from the distal portion of the tubular body 80x to the inner catheter hub opening portion 95x. As long as the guide wire can be inserted into and pulled out of the inner catheter hub lumen 94x, the inner diameter of the inner catheter hub lumen 94x may be approximately the same as the outer diameter of the guide wire to be used.

The outer surface of the inner catheter body portion 91x includes a circumferentially extending groove portion 96x rotatably fitted to the screwing portion 93x.

The cylindrical portion 97x that is insertable into the outer catheter hub opening portion 55x of the outer catheter hub 50x is located at the distal end of the inner catheter body portion 91x. The outer surface of the cylindrical portion 97x constitutes a male luer taper in which the outer diameter is reduced toward the distal end. When the cylindrical portion 97x is inserted into the outer catheter hub opening portion 55x, the outer surface (male luer taper) of the cylindrical portion 97x comes into close contact with the tapered portion 56x (female luer taper) of the outer catheter hub lumen 54x. As a result, it is possible to communicate the outer catheter hub lumen 54x with the inner catheter lumen 83x while securing a liquid-tight state.

The screwing portion 93x is in the form of a tube. The inner surface of the proximal end of the screwing portion 93x includes a circumferentially extending bump for engagement 98x (an inwardly projecting engaging portion) which rotatably engages the groove portion 96x on the inner catheter body portion 91x. Moreover, the inner surface of the screwing portion 93x includes the helical groove 99x configured to be screw-engaged with the helical bump or enlargement 53x of the outer catheter hub 50x. When the cylindrical portion 97x is inserted into the outer catheter hub opening portion 55x, and the screwing portion 93x is rotated, the helical bump or enlargement 53x screw engages the helical groove 99x, and the cylindrical portion 97x is pushed into the outer catheter hub lumen 54x toward the distal end. As a result, the outer surface of the cylindrical portion 97x comes into close contact with the tapered portion 56x of the outer catheter hub lumen 54x, and a state where the outer catheter hub 50x is connected to the inner catheter hub 90x can be maintained.

Examples of the material which can be used for the inner catheter hub 90x include various thermoplastic elastomers based on styrene, polyolefin, polyurethane, polyester, polyamide, polybutadiene, transpolyisoprene, fluororubber, chlorinated polyethylene, and the like. For example, one kind of these may be used singly, or a combination of two or more kinds thereof (a polymer alloy, a polymer blend, a laminate, and the like) may be used.

As shown in FIGS. 13 and 14, the shaft 70x is a flexible member that extends in the form of a straight line. The distal portion of the shaft 70x is fixed to the tubular body 80x at a position that deviates from the inner catheter lumen 83x of the proximal surface of the tubular body 80x outside the radial direction. That is, the shaft 70x and the inner catheter lumen 83x are not coaxial. The proximal portion of the shaft 70x is fixed to the cylindrical portion 97x of the inner catheter hub 90x at a position that deviates from the inner catheter hub lumen 94x of the distal surface of the cylindrical portion 97x of the inner catheter hub 90x outside the radial direction. That is, the shaft 70x and the inner catheter hub lumen 94x of the inner catheter hub 90x are not coaxial. The shaft 70x flexibly bends while having appropriate rigidity, such that when the inner catheter hub 90x is operated, the tubular body 80x moves in the axial direction simultaneously with the inner catheter hub 90x, and the tubular body 80x to which a force is applied from a body tissue when it is inserted into the body, is not pushed back to the inside of the outer catheter body 40x.

It is preferable to appropriately set the length of the shaft 70x in the axial direction according to the length of the outer catheter body 40x, such that in the assembled state, the distal end of the tubular body 80x is positioned in a portion closer to the distal side than to the distal end of the outer catheter body 40x, and the proximal end of the tubular body 80x is positioned in a portion closer to the proximal side than to the proximal end of the outer catheter body 40x. That is, in the assembled state such as shown in FIG. 15, the distal end (distal-most end) of the tubular body 80x is located on the distal side of the distal end (distal-most end) of the outer catheter body 40x (soft tip 45x). And, in the assembled state, the proximal (proximal-most) end of the tubular body 80x is located on the distal side of the proximal (proximal-most) end of the outer catheter body 40x (taking into account that the outer catheter body 40x does not include the outer catheter hub 50x).

The outer diameter of the shaft 70x is preferably from 0.3 mm to 1.5 mm, but is not limited to this dimensional range. Moreover, the outer diameter of the shaft 70x is set to be smaller than the inner diameter of the outer catheter body. If the outer diameter of the shaft 70x is too large, the movement of the guide wire inside the outer catheter lumen 41x is hindered in the assembled state. If the outer diameter of the shaft 70x is too small, it is difficult to move the tubular body 80x simultaneously with the inner catheter hub 90x.

The material forming the shaft 70x is not particularly limited as long as the rigidity is obtained as required. Examples of materials include metals such as stainless steel and NiTi, various thermoplastic elastomers based on styrene, polyolefin, polyurethane, polyester, polyamide, polybutadiene, transpolyisoprene, fluororubber, chlorinated polyethylene, and the like, thermosetting resins such as unsaturated polyester, a urea resin, a melamine resin, a silicon resin, a phenol resin, and an epoxy resin, and the like. For example, one kind of these may be used singly, or a combination of two or more kinds thereof (a polymer alloy, a polymer blend, a laminate, and the like) may be used. Moreover, the shaft 70x may be constituted with plural materials.

In the assembled state, as shown in FIG. 15, the distal end of the tubular body 80x is disposed in a portion closer to the distal side than to the distal end of the outer catheter body 40x, and the proximal end of the tubular body 80x is disposed in a portion closer to the proximal side than to the distal end of the outer catheter body 40x. That is, as explained above, in the assembled state, the distal end (distal-most end) of the tubular body 80x is located on the distal side of the distal end (distal-most end) of the outer catheter body 40x, and the proximal (proximal-most) end of the tubular body 80x is located on the distal side of the proximal (proximal-most) end of the outer catheter body 40x. Accordingly, when a guide wire 120x is inserted into the inner catheter lumen 83x, the tubular body 80x is positioned in a gap between the outer surface of the guide wire 120x and the inner surface of the outer catheter body 40x (see FIG. 17).

Moreover, in the assembled state, in a cross section which is orthogonal to the axis of the outer catheter body 40x in the distal end of the outer catheter body 40x, the thickness of the tubular body 80x in the radial direction of the tubular body 80x is larger than the thickness of the outer catheter body 40x in the radial direction of the outer catheter body 40x. Accordingly, the surgeon can prevent the distal end of the outer catheter body 40x from protruding from the outer surface of the tubular body 80x outside the radial direction as much as possible, while bringing the distal end of the outer catheter body 40x into contact with the outer surface of the tubular body 80x.

Figure 20:
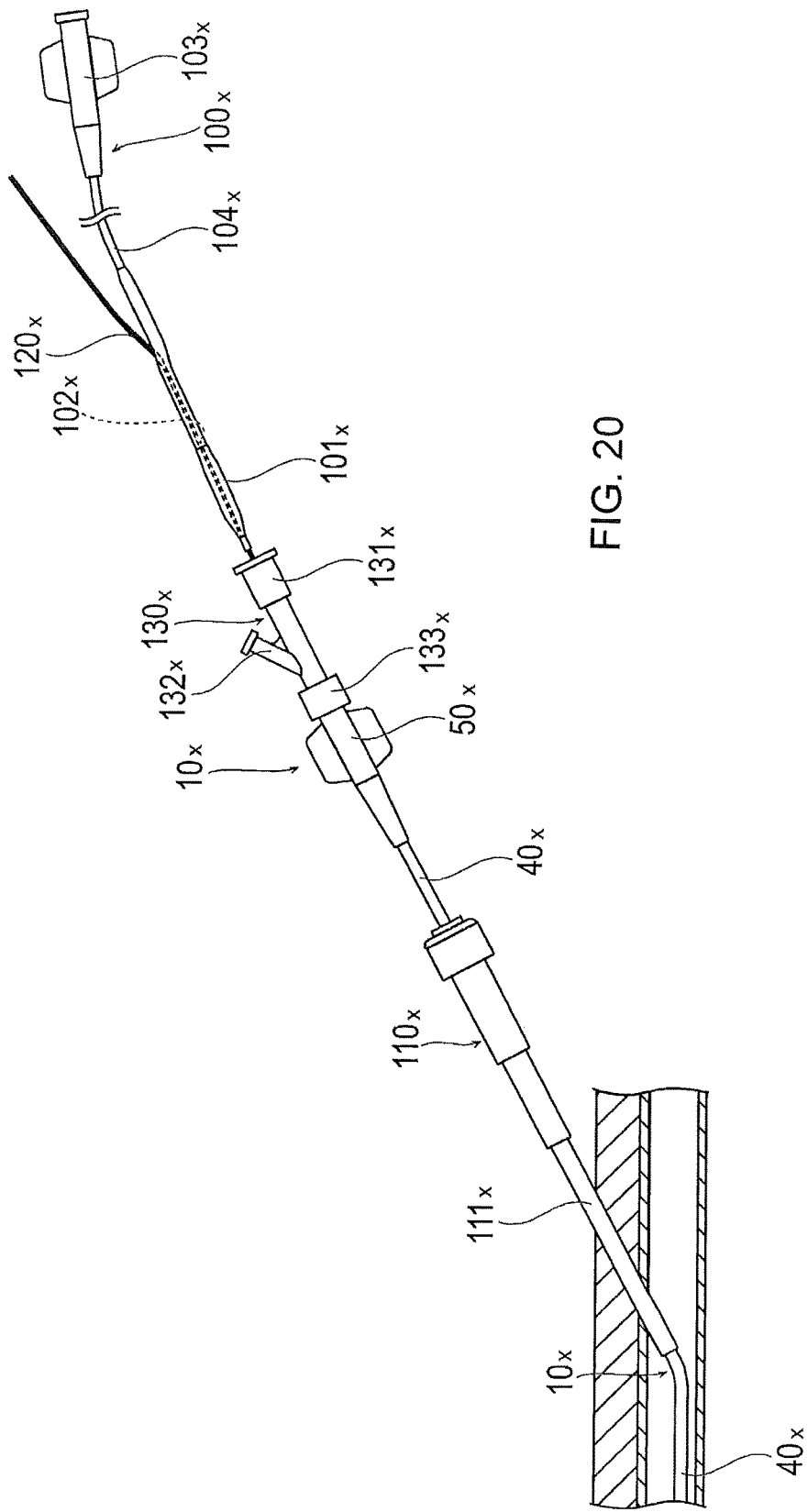
FIG. 20 is a fifth illustrative view showing a state where a balloon catheter is introduced into a blood vessel through the outer catheter, after the inner catheter is pulled out of the catheter assembly used in the treatment method according to the third embodiment.
Figure 22:
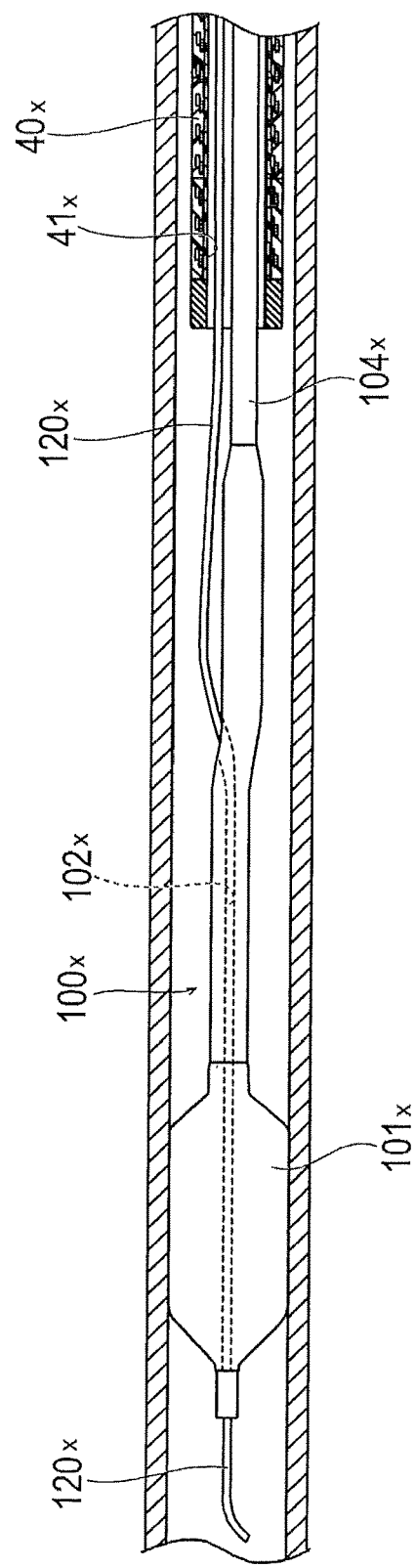
FIG. 22 is a seventh illustrative view showing the way the distal portion of the catheter assembly used in the treatment method according to the third embodiment operates. This is a schematic cross-sectional view showing a state where a balloon catheter having been inserted into a blood vessel through the outer catheter is dilated, after the inner catheter is pulled out of the catheter assembly used in the treatment method according to the third embodiment.

Set forth next is a description of a manner of using the catheter assembly 10x according to the present embodiment. In the following description, for example, a method will be explained in which the surgeon uses the outer catheter 20x as a guiding catheter and introduces a balloon catheter 100x into a blood vessel through the guiding catheter so as to treat a stenosed portion in the blood vessel. The balloon catheter 100x is a rapid exchange type. As shown in FIGS. 20 and 22, a guide wire lumen 102x into which the guide wire 120x is inserted is formed only in the distal portion of the balloon catheter 100x in which a balloon 101x is disposed. In the balloon catheter 100x, when a fluid for dilation is supplied into the balloon 101x of the distal portion from a balloon catheter hub 103x through a lumen for dilation formed in a balloon catheter shaft 104x, the balloon 101x is dilated outside the radial direction by the force of fluid.

First, before the catheter assembly 10x is introduced into a blood vessel, the outer catheter 20x and the inner catheter 30x are assembled as shown in FIGS. 12, 14, and 15, thereby constituting the catheter assembly 10x (supply step). At the time of assembly, the inner catheter 30x is inserted into the outer catheter hub opening portion 55x from the tubular body 80x, and is pushed forward until the cylindrical portion 97x is inserted into or positioned in the outer catheter hub opening portion 55x. When the screwing portion 93x is rotated after the cylindrical portion 97x is inserted into the outer catheter hub opening portion 55x, the helical bump or enlargement 53x is screwed into the helical groove 99x as shown in FIG. 14. As a result, the cylindrical portion 97x is pushed into the outer catheter hub lumen 54x toward the distal end, and the outer surface of the cylindrical portion 97x comes into close contact with the tapered portion 56x of the outer catheter hub lumen 54x. Accordingly, the outer catheter hub lumen 54x communicates with the inner catheter lumen 83x in a liquid-tight state, and this state can be reliably maintained. Therefore, the outer catheter 20x and the inner catheter 30x can be integrally operated when the catheter assembly 10x is inserted into a blood vessel. For this reason, the catheter assembly is rather easily operated, and the outer catheter 20x and the inner catheter 30x are inhibited from being accidentally disassembled, whereby the safety is improved.

Figure 16:
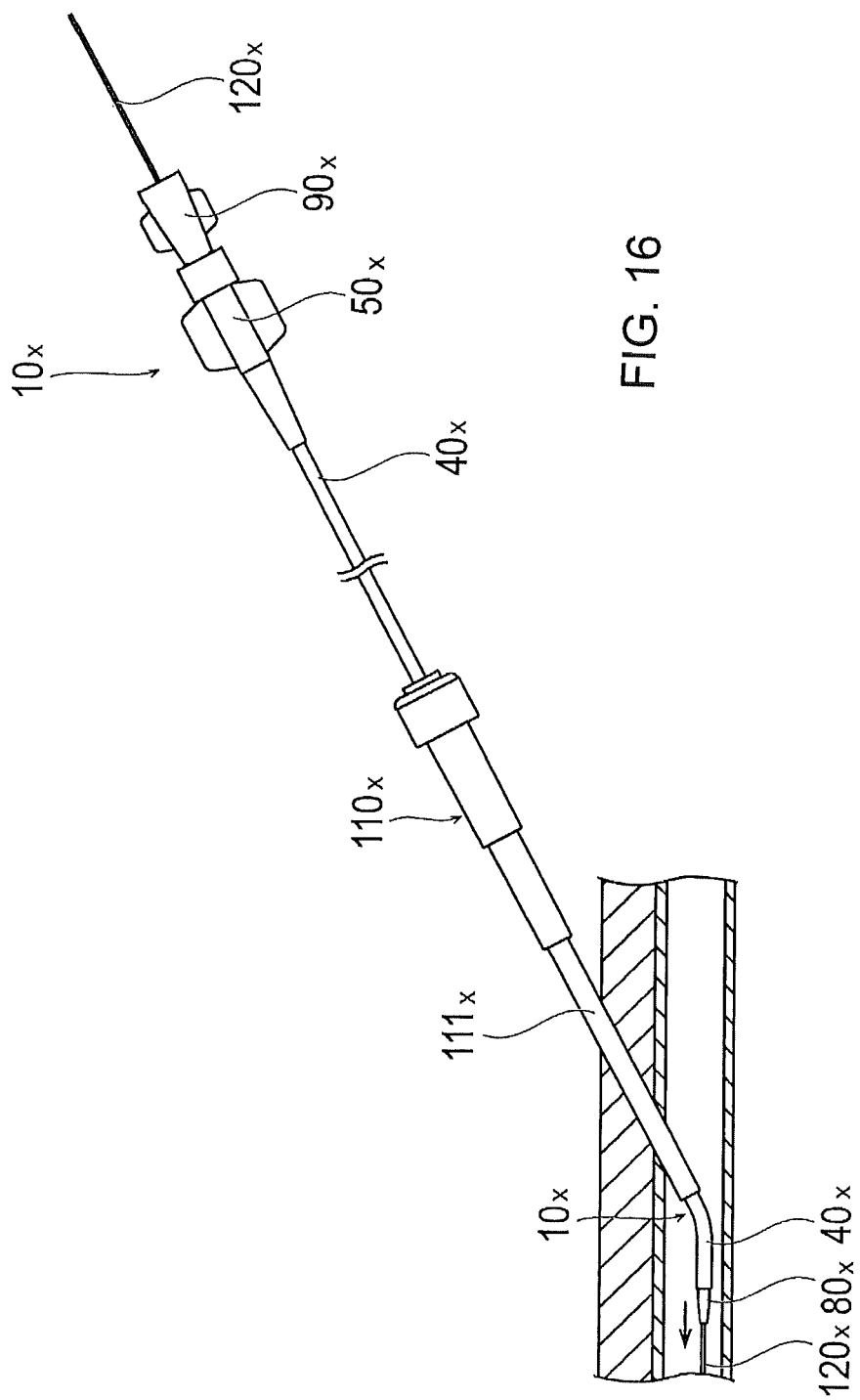
FIG. 16 is a first illustrative view showing a state where the catheter assembly used in the treatment method according to the third embodiment is introduced into a blood vessel.

Next, as shown in FIG. 16, by a known method such as Seldinger technique, the surgeon makes a puncture in the radial artery and inserts a mini-guide wire into the artery. Thereafter, the surgeon inserts a catheter introducer 110x, which is obtained by inserting a dilator into the lumen of sheath 111x, into the punctured portion of the radial artery along the mini-guide wire. After moving the distal end of the catheter introducer 110x to the central side by a predetermined distance, the surgeon withdraws the mini-guide wire and the dilator from the catheter introducer 110x, and leaves the sheath 111x inside the radial artery. In this manner, the surgeon can secure an introduction portion for introducing the catheter assembly 10x into the radial artery. In the following description, a case will be explained in detail in which the surgeon introduces the catheter assembly 10x from the radial artery and treats a stenosed portion present in a blood vessel such as the femoral artery in a lower limb. However, the specific use of the catheter disclosed here is not particularly limited. For example, the surgeon may introduce the catheter assembly 10x from the brachial artery, the femoral artery, or the like. Moreover, the position of the site to be treated, such as a stenosed portion, is not particularly limited.

After securing the introduction portion in the radial artery of an arm, the surgeon inserts the guide wire 120x into the catheter assembly 10x (guide wire insertion step). Specifically, the surgeon inserts the guide wire 120x into the inner catheter lumen 83x, the outer catheter lumen 41x, the outer catheter hub lumen 54x, and the inner catheter hub lumen 94x that constitute the catheter assembly 10x. Subsequently, the surgeon inserts the catheter assembly 10x, in which the guide wire has been inserted, from the distal opening of the sheath 111x. The surgeon then introduces the distal end of the catheter assembly 10x into the radial artery along the guide wire 120x (introduction step). The guide wire insertion step may be performed before the introduction portion is secured in the radial artery of an arm.

Figure 17:
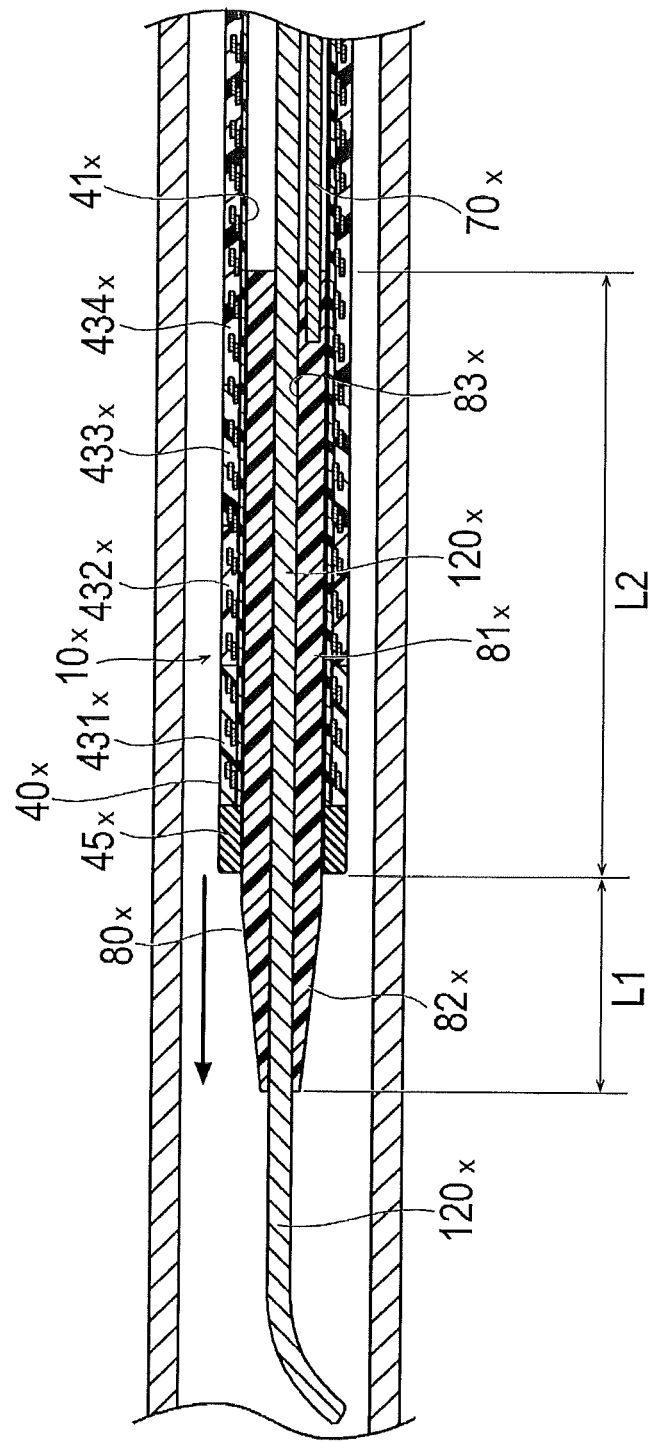
FIG. 17 is a second illustrative view showing the way the distal portion of the catheter assembly used in the treatment method according to the third embodiment operates. This is a schematic cross-sectional view showing the state where the catheter assembly is pushed into a blood vessel.

In the delivery step, as shown in FIG. 17, led by the guide wire 120x, the catheter assembly 10x in the assembled state is slowly pushed toward the stenosed portion (target site). For example, when the catheter assembly 10x is introduced to the femoral artery from the radial artery as in the first embodiment, the surgeon checks the position of the distal portion of the guide wire 120x by radiography and the like, and while doing this, the surgeon introduces the catheter assembly 10x into the femoral artery as the target site through the radial artery, the brachial artery, the subclavian artery, the brachiocephalic artery, the thoracic aorta, the abdominal aorta, the common iliac artery, and the external iliac artery. At this time, in the catheter assembly 10x, the tubular body 80x is disposed inside the outer catheter body 40x. The tubular body 80x is positioned in a gap between the outer surface of the guide wire 120x to be inserted into the inner catheter lumen 83x and the inner surface of the outer catheter body 40x, and the outer diameter of the tubular body 80x is smaller in the distal portion of the tubular body 80x than in the proximal portion of the tubular body 80x. Accordingly, with the catheter assembly 10x, the surgeon can reduce a step difference formed between the outer surface of the outer catheter body 40x and the outer surface of the guide wire 120x, while bringing the distal end of the outer catheter body 40x into contact with the outer surface of the tubular body 80x. As a result, the surgeon can suppress the damage of a blood vessel as much as possible, and inhibit rolling of the outer catheter body 40x that is caused when the distal end of the outer catheter body 40x receives resistance from the blood vessel. Moreover, since the distal end (distal-most end) of the tubular body distal portion 82x whose outer diameter is reduced toward the distal end of the tubular body distal portion 82x is positioned distally of the distal end (distal-most end) of the outer catheter body 40x, the tubular body distal portion 82x smoothly comes into contact with the blood vessel, and accordingly, damage of the blood vessel can be suppressed as much as possible.

In the assembled state, within the cross section of the distal end of the outer catheter body 40x that is orthogonal to the axis of the outer catheter body 40x, the thickness of the tubular body 80x in the radial direction is larger than the thickness of the outer catheter body 40x in the radial direction. Therefore, with the catheter assembly 10x, the surgeon can reduce a step difference formed between the outer surface of the outer catheter body 40x and the outer surface of the tubular body 80x, and further suppress the damage of the blood vessel.

Moreover, in the assembled state, the length L1 between the distal end of the tubular body 80x and the distal end of the outer catheter body 40x in the axial direction is smaller than the length L2 between the distal end of the outer catheter body 40x and the proximal end of the tubular body 80x in the axial direction. Accordingly, the length L2 is sufficient for the tubular body 80x to be accommodated inside the outer catheter 20x, whereby the tubular body 80x can be inhibited from kinking in the distal area of the outer catheter body 40x. As a result, when inserting the catheter assembly 10x into a blood vessel, the surgeon can more safely inserts the catheter assembly into the blood vessel, while securing sufficient pushability or sufficiently transmitting torque to the distal side.

In the assembled state, the proximal end of the tubular body 80x is positioned proximally of the distal end (distal-most end) of the rigidity uniform portion 402x of the outer catheter body 40x. Accordingly, the proximal end of the tubular body 80x is not positioned in the middle of the rigidity transition portion 401x in which the rigidity is reduced toward the distal end, and the transition of rigidity of the outer catheter body 40x can be excellently maintained. As a result, when inserting the catheter assembly 10x into a blood vessel, the surgeon can more safely insert the catheter assembly into the blood vessel, while securing sufficient pushability or sufficiently transmitting torque to the distal side.

Figure 18:
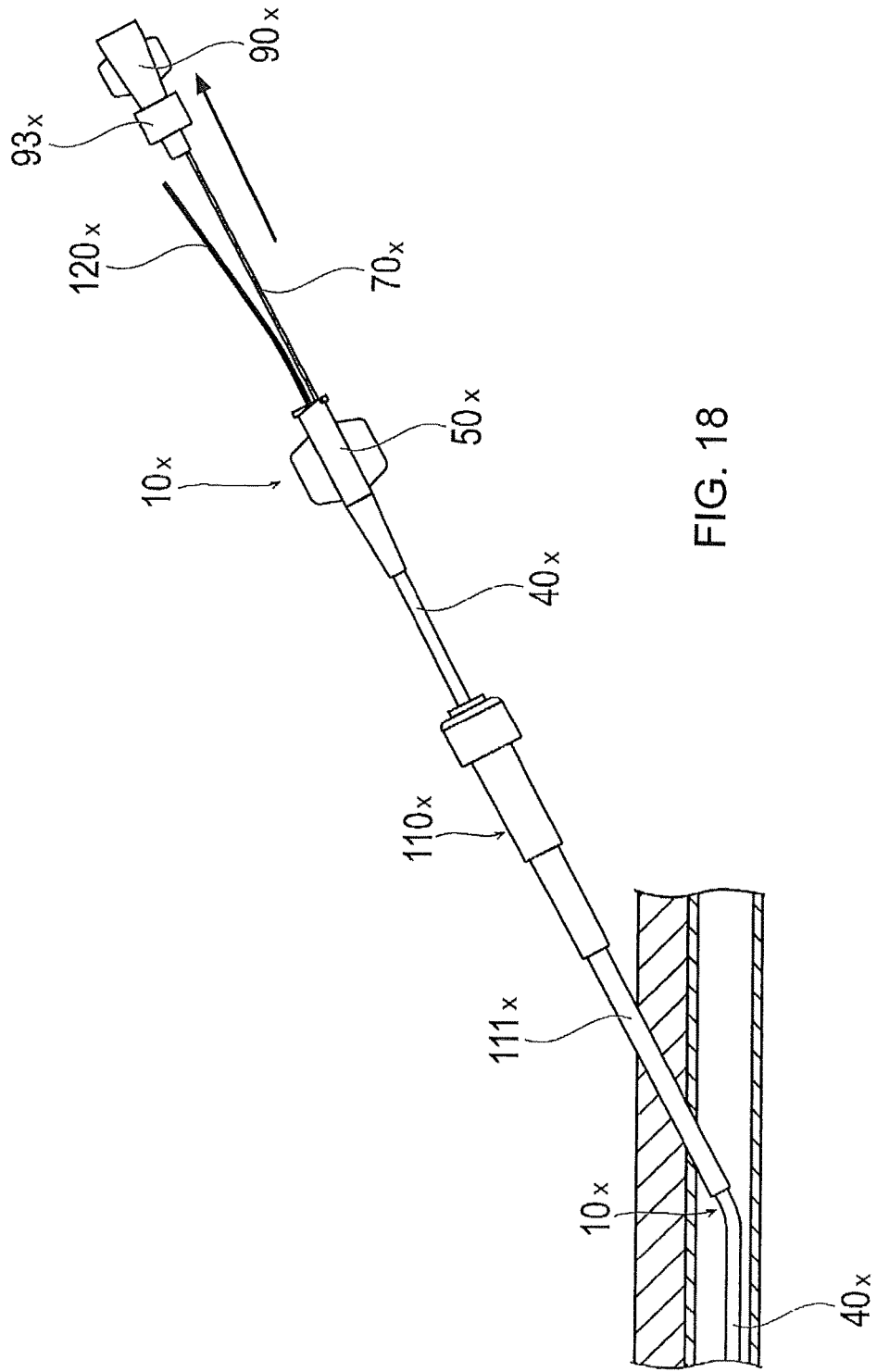
FIG. 18 is a third illustrative view showing a state where the inner catheter is pulled out of the catheter assembly (an inner catheter and an outer catheter) used in the treatment method according to the third embodiment.
Figure 19:
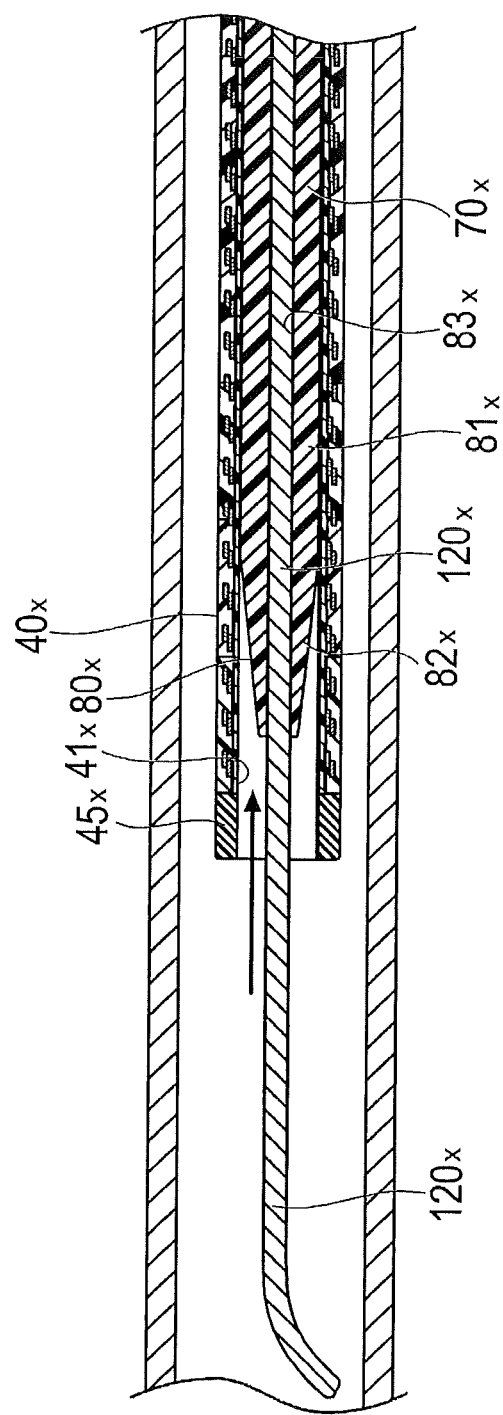
FIG. 19 is a fourth illustrative view showing the way the distal portion of the catheter assembly used in the treatment method according to the third embodiment operates. This is a schematic cross-sectional view showing a state where the inner catheter is pulled out of the catheter assembly (an inner catheter and an outer catheter).

After the distal end of the catheter assembly 10x reaches the target site, the surgeon rotates the screwing portion 93x to disconnect the helical groove 99x from the helical bump or enlargement 53x. Moreover, as shown in FIGS. 18 and 19, the surgeon pulls the inner catheter 30x out of the outer catheter 20x while leaving the outer catheter 20x and the guide wire 120x inside the blood vessel. At this time, the tubular body 80x disposed at the distal side of the shaft 70x of the inner catheter 30x includes an inner catheter lumen 83x, which opens to the outside in the distal portion and the proximal portion of the tubular body 80x and enables the guide wire 120x to be inserted in the inner catheter lumen 83x. Furthermore, at the distal side of the tubular body 80x, the guide wire 120x is positioned not in the inside of but in the outside of the inner catheter 30x. Therefore, when the inner catheter hub 90x moves proximally to a position on the proximal side of the proximal end (proximal-most end) of the guide wire 120x, the guide wire 120x is pulled out of the inner catheter hub lumen 94x toward the distal side. As a result, except for the inner catheter lumen 83x of the tubular body 80x, the guide wire 120x is positioned outside the inner catheter 30x. That is, the guide wire 120x is positioned exterior of the shaft 70x. Accordingly, even though the guide wire 120x is not excessively lengthened, the inner catheter 30x can be withdrawn along the guide wire 120x (inner catheter withdrawal step). Specifically, at the time of withdrawal of the inner catheter 30x, the catheter assembly 10x maintains a state in which the guide wire 120x is exposed without being hidden in the inner catheter 30x at the surgeon's side where the assembly is operated. Therefore, a high degree of operability of the guide wire 120x is obtained.

After the inner catheter 30x is completely pulled out of the outer catheter 20x, by using the helical bump or enlargement 53x of the outer catheter hub 50x, the surgeon connects a general Y-connector 130x, which has a connection portion 133x having a structure similar to the screwing portion 93x and the cylindrical portion 97x (see FIG. 14) of the aforementioned inner catheter hub 90x, to the outer catheter hub 50x as shown in FIG. 20. The Y-connector 130x has a first port 131x that includes a hemostasis valve and a second port 132x that is for injecting a contrast agent and the like. By connecting the connection portion 133x to the outer catheter hub 50x, communication between the outer catheter hub lumen 54x and the first port 131x as well as the second port 132x is established. When the Y-connector 130x is connected to the outer catheter hub 50x, the guide wire 120x, which is exposed to the proximal side from the outer catheter hub opening portion 55x, is brought out of the first port 131x through the hemostasis valve. The second port 132x can be connected to a contrast agent-containing syringe or the like. When pushed out of the syringe or the like, the contrast agent can pass through the outer catheter hub lumen 54x and the outer catheter lumen 41x and can be discharged from the distal end of the outer catheter body 40x. The liquid accommodated in the syringe or the like is not limited to the contrast agent and may be a drug or physiological saline.

Figure 21:
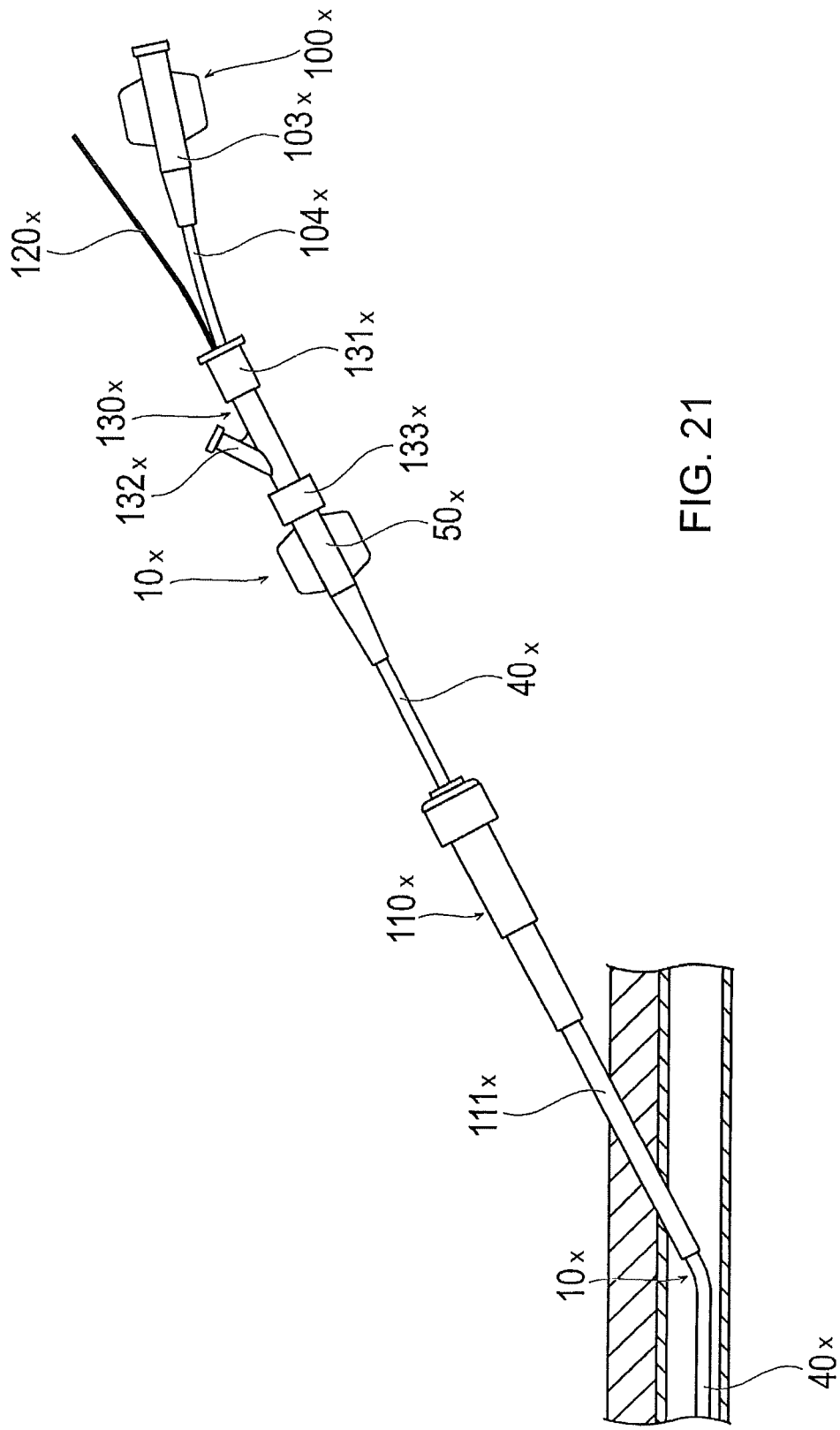
FIG. 21 is a sixth illustrative view of the treatment method following FIG. 20. This is a schematic cross-sectional view showing a state where a balloon catheter is introduced into a blood vessel through the outer catheter, after the inner catheter is pulled out of the catheter assembly used in the treatment method according to the third embodiment.

Next, the surgeon inserts the proximal end of the guide wire 120x from the distal side of the guide wire lumen 102x of the balloon catheter 100x, and then inserts the balloon catheter 100x into the first port 131x along the guide wire 120x as shown in FIG. 21. Thereafter, the surgeon moves the balloon catheter 100x in the outer catheter lumen 41x toward the distal end and causes the balloon 101x to protrude to the distal side from the outer catheter body 40x. Subsequently, the surgeon causes the balloon catheter 100x to advance, until the surgeon confirms a state where the balloon 101x has been delivered to a position corresponding to the stenosed portion as a treatment target in the blood vessel under radiography (device advance step). Next, the surgeon connects a syringe or the like that accommodates a fluid for dilation to the balloon catheter hub 103x, supplies the fluid for dilation to the balloon 101x through the lumen for dilation, thereby dilating the balloon 101x as shown in FIG. 22. In this manner, the surgeon can provide treatment in which the balloon 101x is dilated so as to expand, for example, a stenosed portion (target site) as a treatment target in the blood vessel by using the balloon 101x (treatment step).

Thereafter, the fluid for dilation is discharged out of the balloon 101x through the lumen for dilation, whereby the balloon 101x contracts. The surgeon then withdraws the balloon catheter 100x and the guide wire 120x from the outer catheter 20x.

The treatment performed through the outer catheter 20x is not limited to the treatment performed using the balloon catheter 100x. For example, a stent may be disposed on the outer surface of the balloon 101x. If the stent is disposed on the outer surface of the balloon 101x, when the balloon 101x is dilated, the stent expands while undergoing plastic deformation. When the balloon 101x is contracted, the stent having undergone plastic deformation remains on the inner wall surface of the blood vessel without being contracted, and the blood vessel can be maintained excellently in the state of being expanded by the stent. Moreover, through the outer catheter 20x, insertion or withdrawal of an elongated device/substance such as a catheter other than the balloon catheter 100x, an endoscope, an ultrasonic probe, or a temperature sensor can be performed, or alternatively, injection of various liquids such as a contrast agent (X-ray contrast agent), a drug solution, and physiological saline can be performed. Thereafter, the outer catheter 20x is pulled out of the sheath 111x, the sheath 111x is pulled out of the radial artery, and the blood from the portion punctured by the sheath 111x is stanched to complete the procedure.

As described above, particularly when a blood vessel of a lower limb, such as the femoral artery, is treated from a blood vessel of an arm, such as the radial artery, by a TRI technique, the surgeon has to use a long catheter assembly and guide wire since a distance between the insertion site of the catheter assembly and the treatment site is long. Consequently, when the surgeon uses an over-the-wire type inner catheter, it takes a long time for the surgeon to withdraw the inner catheter. The inner catheter 30x of the catheter assembly 10x disclosed here is a rapid exchange-type catheter. Accordingly, it is easy for the surgeon to withdraw the inner catheter 30x while leaving the outer catheter 20x and the guide wire inside the body lumen. Therefore, the catheter assembly 10x disclosed here by way of example is suitable for the case where a blood vessel of a lower limb, such as the femoral artery, is treated from a blood vessel of an arm, such as the radial artery.

The intervention device (catheter assembly 10x) used in the treatment method of the third embodiment is not limited to the form of the catheter assembly 10x. For example, the catheter assembly 10x may be in the form of a seventh modified example described below. A catheter assembly 140x according to the seventh modification example differs from the catheter assembly used in the treatment method of the third embodiment, only in terms of the construction of an inner catheter 150x. Moreover, the portions of the catheter assembly 10x used in the treatment method according to the third embodiment that are similar to those in the embodiments described above are identified by a common reference numeral and a detailed description of such aspects is not repeated.

Figure 23:
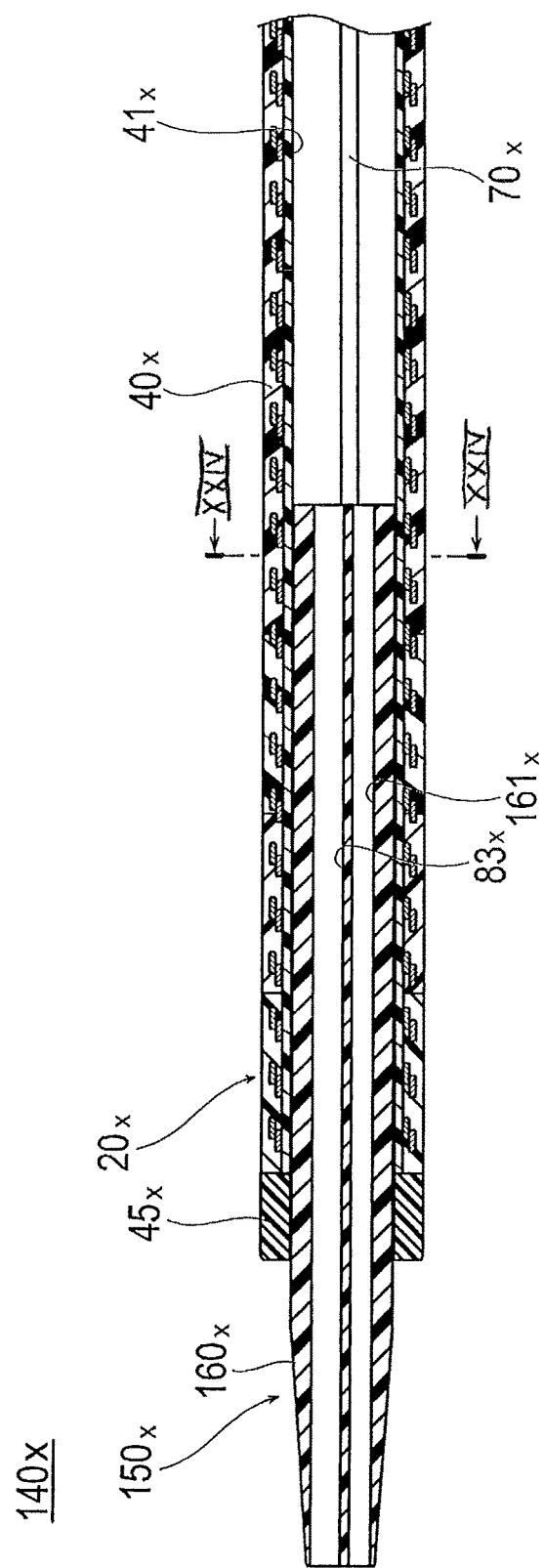
FIG. 23 shows a seventh modification example of the catheter assembly used in the treatment method according to the third embodiment. This is a vertical cross-sectional view showing the distal portion of the catheter assembly according to the seventh modification example.
Figure 24:
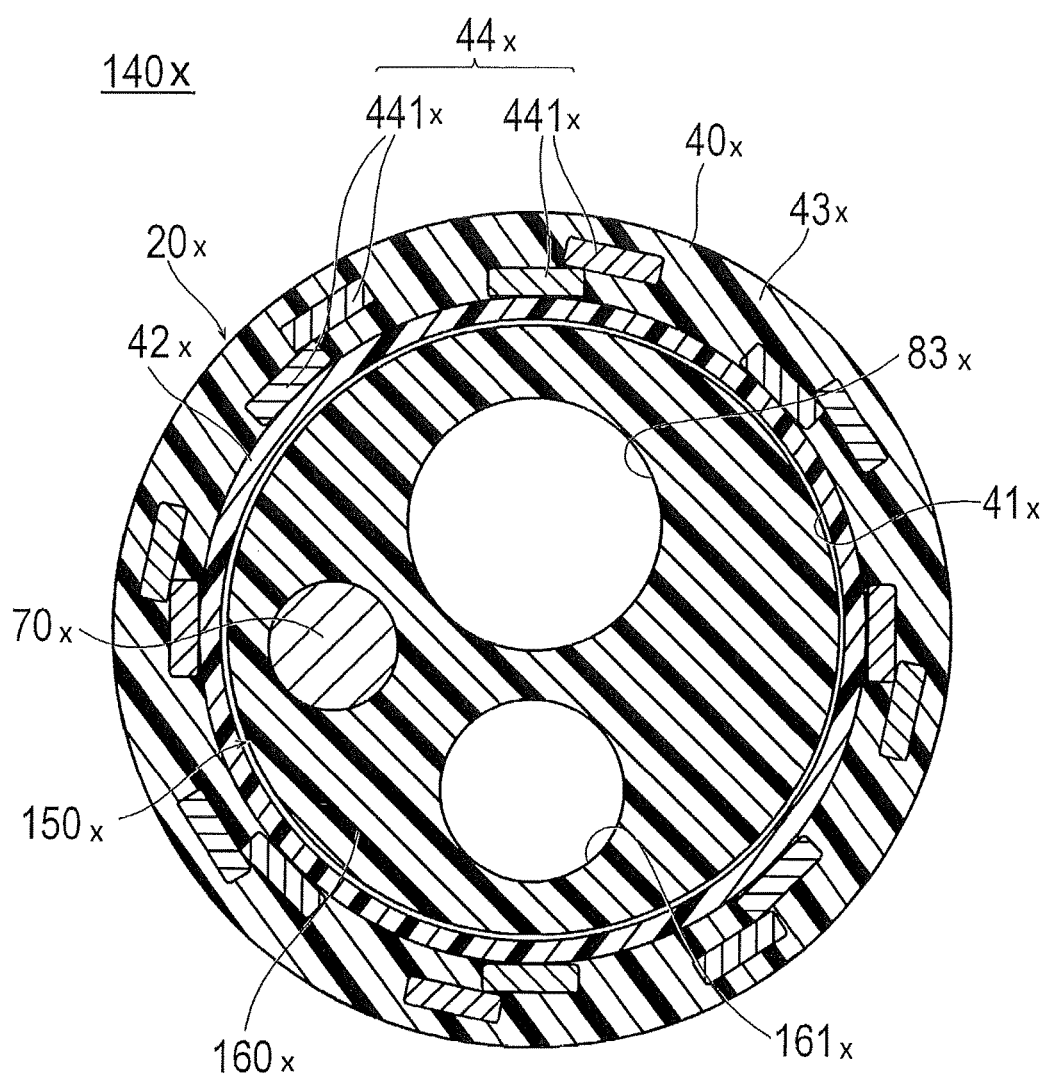
FIG. 24 is a horizontal cross-sectional view taken along the section line XXIV-XXIV in FIG. 23.

As shown in FIGS. 23 and 24, the tubular body 160x of the inner catheter 150x of the seventh modified example includes, in addition to the inner catheter lumen 83x into which a guide wire is inserted, a second inner catheter lumen 161x that penetrates the tubular body 160x from the distal end to the proximal end. Moreover, the shaft 70x is fixed to a position different from the portion in which the inner catheter lumen 83x and the second inner catheter lumen 161x of the tubular body 160x are formed. The second inner catheter lumen 161x serves as a flow path through which a liquid such as a contrast agent or physiological saline flows. It is preferable for the inner diameter of the inner catheter lumen 83x to be larger than the inner diameter of the second inner catheter lumen 161x. If the above configuration is adopted, when a guide wire is inserted into the inner catheter lumen 83x of the tubular body 160x, since the inner diameter of the second inner catheter lumen 161x is smaller than the size of the inner catheter lumen 83x which has an inner diameter approximately the same as the outer diameter of the guide wire, the risk that the surgeon may accidentally insert the guide wire into the second inner catheter lumen 161x is reduced. Moreover, in the assembled state in which an inner catheter hub 170x is connected to the outer catheter hub 50x, it is preferable for the tubular body 160x to have a tapered portion of which the outer diameter increases toward the proximal side from the distal end of the tubular body 160x, with the tapered portion located (entirely in the illustrated embodiment) on the distal side of the distal end (distal-most end) of the outer catheter 20x. At this time, it is more preferable for the tubular body 160x to be configured so that the inner catheter lumen 83x penetrates the tubular body 160x from the distal end of the tubular body 160x to the proximal end of the tubular body 160x, and the second inner catheter lumen 161x penetrates the tubular body 160x from the tapered portion of the tubular body 160x to the proximal end of the tubular body 160x. A distal opening of the inner catheter lumen 83x is positioned in a portion closer to a distal opening of the second inner catheter lumen 161x than to the distal side. If the above constitution is adopted, when the guide wire is inserted into the inner catheter lumen 83x of the tubular body 160x, the risk that the surgeon may accidentally insert the guide wire into the second inner catheter lumen 161x can be reduced. In addition, in the catheter assembly 140x, the inner catheter lumen 83x into which the guide wire is inserted is formed in a portion near the center of the tubular body 160x. Accordingly, operability of the guide wire can be improved.

Figure 25:
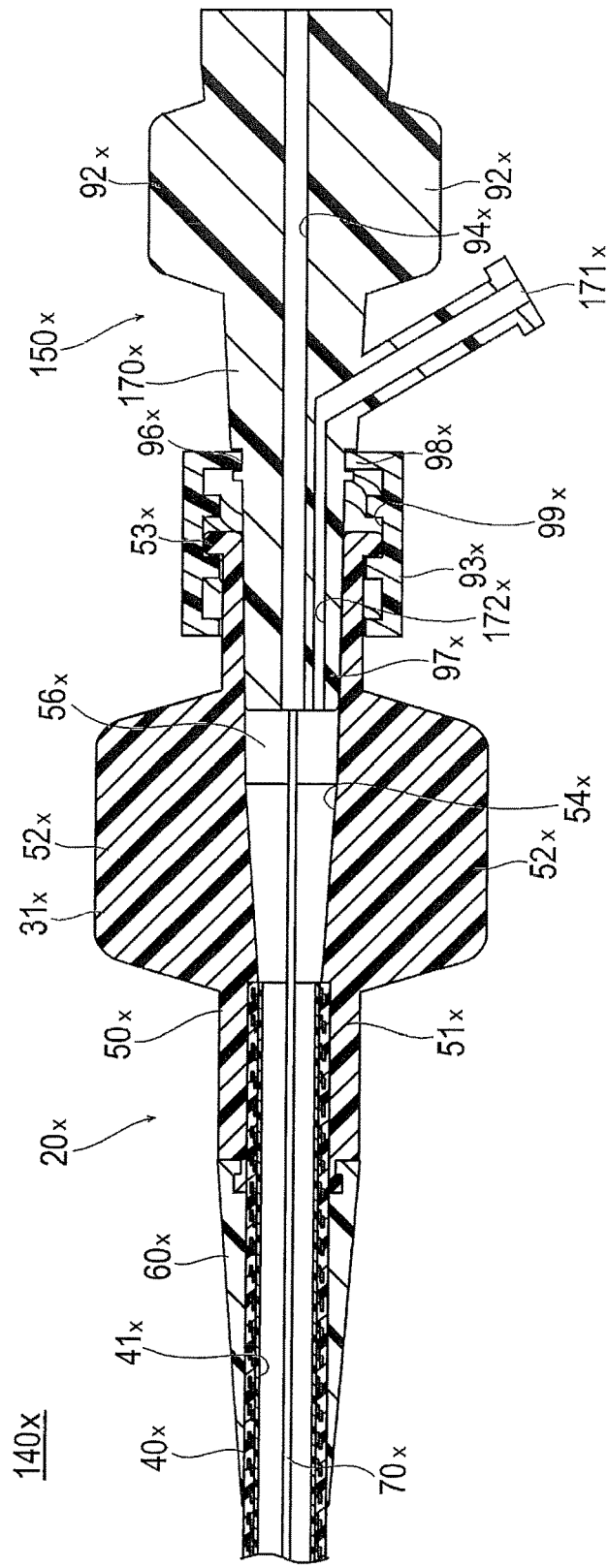
FIG. 25 is a vertical cross-sectional view showing the proximal portion of the catheter assembly according to a seventh modified example.

As shown in FIG. 25, in the inner catheter hub 170x of the inner catheter 150x, a port 171x that is for injecting a liquid such as a contrast agent or physiological saline is formed. Moreover, the port 171x includes a second inner catheter hub lumen 172x that extends to the distal surface of the cylindrical portion 97x of the inner catheter 150x. Accordingly, in the inner catheter hub 170x, the inner catheter hub lumen 94x into which the guide wire is inserted and the second inner catheter hub lumen 172x are formed. The second inner catheter hub lumen 172x can function as a flow path through which a liquid such as a contrast agent or physiological saline can flow.

Next, the action of the catheter assembly 140x according to the seventh modified example will be described.

In the catheter assembly 140x according to the seventh modified example, the second inner catheter lumen 161x is formed in the tubular body 160x of the inner catheter 150x as shown in FIGS. 23 and 24, and the second inner catheter hub lumen 172x is formed in the inner catheter hub 170x as shown in FIG. 25. Accordingly, in a state where the guide wire is inserted into the inner catheter lumen 83x and the inner catheter hub lumen 94x, when the port 171x is connected to a syringe or the like that accommodates a liquid such as a contrast agent, physiological saline, or a drug, and the liquid is injected into the catheter, the liquid, which has been injected into the outer catheter body 40x through the second inner catheter hub lumen 172x, flows to the distal end through the outer catheter lumen 41x and then is discharged to the distal side (end) of the catheter assembly 140x through the second inner catheter lumen 161x of the tubular body 160x. At this time, the liquid is delivered to the distal end by using the outer catheter lumen 41x which is positioned at the outside of the inner catheter 150x and has a relatively large inner diameter until the liquid reaches the second inner catheter lumen 161x. Therefore, pressure loss is reduced, and the liquid can be easily pushed out by a small force. Accordingly, the catheter assembly 140x is particularly effective for injecting a liquid with high viscosity, such as a contrast agent.

A catheter assembly 180x according to an eighth modified example used in the treatment method of the third embodiment differs from the catheter assembly 10x used in the treatment method of the third embodiment, only in terms of the configuration or construction of an inner catheter 190x. A catheter assembly 180x according to the eighth modified example differs from the catheter assembly used in the treatment method of the third embodiment, only in terms of the construction of an inner catheter 150x. The portions of the catheter assembly 10x, 140x used in the treatment method according to the third embodiment that are similar to those in the embodiments described above are identified by a common reference numeral and a detailed description of such aspects is not repeated.

Figure 26:
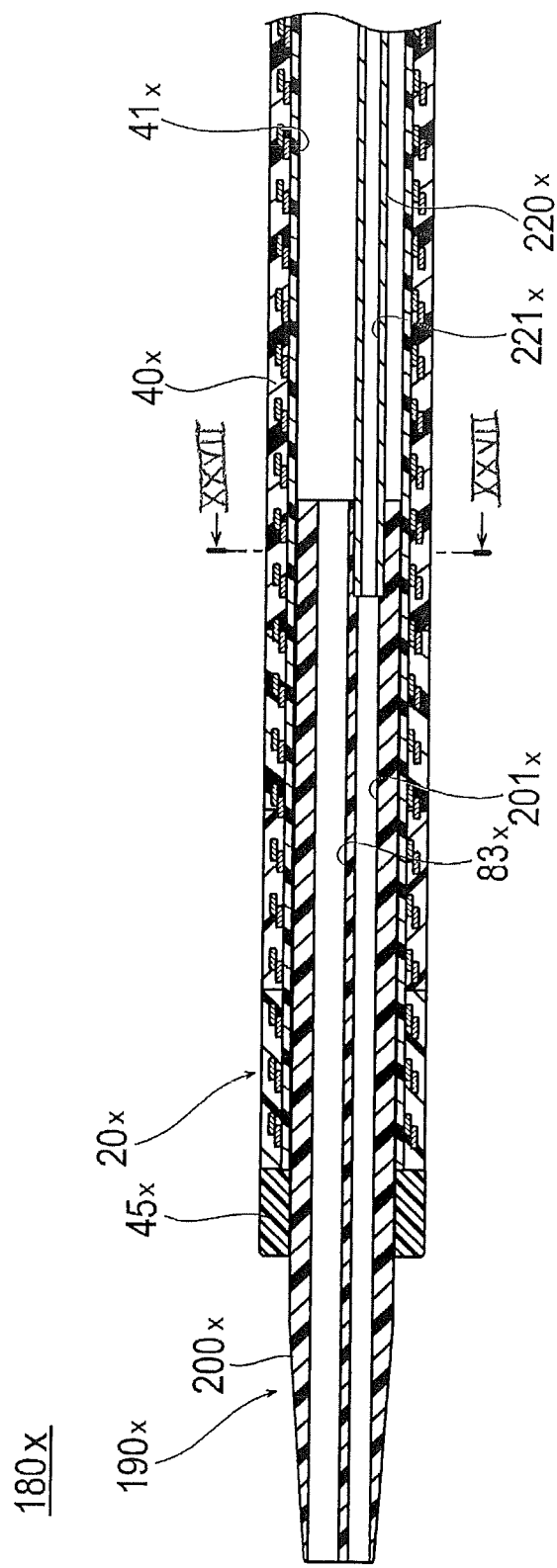
FIG. 26 shows an eighth modified example of the catheter assembly used in the treatment method according to the third embodiment. This is a vertical cross-sectional view showing the distal portion of the catheter assembly according to the eighth modified example.
Figure 27:
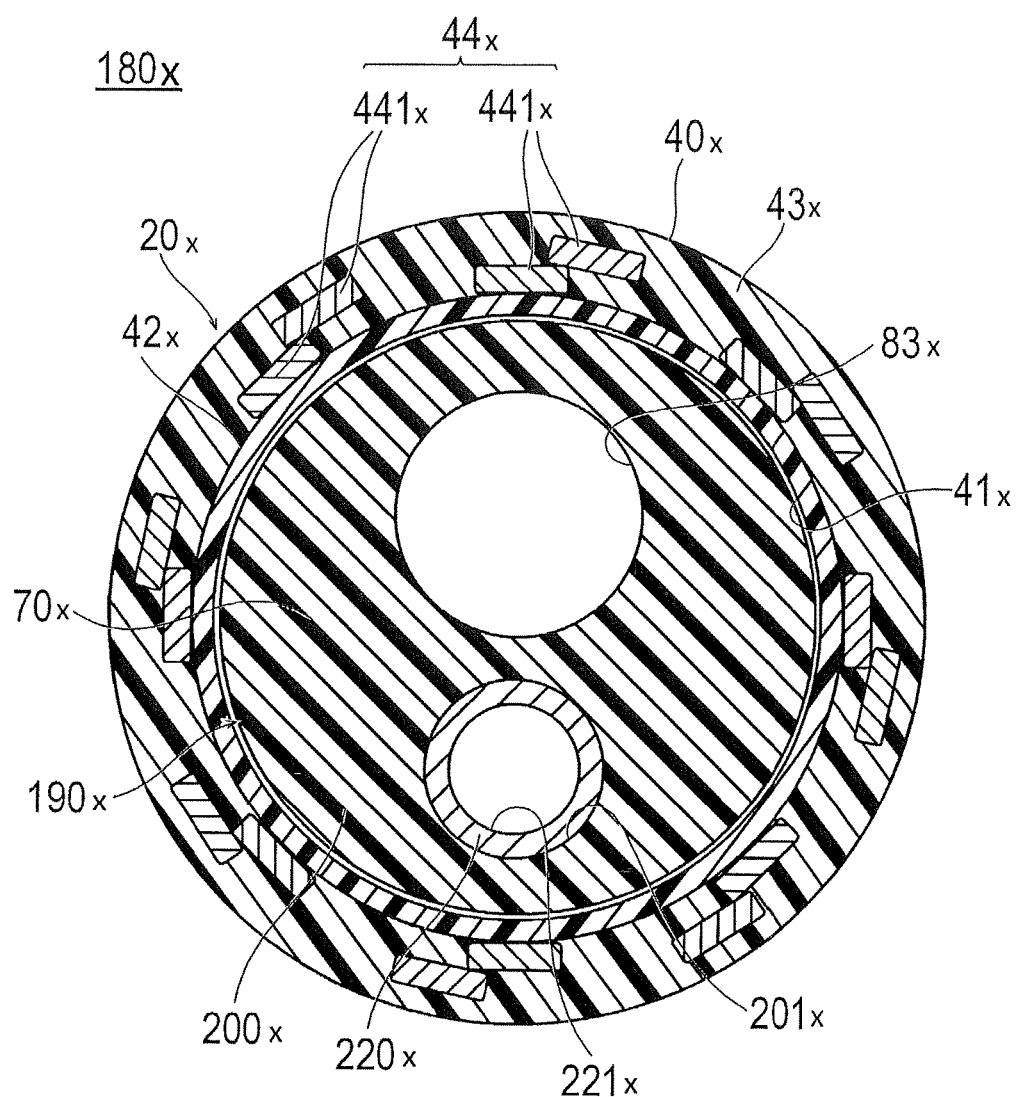
FIG. 27 is a horizontal cross-sectional view taken along the section line XXVII-XXVII of FIG. 26.

As shown in FIGS. 26 and 27, in a tubular body 200x of the inner catheter 190x in the eighth modified example, in addition to the inner catheter lumen 83x into which the guide wire 120x is inserted, a second inner catheter lumen 201x that penetrates (passes through) the tubular body 200x from the distal end of the tubular body 200x to the distal end thereof is formed.

Figure 28:
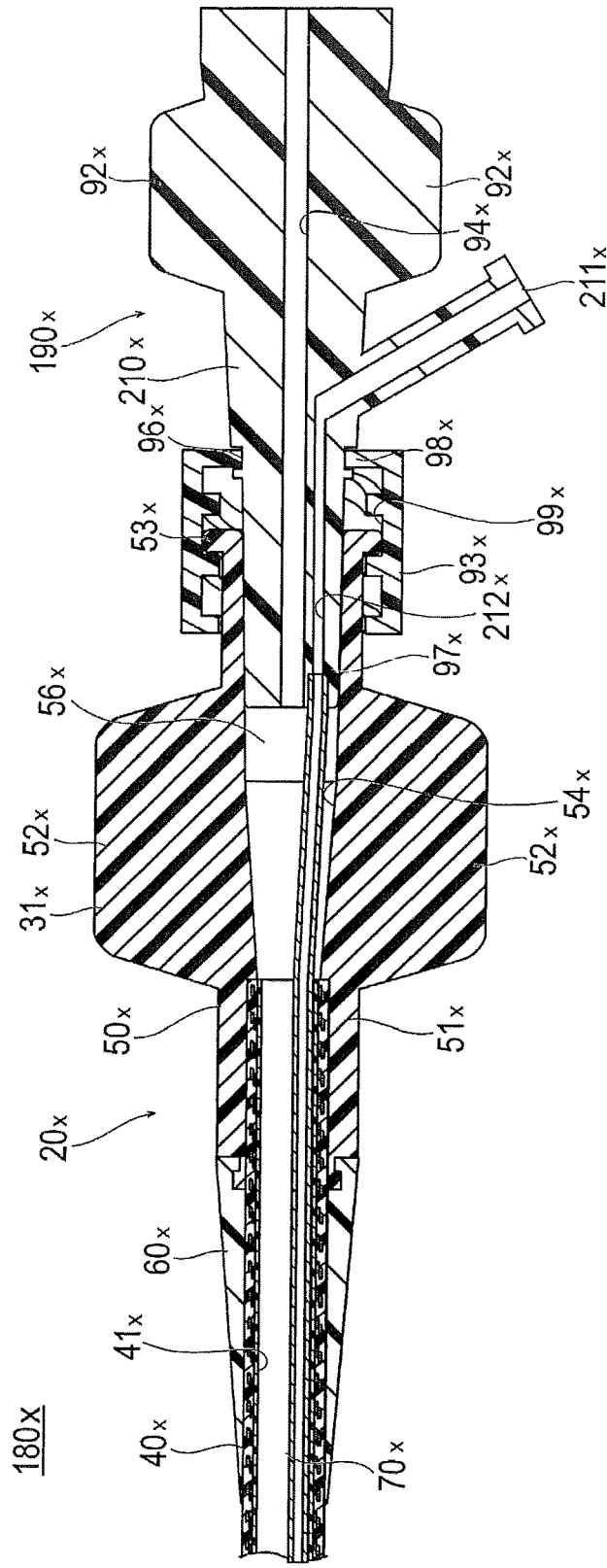
FIG. 28 is a vertical cross-sectional view showing the proximal portion of the catheter assembly according to the eighth modified example.
Figure 29:
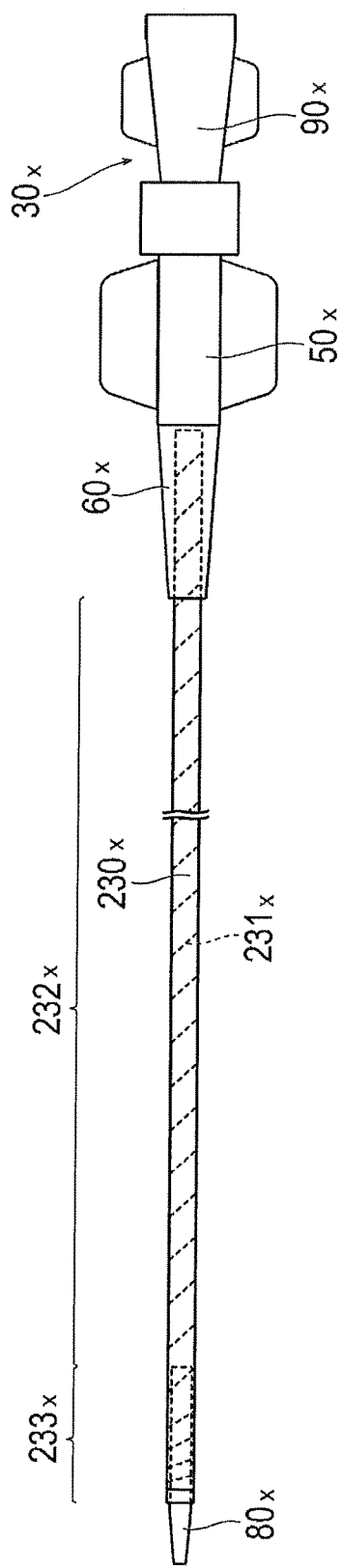
FIG. 29 is a plan view of a ninth modified example of the catheter assembly used in the treatment method according to the third embodiment.

In an inner catheter hub 210x of the inner catheter 190x, a port 211x for injecting a liquid such as a contrast agent or physiological saline is formed as shown in FIG. 28. Moreover, in the port 211x, a second inner catheter hub lumen 212x that extends to the distal surface of the cylindrical portion 97x of the inner catheter 190x is formed.

A shaft 220x of the inner catheter 190x is a tubular body in which a shaft lumen 221x that penetrates the shaft in the axial direction is formed. The distal portion of the shaft 220x is fixed to the tubular body 200x as shown in FIGS. 26 and 27 such that the shaft lumen 221x is in communication with the second inner catheter lumen 201x. Moreover, the proximal portion of the shaft 220x is fixed to the cylindrical portion 97x of the inner catheter hub 210x as shown in FIG. 28 such that the shaft lumen 221x is in communication with the second inner catheter hub lumen 212x. The second inner catheter hub lumen 212x, the shaft lumen 221x, and the second inner catheter lumen 201x function as a flow path through which a liquid such as a contrast agent, physiological saline, or a drug flows.

Next, the action of a catheter assembly 180x according to the eighth modified example is described.

In the catheter assembly 180x according to the eighth modified example, the second inner catheter lumen 201x is formed in the tubular body 200x of the inner catheter 190x as shown in FIGS. 26 and 27. Moreover, as shown in FIG. 28, the shaft lumen 221x is formed in the shaft 220x, and the second inner catheter hub lumen 212x is formed in the inner catheter hub 210x. The second inner catheter lumen 201x, the shaft lumen 221x, and the second inner catheter hub lumen 212x are in communication with one another. Accordingly, in a state where a guide wire is inserted into the inner catheter lumen 83x and the inner catheter hub lumen 94x, when a syringe accommodating a liquid such as a contrast agent, physiological saline, or a drug is connected to the port 211x, and the liquid is injected, the liquid is discharged to the distal side of the catheter assembly 180x through the second inner catheter hub lumen 212x, the shaft lumen 221x, and the second inner catheter lumen 201x. At this time, the liquid does not flow inside the outer catheter lumen 41x into which the guide wire is inserted. Accordingly, the liquid can be effectively discharged to the distal side of the catheter assembly 180x without being interrupted by the guide wire.

The aforementioned catheter assembly used in the treatment method of the third embodiment is not limited to the above catheter assembly, and can be modified in various ways by those skilled in the art within the technical idea disclosed here. For example, as a ninth modified example shown in FIG. 29, an outer catheter body 230x may be provided with a reinforcing member in which a helical slit 231x is formed between an inner layer and an outer layer. Moreover, in the proximal portion of the outer catheter body 230x, a slit 231x is formed at a certain pitch so as to form a rigidity uniform portion 232x (a portion of uniform rigidity throughout). In addition, the distal portion of the outer catheter body 230x includes a rigidity transition portion 233x in which the pitch of the slit 231x is gradually reduced toward the distal end. In the rigidity uniform portion 232x formed as above, the rigidity is uniform in the axis direction, and in the rigidity transition portion 233x, the rigidity is reduced toward the distal end. Furthermore, the proximal end (proximal-most end) of the tubular body 80x is on the proximal side of the distal end (distal-most end) of the rigidity uniform portion 232x. If the above construction or configuration is adopted, the proximal end of the tubular body 80x is not positioned in the middle of the rigidity transition portion 233x, and transition of rigidity of the outer catheter body 230x can be excellently maintained. Accordingly, when inserting the catheter assembly into the body lumen, the surgeon can more safely insert the catheter assembly into the body lumen, while sufficiently securing pushability or sufficiently transmitting torque to the distal side.

In addition, at least one of the outer catheter body and the inner catheter body may form a curve.

The use of the catheter assembly disclosed here by way of various examples is not particularly limited as long as it is used by being inserted into the body lumen. Accordingly, the catheter assembly may be, for example, a catheter introducer in which the outer catheter functions as a sheath and the inner catheter (shaft) functions as a dilator. The body lumen is not limited to a blood vessel and may be, for example, a vessel, the ureter, the bile duct, the fallopian tube, the hepatic duct, and the like. Particularly, in recent years, it has been increasingly necessary for the surgeon to deliver the catheter assembly to a blood vessel of a lower limb through the radial artery or the subclavian artery by using the TRI technique. When the blood vessel of a lower limb is taken as a treatment site, for example, the iliac artery or the femoral artery becomes the blood vessel as a treatment target. In this case, a distance between the site where the catheter assembly is inserted into the blood vessel and the treatment site inside the blood vessel is rather long, and accordingly, the surgeon needs to use a long guide wire, inner catheter, and outer catheter. Therefore, when the blood vessel of a lower limb is treated by the TRI technique, the catheter assembly according to the disclosure here that inhibits the guide wire from being excessively lengthened is suitable.

The number of catheters constituting the catheter assembly is not particularly limited as long as the assembly is constituted of two or more catheters. Therefore, for example, the catheter assembly may include another catheter outside the outer catheter, or may include another catheter between the outer catheter and the inner catheter.

The detailed description above describes embodiments of a catheter assembly and method representing examples of the catheter assembly and method disclosed here. The invention is not limited, however, to the precise embodiments and variations described. Various changes, modifications and equivalents can effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A treatment method for treating a treatment target of at least one lower limb of a patient's body, the patient's body including an aorta, the method comprising:

introducing a catheter assembly into a blood vessel of an arm of the patient's body, the catheter assembly possessing a distal end and comprising a first catheter possessing a lumen and a second catheter possessing a lumen, the second catheter being positioned in the lumen of the first catheter, the first and second catheters each possessing a distal end;

the introducing of the catheter assembly into the blood vessel including maintaining a portion of the catheter assembly exposed outside the body;

delivering the catheter assembly to a predetermined position of one lower limb of the at least one lower limb so that the distal ends of both the first and second catheters pass through the aorta by operating the portion of the catheter assembly that is exposed outside the body;

after delivering the catheter assembly to the predetermined position of the one lower limb, advancing a treatment device through the first catheter and toward the treatment target; and treating the treatment target using the treatment device.

2. The treatment method according to claim 1, further comprising, before the advancing of the treatment device through the first catheter and toward the treatment target:

advancing the distal end of the second catheter, or a distal end of a third catheter introduced after withdrawal of the second catheter from the first catheter, near the treatment target through the first catheter; and the advancing of the treatment device through the first catheter and toward the treatment target comprising advancing the treatment device through the lumen of the second catheter or through a lumen in the third catheter.

3. The treatment method according to claim 1, wherein the one lower limb is a first lower limb, the treatment method further comprising, after the treating of the treatment target:

retreating the distal end of the first catheter to a connection position at which a blood vessel of the first lower limb and a blood vessel of a second lower limb are connected to each other;

delivering the first catheter to a predetermined position of the second lower limb from the connection position after the retreating of the distal end of the first catheter to the connection position; and advancing an individual site treatment device to a treatment target of the second lower limb by moving the individual site treatment device through the first catheter after delivering the first catheter to the predetermined position of the second lower limb; and treating the treatment target of the second lower limb by operation of the individual site treatment device.

4. The treatment method according to claim 3, further comprising, before treating the treatment target of the second lower limb by operation of the individual site treatment device:

advancing to an individual site, in the second lower limb near the treatment target of the second lower limb, the distal end of the second catheter or a distal end of a third catheter, which is introduced into the first catheter after withdrawing the second catheter from the first catheter, through the first catheter; and wherein the advancing of the individual site treatment device to the treatment target of the second lower limb comprises advancing the individual site treatment device through the lumen of the second catheter or the third catheter.

5. The treatment method according to claim 1, further comprising introducing a sheath having an outer diameter equal to or smaller than 2.8 mm into the blood vessel of the arm of the patient's body, the introducing of the catheter assembly into the blood vessel of the arm of the patient's body comprising introducing the catheter assembly into a lumen of the sheath.

6. The treatment method according to claim 1, wherein the treatment target is located in a blood vessel closer to a peripheral side than to a popliteal artery in the one lower limb, and the delivering of the catheter assembly to the predetermined position of the one lower limb includes delivering the distal end of the catheter assembly to a femoral artery or an iliac artery, and during the advancing of the treatment device, the treatment device is sent to the femoral artery from the catheter assembly, and the treatment device is advanced to the popliteal artery.

7. The treatment method according to claim 1, wherein the treatment target is located in a blood vessel closer to a peripheral side than to a popliteal artery in the one lower limb, and the delivering of the catheter assembly to the predetermined position of the one lower limb includes positioning the distal end of the catheter assembly in the popliteal artery or in the blood vessel at the peripheral side.

8. The treatment method according to claim 1, wherein the treatment target is present near a knee, near a calf, or near an ankle of the patient.

9. A treatment method for treating a treatment target of at least one lower limb in a body of a patient, the patient's body including an aorta, the method comprising:

inserting a guide wire into a catheter assembly, the catheter assembly comprising an inner catheter and an outer catheter each possessing a lumen and a distal end, the inner catheter being disposed in the lumen of the outer catheter with the distal end of the inner catheter protruding distally beyond the distal end of the outer catheter, the inserting of the guide wire including inserting the guide wire into the lumen of the inner catheter while the inner catheter is disposed in the lumen of the outer catheter;

introducing the guide wire into a blood vessel of an arm of the patient's body, and introducing the catheter assembly into the blood vessel of the arm by guiding the catheter assembly along the guide wire;

delivering a distal ends of the inner and outer catheters through the aorta and to a predetermined position of one lower limb of the at least one lower limb by operating a portion of the catheter assembly that is exposed outside the patient's body;

withdrawing the inner catheter from the lumen of the outer catheter while the outer catheter and the guide wire remain inside the blood vessel after delivering the distal ends of the inner and outer catheters through the aorta and to the predetermined position of the one lower limb;

introducing a treatment device for treating the treatment target into the blood vessel and along the guide wire after the withdrawing of the inner catheter, and advancing the treatment device to the treatment target through the outer catheter; and treating the treatment target using the treatment device.

10. The treatment method according to claim 9, wherein the outer catheter includes a tubular outer catheter body and an outer catheter hub disposed at a proximal end of the outer catheter body, the lumen of the outer catheter passing through both the outer catheter body and the outer catheter hub;

wherein the inner catheter includes an inner catheter body positioned in the lumen in the outer catheter body, and an inner catheter hub positioned in a proximal end of the inner catheter body and connected to the outer catheter hub; and further comprising, before the inserting of the guide wire into the catheter assembly, disposing the inner catheter body in the lumen in the outer catheter body, and connecting the inner catheter hub to the outer catheter hub.

11. The treatment method according to claim 10, wherein the inner catheter body includes a shaft and a tubular body, the shaft possessing a distal end connected to the tubular body, the lumen of the inner catheter including a first inner catheter lumen passing through the tubular body, the tubular body and the outer catheter body both possessing respective distal-most ends; and during the inserting of the guide wire into the catheter assembly, the distal-most end of the tubular body is positioned distally of the distal-most end of the outer catheter body, and a proximal-most end of the tubular body is positioned in the lumen of the outer catheter.

12. The treatment method according to claim 11, wherein the tubular body includes a second inner catheter lumen that opens at opposite ends in a distal portion and a proximal portion of the tubular body; and further comprising, during the delivering of the distal ends of the inner and outer catheters through the aorta and to the predetermined position of the one lower limb, injecting a fluid through the inner catheter hub of the catheter assembly such that the fluid is injected into the blood vessel through the second inner catheter lumen.

13. A treatment method for treating a treatment target in a lower limb of a patient's body, the patient's body including an aorta, the method comprising:

introducing a catheter assembly into a blood vessel of an arm of the patient's body, the catheter assembly comprising a first catheter possessing a lumen extending throughout a length of the first catheter and a second catheter possessing a lumen extending throughout a length of the second catheter, the second catheter being positioned in the lumen of the first catheter, the first and second catheters each possessing a distal end;

the introducing of the catheter assembly into the blood vessel including maintaining a portion of the catheter assembly exposed outside the body;

advancing a distal end portion of the catheter assembly into the lower limb of the patient's body by way of the aorta while the second catheter remains positioned in the lumen of the first catheter by operating the portion of the catheter assembly that is exposed outside the body so that the distal ends of both the first and second catheters are positioned in the lower limb of the patient's body;

introducing a treatment device into the lumen of the first catheter while the distal end of the first catheter is positioned in the lower limb of the patient's body;

advancing the treatment device through the lumen of the first catheter while the distal end of the first catheter is positioned in the lower limb of the patient's body to move the treatment device toward the treatment target in the lower limb of the patient's body; and treating the treatment target using the treatment device.

14. The treatment method according to claim 13, wherein the introducing of the treatment device into the lumen of the first catheter comprises introducing the treatment device into the lumen of the second catheter, and wherein the advancing of the treatment device through the lumen of the first catheter comprises advancing the treatment device through the lumen of the second catheter.

15. The treatment method according to claim 13, further comprising completely removing the second catheter from the lumen of the first catheter after the distal ends of both the first and second catheters are positioned in the lower limb of the patient's body and before the introducing of the treatment device into the lumen of the first catheter.

16. The treatment method according to claim 13, further comprising introducing a sheath into the blood vessel of the arm of the patient's body before introducing the catheter assembly into the blood vessel of the arm of the patient's body, the introducing of the catheter assembly into the blood vessel of the arm of the patient's body comprising introducing the catheter assembly into a lumen in the sheath.

17. The treatment method according to claim 16, wherein the introducing of the sheath into the blood vessel of the arm of the patient's body comprises introducing a sheath having an outer diameter equal to or smaller than 2.8 mm into the blood vessel of the arm of the patient's body.

18. The treatment method according to claim 13,
wherein the treatment target is located in a blood vessel closer to the peripheral side than to the popliteal artery in the lower limb, and the delivery of the distal end of the catheter assembly to the predetermined position of the lower limb includes delivering the distal end of the catheter assembly to a femoral artery or iliac artery, and during the advancing of the treatment device, the treatment device is sent to the femoral artery from the catheter assembly, and the treatment device is advanced to the popliteal artery.

19. The treatment method according to claim 13, wherein the first catheter includes a proximal end at which is located a first catheter hub, and the second catheter includes a proximal end at which is located a second catheter hub, the introducing of the catheter assembly into the blood vessel comprising introducing the catheter assembly into the blood vessel while the first catheter hub is fixed to the second catheter hub so that the first and second catheters as well as the first and second catheter hubs move together as a unit.

* * * * *